(12) United States Patent
Lorentsen et al.

(10) Patent No.: US 10,165,787 B2
(45) Date of Patent: *Jan. 1, 2019

(54) GH10 FAMILY XYLANASE

(71) Applicant: DuPont Nutrition Biosciences ApS, Copenhagen K (DK)

(72) Inventors: Rikke Hoeegh Lorentsen, Randers (DK); Susan Arent Lund, Braband (DK); Igor Nikolaev, Nordwijk (NL); Jan Hendrik A. Van Tuijl, Zoetermeer (NL); Bert Koops, Pijnacker (NL)

(73) Assignee: DUPONT NUTRITION BIOSCIENCES APS (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/114,914

(22) PCT Filed: Jan. 30, 2015

(86) PCT No.: PCT/EP2015/051982
§ 371 (c)(1),
(2) Date: Jul. 28, 2016

(87) PCT Pub. No.: WO2015/114112
PCT Pub. Date: Aug. 6, 2015

(65) Prior Publication Data
US 2016/0345609 A1 Dec. 1, 2016

(30) Foreign Application Priority Data
Jan. 31, 2014 (GB) .................................. 1401648.9

(51) Int. Cl.
| | |
|---|---|
| *C12N 9/42* | (2006.01) |
| *C12P 7/06* | (2006.01) |
| *C12P 19/14* | (2006.01) |
| *C12N 1/21* | (2006.01) |
| *C12N 15/56* | (2006.01) |
| *A23K 20/189* | (2016.01) |
| *C12N 9/24* | (2006.01) |
| *A23K 10/38* | (2016.01) |
| *C12C 5/00* | (2006.01) |
| *C12C 7/04* | (2006.01) |
| *A23K 10/30* | (2016.01) |
| *C12C 11/00* | (2006.01) |
| *C12P 19/02* | (2006.01) |

(52) U.S. Cl.
CPC ............ *A23K 20/189* (2016.05); *A23K 10/30* (2016.05); *A23K 10/38* (2016.05); *C12C 5/004* (2013.01); *C12C 7/04* (2013.01); *C12C 11/00* (2013.01); *C12N 9/248* (2013.01); *C12N 9/2482* (2013.01); *C12N 9/2485* (2013.01); *C12P 19/02* (2013.01); *C12P 19/14* (2013.01); *C12Y 302/01008* (2013.01); *Y02E 50/17* (2013.01); *Y02P 60/873* (2015.11)

(58) Field of Classification Search
None
See application file for complete search history.

(56) References Cited

U.S. PATENT DOCUMENTS

| | | | | |
|---|---|---|---|---|
| 2010/0035302 | A1* | 2/2010 | Broekaert | C12P 7/10 435/72 |
| 2016/0333332 | A1* | 11/2016 | Teunissen | C12N 9/2482 |

FOREIGN PATENT DOCUMENTS

| | | | |
|---|---|---|---|
| WO | WO2002/024926 | 3/2002 | |
| WO | WO-0238786 A1 * | 5/2002 | ............... C12N 9/00 |
| WO | 2003046169 A2 | 6/2003 | |
| WO | WO2009/045627 | 4/2009 | |

OTHER PUBLICATIONS

Uniprot, Accession No. C7Z894, 2012, www.uniprot.org.*
Kim et al., Production of hyperthermostable GH10 xylanase Xyl10B from Thermotoga maritima in transplastomic plants enables complete hydrolysis of methylglucuronoxylan to fermentable sugars for biofuel production, Plant Mol. Biol., 2011, 76, 357-69.*
GenBank, Accession No. AAD35164.1, 2010, www.ncbi.nlm.nih.gov.*
Wahl et al., Molecular Hybridization of Immobilized Nucleic Acids: Theoretical Concepts and Practical Considerations, Methods Enz., 1987, 152, 399-407.*
International Search Report, PCT Application No. PCT/EP2015/051982, dated Aug. 6, 2015.
Pollet et al., "Fusarium Graminearum Xylanases Show Different Functional Stabilities, Substrate Specificities and Inhibition Sensitivites", Enzyme and Microbial Technology, vol. 44, No. 4 (2009), pp. 189-195.
Verma et al., "Molecular Approaches for Ameliorating Microbial Xylanases", Bioresource Technology, vol. 117, (2012), pp. 360-367.
Motta et al., "A Review of Xylanase Production by the Fermentation of Xylan: Classification, Characterization and Applications", Chapter 10 of Sustainable Degradation of Lignocellulosic Biomass—Techniques, Applications, and Commercialization (2013), Intech.
Plant Mol. Biol., 2011, vol. 76, pp. 357-369.
Endo-1,4,-beta-xylanase B [Thermotoga maritima MSB8], GenBank Accession No. AAD35164, Mar. 5, 2010, [Date of search: Sep. 11, 2018] <URL:https://www.ncbi.nlm.nih.gov/protein/4980557?sat=18&satkey=1856132>.
Beta-xylanase, UniProt Accession No. N4V5TO, Jun. 26, 2013, [Date of search: Sep. 11, 2018] <URL:https://www.uniprot.org/uniprot/N4V5TO>.

* cited by examiner

Primary Examiner — Robert B Mondesi
Assistant Examiner — Todd M Epstein

(57) ABSTRACT

A GH10 xylanase variant is disclosed herein. This GH10 xylanase variant has increased thermostability compared with a parent GH10 xylanase enzyme comprising at least 90% sequence identity with the amino acid sequence of SEQ ID No. 1 wherein the variant has been modified at two or more of the following positions 7, 33, 79, 217 and 298 corresponding to the amino acid numbering of SEQ ID No. 1.

58 Claims, 27 Drawing Sheets
Specification includes a Sequence Listing.

FIGURE 1A

(SEQ ID NO. 26)

mklssflytaslvaa*IPTAIEPR*QAADSINKLIKNKGKLYYGTITDPNLLGVAKDTAIIKADFGAVTPEN
SGKWDATEPSQGKFNFGSFDQVVNFAQQNGLKVRGHTLVWHSQLPQWVKNINDKATLTK
VIENHVTQVVGRYKGKIYAWDVVNEIFEWDGTLRKDSHFNNVFGNDDYVGIAFRAARKADP
NAKLYINDYSLDSGSASKVTKGMVPSVKKWLSQGVPVDGIGSQTHLDPGAAGQIQGALTAL
ANSGVKEVAITELDIRTAPANDYATVTKACLNVPKCIGITVWGVSDKNSWRKEHDSLLFDAN
YNPKPAYTAVVNALR

FIGURE 1B

(SEQ ID No. 27)

*IPTAIEPR*QAADSINKLIKNKGKLYYGTITDPNLLGVAKDTAIIKADFGAVTPENSGKWDATEP
SQGKFNFGSFDQVVNFAQQNGLKVRGHTLVWHSQLPQWVKNINDKATLTKVIENHVTQVV
GRYKGKIYAWDVVNEIFEWDGTLRKDSHFNNVFGNDDYVGIAFRAARKADPNAKLYINDYS
LDSGSASKVTKGMVPSVKKWLSQGVPVDGIGSQTHLDPGAAGQIQGALTALANSGVKEVAI
TELDIRTAPANDYATVTKACLNVPKCIGITVWGVSDKNSWRKEHDSLLFDANYNPKPAYTAV
VNALR

FIGURE 1C

(SEQ ID No. 1)

QAADSINKLIKNKGKLYYGTITDPNLLGVAKDTAIIKADFGAVTPENSGKWDATEPSQGKFNFGSFDQVVNFAQQ
NGLKVRGHTLVWHSQLPQWVKNINDKATLTKVIENHVTQVVGRYKGKIYAWDVVNEIFEWDGTLRKDSHFNNVFG
NDDYVGIAFRAARKADPNAKLYINDYSLDSGSASKVTKGMVPSVKKWLSQGVPVDGIGSQTHLDPGAAGQIQGAL
TALANSGVKEVAITELDIRTAPANDYATVTKACLNVPKCIGITVWGVSDKNSWRKEHDSLLFDANYNPKPAYTAV
VNALR

FIGURE 2A (SEQ ID NO. 24)

ATGAAGCTGTCTTCTTTCCTCTACACCGCCTCGCTGGTCGCGGCCATTCCCACCGCCA
TCGAGCCCCGCCAGGCTGCCGACAGCATCAACAAGCTGATCAAGAACAAGGGCAAGCT
CTACTACGGAACCATCACCGACCCCAACCTGCTCGGCGTCGCAAAGGACACCGCCATC
ATCAAGGCCGACTTTGGCGCCGTTACCCCCGAGAACTCGGGCAAGTGGGACGCCACC
GAGCCCAGCCAGGGCAAGTTCAACTTCGGTAGCTTCGACCAGGTTGTCAACTTTGCCC
AGCAGAATGGCCTCAAGGTCCGAGGTCACACTCTGGTCTGGCACTCTCAGCTCCCTCA
GTGGGTTAAGAACATCAACGACAAGGCTACTCTGACCAAGGTCATTGAGAACCACGTCA
CCCAAGTCGTTGGACGCTACAAGGGCAAGATCTACGCCTGG**gtatgttttattccccagacttctt
cgaaatgactttgctaacatgttcag**GACGTCGTCAACGAGATCTTCGAGTGGGACGGTACCCTCC
GAAAGGACTCTCACTTCAACAACGTCTTCGGCAACGACGACTACGTTGGCATTGCCTTC
CGCGCCGCCCGCAAGGCTGACCCCAACGCCAAGCTGTACATCAACGACTACAGCCTCG
ACTCCGGCAGCGCCTCCAAGGTCACCAAGGGTATGGTTCCCTCCGTCAAGAAGTGGCT
CAGCCAGGGCGTTCCCGTCGACGGCATTGGCTCTCAGACTCACCTTGACCCCGGTGCC
GCTGGCCAAATCCAGGGTGCTCTCACTGCCCTCGCCAATTCTGGTGTCAAGGAGGTTG
CCATCACCGAGCTCGACATCCGCACTGCCCCCGCCAACGACTACGCTACCGTCACCAA
GGCCTGCCTCAACGTCCCCAAGTGCATTGGTATCACCGTCTGGGGTGTCTCTGACAAG
AACTCTTGGCGCAAGGAGCACGACAGTCTTCTGTTCGATGCTAACTACAACCCCAAGCC
TGCTTACACTGCTGTTGTCAACGCTCTCCGCTAA

FIGURE 2B (SEQ ID NO. 25)

ATGAAGCTGTCTTCTTTCCTCTACACCGCCTCGCTGGTCGCGGCCATTCCCACCGCCA
TCGAGCCCCGCCAGGCTGCCGACAGCATCAACAAGCTGATCAAGAACAAGGGCAAGCT
CTACTACGGAACCATCACCGACCCCAACCTGCTCGGCGTCGCAAAGGACACCGCCATC
ATCAAGGCCGACTTTGGCGCCGTTACCCCCGAGAACTCGGGCAAGTGGGACGCCACC
GAGCCCAGCCAGGGCAAGTTCAACTTCGGTAGCTTCGACCAGGTTGTCAACTTTGCCC
AGCAGAATGGCCTCAAGGTCCGAGGTCACACTCTGGTCTGGCACTCTCAGCTCCCTCA
GTGGGTTAAGAACATCAACGACAAGGCTACTCTGACCAAGGTCATTGAGAACCACGTCA
CCCAAGTCGTTGGACGCTACAAGGGCAAGATCTACGCCTGGGACGTCGTCAACGAGAT
CTTCGAGTGGGACGGTACCCTCCGAAAGGACTCTCACTTCAACAACGTCTTCGGCAAC
GACGACTACGTTGGCATTGCCTTCCGCGCCGCCCGCAAGGCTGACCCCAACGCCAAGC
TGTACATCAACGACTACAGCCTCGACTCCGGCAGCGCCTCCAAGGTCACCAAGGGTAT
GGTTCCCTCCGTCAAGAAGTGGCTCAGCCAGGGCGTTCCCGTCGACGGCATTGGCTCT
CAGACTCACCTTGACCCCGGTGCCGCTGGCCAAATCCAGGGTGCTCTCACTGCCCTCG
CCAATTCTGGTGTCAAGGAGGTTGCCATCACCGAGCTCGACATCCGCACTGCCCCCGC
CAACGACTACGCTACCGTCACCAAGGCCTGCCTCAACGTCCCCAAGTGCATTGGTATCA
CCGTCTGGGGTGTCTCTGACAAGAACTCTTGGCGCAAGGAGCACGACAGTCTTCTGTT
CGATGCTAACTACAACCCCAAGCCTGCTTACACTGCTGTTGTCAACGCTCTCCGCTAA

FIGURE 2C (SEQ ID NO. 2)

ATTCCCACCGCCATCGAGCCCCGCCAGGCTGCCGACAGCATCAACAAGCTGATCAAGAACAAGGGCAAGCTCTAC
TACGGAACCATCACCGACCCCAACCTGCTCGGCGTCGCAAAGGACACCGCCATCATCAAGGCCGACTTTGGCGCC
GTTACCCCCGAGAACTCGGGCAAGTGGGACGCCACCGAGCCCAGCCAGGGCAAGTTCAACTTCGGTAGCTTCGAC
CAGGTTGTCAACTTTGCCCAGCAGAATGGCCTCAAGGTCCGAGGTCACACTCTGGTCTGGCACTCTCAGCTCCCT
CAGTGGGTTAAGAACATCAACGACAAGGCTACTCTGACCAAGGTCATTGAGAACCACGTCACCCAAGTCGTTGGA
CGCTACAAGGGCAAGATCTACGCCTGGGACGTCGTCAACGAGATCTTCGAGTGGGACGGTACCCTCCGAAAGGAC
TCTCACTTCAACAACGTCTTCGGCAACGACGACTACGTTGGCATTGCCTTCCGCGCCGCCCGCAAGGCTGACCCC
AACGCCAAGCTGTACATCAACGACTACAGCCTCGACTCCGGCAGCGCCTCCAAGGTCACCAAGGGTATGGTTCCC
TCCGTCAAGAAGTGGCTCAGCCAGGGCGTTCCCGTCGACGGCATTGGCTCTCAGACTCACCTTGACCCCGGTGCC
GCTGGCCAAATCCAGGGTGCTCTCACTGCCCTCGCCAATTCTGGTGTCAAGGAGGTTGCCATCACCGAGCTCGAC
ATCCGCACTGCCCCCGCCAACGACTACGCTACCGTCACCAAGGCCTGCCTCAACGTCCCCAAGTGCATTGGTATC
ACCGTCTGGGGTGTCTCTGACAAGAACTCTTGGCGCAAGGAGCACGACAGTCTTCTGTTCGATGCTAACTACAAC
CCCAAGCCTGCTTACACTGCTGTTGTCAACGCTCTCCGCTAA

FIGURE 3A (SEQ ID No. 28)

mklssflytaslvaa*IPTAIEPR*QASDSINKLIKNKGKLYYGTITDPNLLGVAKDTAIIKADFGAVTPEN
SGKWDATEPSQGKFNFGSFDQVVNFAQQNGLKVRGHTLVWHSQLPQWVKNINDKATLTK
VIENHVTNVVGRYKGKIYAWDVVNEIFDWDGTLRKDSHFNNVFGNDDYVGIAFRAARKADP
NAKLYINDYSLDSGSASKVTKGMVPSVKKWLSQGVPVDGIGSQTHLDPGAAGQIQGALTAL
ANSGVKEVAITELDIRTAPANDYATVTKACLNVPKCIGITVWGVSDKNSWRKEHDSLLFDAN
YNPKAAYTAVVNALR

FIGURE 3B (SEQ ID No. 29)

*IPTAIEPR*QASDSINKLIKNKGKLYYGTITDPNLLGVAKDTAIIKADFGAVTPENSGKWDATEP
SQGKFNFGSFDQVVNFAQQNGLKVRGHTLVWHSQLPQWVKNINDKATLTKVIENHVTNVV
GRYKGKIYAWDVVNEIFDWDGTLRKDSHFNNVFGNDDYVGIAFRAARKADPNAKLYINDYS
LDSGSASKVTKGMVPSVKKWLSQGVPVDGIGSQTHLDPGAAGQIQGALTALANSGVKEVAI
TELDIRTAPANDYATVTKACLNVPKCIGITVWGVSDKNSWRKEHDSLLFDANYNPKAAYTAV
VNALR

FIGURE 3C (SEQ ID No. 3)

QASDSINKLIKNKGKLYYGTITDPNLLGVAKDTAIIKADFGAVTPENSGKWDATEPSQGKFNFGSFDQVVNFAQQ
NGLKVRGHTLVWHSQLPQWVKNINDKATLTKVIENHVTNVVGRYKGKIYAWDVVNEIFDWDGTLRKDSHFNNVFG
NDDYVGIAFRAARKADPNAKLYINDYSLDSGSASKVTKGMVPSVKKWLSQGVPVDGIGSQTHLDPGAAGQIQGAL
TALANSGVKEVAITELDIRTAPANDYATVTKACLNVPKCIGITVWGVSDKNSWRKEHDSLLFDANYNPKAAYTAV
VNALR

FIGURE 4A

SEQ ID No. 30

ATGAAGCTGTCTTCCTTCCTCTACACCGCCTCGCTGGTCGCGGCCATTCCCACCGCCA
TCGAGCCCCGCCAGGCCTCCGACAGCATCAACAAGCTGATCAAGAACAAGGGCAAGCT
CTACTACGGAACCATCACCGACCCCAACCTGCTCGGCGTCGCAAAGGACACTGCCATC
ATCAAGGCTGACTTTGGCGCCGTCACACCCGAGAACTCGGGTAAGTGGGATGCCACCG
AGCCCAGCCAGGGCAAGTTCAACTTCGGCAGCTTCGACCAGGTCGTCAACTTTGCTCA
GCAGAATGGCCTCAAGGTCCGAGGTCACACTCTAGTCTGGCACTCCCAGCTCCCTCAG
TGGGTTAAGAACATCAACGACAAGGCTACTTTGACCAAGGTCATCGAGAACCACGTCAC
CAACGTCGTTGGACGCTACAAGGGCAAGATCTACGCCTGG*gtatgttttcttcactcgaacttcttat*
*aaatggctttactaacatgttcag*GACGTCGTTAACGAGATCTTCGACTGGGATGGTACCCTCCGA
AAGGACTCTCACTTCAACAACGTCTTCGGCAACGACGACTACGTTGGCATTGCCTTCCG
CGCTGCCCGCAAGGCTGACCCCAACGCCAAGCTGTACATCAACGACTACAGCCTCGAC
TCCGGCAGCGCCTCCAAGGTCACCAAGGGCATGGTTCCCTCTGTCAAGAAGTGGCTCA
GCCAGGGCGTCCCCGTCGACGGTATTGGTTCTCAGACTCACCTTGACCCCGGTGCCGC
TGGCCAAATCCAGGGTGCTCTCACTGCCCTCGCCAACTCTGGTGTGAAGGAGGTTGCC
ATCACCGAGCTCGACATCCGCACTGCCCCGCCAACGACTACGCTACCGTTACCAAGG
CCTGCCTCAACGTCCCCAAGTGCATTGGTATCACCGTCTGGGGCGTATCTGACAAGAAC
TCTTGGCGCAAGGAGCACGACAGCCTTCTGTTCGATGCTAACTACAACCCCAAGGCTG
CTTACACTGCTGTTGTCAACGCTCTCCGCTAA

FIGURE 4B

SEQ ID No. 31

ATGAAGCTGTCTTCCTTCCTCTACACCGCCTCGCTGGTCGCGGCCATTCCCACCGCCA
TCGAGCCCCGCCAGGCCTCCGACAGCATCAACAAGCTGATCAAGAACAAGGGCAAGCT
CTACTACGGAACCATCACCGACCCCAACCTGCTCGGCGTCGCAAAGGACACTGCCATC
ATCAAGGCTGACTTTGGCGCCGTCACACCCGAGAACTCGGGTAAGTGGGATGCCACCG
AGCCCAGCCAGGGCAAGTTCAACTTCGGCAGCTTCGACCAGGTCGTCAACTTTGCTCA
GCAGAATGGCCTCAAGGTCCGAGGTCACACTCTAGTCTGGCACTCCCAGCTCCCTCAG
TGGGTTAAGAACATCAACGACAAGGCTACTTTGACCAAGGTCATCGAGAACCACGTCAC
CAACGTCGTTGGACGCTACAAGGGCAAGATCTACGCCTGGGACGTCGTTAACGAGATC
TTCGACTGGGATGGTACCCTCCGAAAGGACTCTCACTTCAACAACGTCTTCGGCAACGA
CGACTACGTTGGCATTGCCTTCCGCGCTGCCCGCAAGGCTGACCCCAACGCCAAGCTG
TACATCAACGACTACAGCCTCGACTCCGGCAGCGCCTCCAAGGTCACCAAGGGCATGG
TTCCCTCTGTCAAGAAGTGGCTCAGCCAGGGCGTCCCCGTCGACGGTATTGGTTCTCA
GACTCACCTTGACCCCGGTGCCGCTGGCCAAATCCAGGGTGCTCTCACTGCCCTCGCC
AACTCTGGTGTGAAGGAGGTTGCCATCACCGAGCTCGACATCCGCACTGCCCCCGCCA
ACGACTACGCTACCGTTACCAAGGCCTGCCTCAACGTCCCCAAGTGCATTGGTATCACC
GTCTGGGGCGTATCTGACAAGAACTCTTGGCGCAAGGAGCACGACAGCCTTCTGTTCG
ATGCTAACTACAACCCCAAGGCTGCTTACACTGCTGTTGTCAACGCTCTCCGCTAA

FIGURE 4C

SEQ ID No. 4

ATTCCCACCGCCATCGAGCCCCGCCAGGCCTCCGACAGCATCAACAAGCTGATCAAGAACAAGGGCAAGCTCTAC
TACGGAACCATCACCGACCCCAACCTGCTCGGCGTCGCAAAGGACACTGCCATCATCAAGGCTGACTTTGGCGCC
GTCACACCCGAGAACTCGGGTAAGTGGGATGCCACCGAGCCCAGCCAGGGCAAGTTCAACTTCGGCAGCTTCGAC
CAGGTCGTCAACTTTGCTCAGCAGAATGGCCTCAAGGTCCGAGGTCACACTCTAGTCTGGCACTCCCAGCTCCCT
CAGTGGGTTAAGAACATCAACGACAAGGCTACTTTGACCAAGGTCATCGAGAACCACGTCACCAACGTCGTTGGA
CGCTACAAGGGCAAGATCTACGCCTGGGACGTCGTTAACGAGATCTTCGACTGGGATGGTACCCTCCGAAAGGAC
TCTCACTTCAACAACGTCTTCGGCAACGACGACTACGTTGGCATTGCCTTCCGCGCTGCCCGCAAGGCTGACCCC
AACGCCAAGCTGTACATCAACGACTACAGCCTCGACTCCGGCAGCGCCTCCAAGGTCACCAAGGGCATGGTTCCC
TCTGTCAAGAAGTGGCTCAGCCAGGGCGTCCCCGTCGACGGTATTGGTTCTCAGACTCACCTTGACCCCGGTGCC
GCTGGCCAAATCCAGGGTGCTCTCACTGCCCTCGCCAACTCTGGTGTGAAGGAGGTTGCCATCACCGAGCTCGAC
ATCCGCACTGCCCCCGCCAACGACTACGCTACCGTTACCAAGGCCTGCCTCAACGTCCCCAAGTGCATTGGTATC
ACCGTCTGGGGCGTATCTGACAAGAACTCTTGGCGCAAGGAGCACGACAGCCTTCTGTTCGATGCTAACTACAAC
CCCAAGGCTGCTTACACTGCTGTTGTCAACGCTCTCCGCTAA

FIGURE 5

SEQ ID No. 5

QAADSINKLIKNKGKLYYGTITDPNLLGVAKDTAVIKADFGAVTPENSGKWDATEPSQGNFNFGSFDQVVNFAQQ
NGLKVRGHTLVWHSQLPQWVKNINDKATLTKVIENHVTQVVGRYKGKIYAWDVVNEIFDWDGTLRKDSHFNNVFG
NDDYVGIAFRAARKADPNAKLYINDYSLDSASASKVTKGMVPSVKKWLSQGVPVDGIGSQSHLDPGAAGQVQGAL
TALANSGVKEVAITELDIRTAPANDYATVTKACLNVPKCIGITVWGVSDKNSWRKEHDSLLFDSNYNPKPAYTAV
VNALR

FIGURE 6A

SEQ ID No. 32

ATGAAGCTGTCTTCTTTCCTCTACACCGCCTCGCTGGTCGCGGCCATTCCCACCGCCA
TCGAGCCCCGCCAGGCCGCCGACAGCATCAACAAGCTGATCAAGAACAAGGGCAAGCT
CTACTACGGAACCATCACCGACCCCAACCTGCTCGGCGTCGCAAAGGACACCGCCGTC
ATCAAGGCCGACTTTGGCGCCGTCACCCCCGAGAACTCGGGCAAGTGGGACGCCACC
GAGCCCAGCCAGGGCAACTTCAACTTCGGTAGCTTCGACCAGGTCGTCAACTTTGCTCA
GCAGAATGGCCTCAAGGTCCGAGGTCACACTCTGGTCTGGCACTCTCAGCTCCCTCAG
TGGGTTAAGAACATCAACGACAAGGCTACTCTGACCAAGGTCATTGAGAACCACGTCAC
CCAAGTCGTTGGACGCTACAAGGGCAAGATCTACGCCTGGgtatgttttcttgcctcgaccttctca
aagatgaatttgctaacatgttcagGACGTTGTCAACGAGATCTTCGACTGGGACGGTACCCTCCG
AAAGGATTCTCACTTCAACAACGTCTTCGGCAACGATGACTACGTTGGCATTGCCTTCC
GCGCCGCCCGCAAGGCTGACCCCAACGCCAAGCTGTACATCAACGACTACAGCCTCGA
CTCCGCCAGCGCCTCCAAGGTCACCAAGGGCATGGTCCCCTCCGTCAAGAAGTGGCTC
AGCCAGGGCGTTCCCGTCGACGGCATTGGCTCCAGTCTCACCTTGACCCCGGTGCCG
CTGGCCAAGTCCAGGGTGCTCTCACTGCCCTCGCCAACTCTGGTGTCAAGGAGGTTGC
CATCACCGAGCTCGACATCCGCACTGCCCCCGCCAACGACTACGCCACCGTCACCAAG
GCCTGCCTAAACGTCCCCAAGTGCATTGGTATCACCGTCTGGGGTGTCTCTGACAAGAA
CTCTTGGCGCAAGGAGCACGACAGCCTTCTGTTCGACTCCAACTACAACCCCAAGCCT
GCTTACACTGCTGTTGTCAACGCTCTCCGCTAA

FIGURE 6B (SEQ ID NO. 33)

ATGAAGCTGTCTTCTTTCCTCTACACCGCCTCGCTGGTCGCGGCCATTCCCACCGCCA
TCGAGCCCCGCCAGGCCGCCGACAGCATCAACAAGCTGATCAAGAACAAGGGCAAGCT
CTACTACGGAACCATCACCGACCCCAACCTGCTCGGCGTCGCAAAGGACACCGCCGTC
ATCAAGGCCGACTTTGGCGCCGTCACCCCCGAGAACTCGGGCAAGTGGGACGCCACC
GAGCCCAGCCAGGGCAACTTCAACTTCGGTAGCTTCGACCAGGTCGTCAACTTTGCTCA
GCAGAATGGCCTCAAGGTCCGAGGTCACACTCTGGTCTGGCACTCTCAGCTCCCTCAG
TGGGTTAAGAACATCAACGACAAGGCTACTCTGACCAAGGTCATTGAGAACCACGTCAC
CCAAGTCGTTGGACGCTACAAGGGCAAGATCTACGCCTGGGACGTTGTCAACGAGATC
TTCGACTGGGACGGTACCCTCCGAAAGGATTCTCACTTCAACAACGTCTTCGGCAACGA
TGACTACGTTGGCATTGCCTTCCGCGCCGCCCGCAAGGCTGACCCCAACGCCAAGCTG
TACATCAACGACTACAGCCTCGACTCCGCCAGCGCCTCCAAGGTCACCAAGGGCATGG
TCCCCTCCGTCAAGAAGTGGCTCAGCCAGGGCGTTCCCGTCGACGGCATTGGCTCCCA
GTCTCACCTTGACCCCGGTGCCGCTGGCCAAGTCCAGGGTGCTCTCACTGCCCTCGCC
AACTCTGGTGTCAAGGAGGTTGCCATCACCGAGCTCGACATCCGCACTGCCCCCGCCA
ACGACTACGCCACCGTCACCAAGGCCTGCCTAAACGTCCCCAAGTGCATTGGTATCAC
CGTCTGGGGTGTCTCTGACAAGAACTCTTGGCGCAAGGAGCACGACAGCCTTCTGTTC
GACTCCAACTACAACCCCAAGCCTGCTTACACTGCTGTTGTCAACGCTCTCCGCTAA

FIGURE 6C

(SEQ ID NO. 6)

ATTCCCACCGCCATCGAGCCCCGCCAGGCCGCCGACAGCATCAACAAGCTGATCAAGAACAAGGGCAAGCTCTAC
TACGGAACCATCACCGACCCCAACCTGCTCGGCGTCGCAAAGGACACCGCCGTCATCAAGGCCGACTTTGGCGCC
GTCACCCCCGAGAACTCGGGCAAGTGGGACGCCACCGAGCCCAGCCAGGGCAACTTCAACTTCGGTAGCTTCGAC
CAGGTCGTCAACTTTGCTCAGCAGAATGGCCTCAAGGTCCGAGGTCACACTCTGGTCTGGCACTCTCAGCTCCCT
CAGTGGGTTAAGAACATCAACGACAAGGCTACTCTGACCAAGGTCATTGAGAACCACGTCACCCAAGTCGTTGGA
CGCTACAAGGGCAAGATCTACGCCTGGGACGTTGTCAACGAGATCTTCGACTGGGACGGTACCCTCCGAAAGGAT
TCTCACTTCAACAACGTCTTCGGCAACGATGACTACGTTGGCATTGCCTTCCGCGCCGCCCGCAAGGCTGACCCC
AACGCCAAGCTGTACATCAACGACTACAGCCTCGACTCCGCCAGCGCCTCCAAGGTCACCAAGGGCATGGTCCCC
TCCGTCAAGAAGTGGCTCAGCCAGGGCGTTCCCGTCGACGGCATTGGCTCCCAGTCTCACCTTGACCCCGGTGCC
GCTGGCCAAGTCCAGGGTGCTCTCACTGCCCTCGCCAACTCTGGTGTCAAGGAGGTTGCCATCACCGAGCTCGAC
ATCCGCACTGCCCCGCCAACGACTACGCCACCGTCACCAAGGCCTGCCTAAACGTCCCCAAGTGCATTGGTATC
ACCGTCTGGGGTGTCTCTGACAAGAACTCTTGGCGCAAGGAGCACGACAGCCTTCTGTTCGACTCCAACTACAAC
CCCAAGCCTGCTTACACTGCTGTTGTCAACGCTCTCCGCTAA

FIGURE 8

SEQ ID No. 7
> variant enzyme A coding sequence (1bp - 987bp, direct) 987bp
ATGAAGCTGTCTTCTTTCCTCTACACCGCCTCGCTGGTCGCGGCCATTCCCACCGCCATCGAGCCCCGCC
AGGCTGCCGACAGCATCGACAAGCTGATCAAGAACAAGGGCAAGCTCTACTACGGAACCATCACCGACCC
CCCCCTGCTCGGCGTCGCAAAGGACGTCGCCATCATCAAGGCCGACTTTGGCGCCGTTACCCCCGAGAAC
TCGGGCAAGTGGGACGCCACCGAGCCCCAGCAGGGCAAGTTCACCTTCGGTAGCTTCGACCAGGTTGTCA
ACTTTGCCCAGCAGAATGGCCTCTACGTCCGAGGTCACACTCTGGTCTGGCACGGCCAGCTCCCTCAGTG
GGTTAAGAACATCAACGACAAGGCTATGCTGACCAAGGTCATTGAGAACCACGTCACCCAACTCGTTGGA
CGCTACAAGGGCAAGATCTACGCCTGGGACGTCGTCAACGAGATCTTCGAGTGGGACGGTACCCTCCGAA
AGGACTCTCACTTCAACCAGGTCTTCGGCAACGACGACTACGTTGGCATTGCCTTCCGCGCCGCCCGCAA
GGCTGACCCCAACGCCAAGCTGTACATCAACGACTACAGCCTCGACTCCCAGAGCGCCTCCAAGGTCACC
AAGGGTATGGTTCCCTACGTCAAGAAGTGGCTCAGCCAGGGCGTTCCCGTCGACGGCATTGGCTCTCAGA
CTCACCTTGACCCCGGTCAGGCTCCCCAAATCCAGGGTGCTCTCACTGCCCTCGCCAATTCTGGTGTCAA
GGAGGTTGCCATCACCGAGCTCGACATCCGCACTGCCCCCGCCAACGACTACGCTACCGTCACCAAGGCC
TGCCTCAACGTCCCCAAGTGCATTGGTATCACCGTCTGGGGTGTCTCTGACAAGAACTCTTGGCGCAAGG
AGCACGACAGTCTTCTGTTCGATGCTAACTACAACCCCAAGCCTGCTTACTACGCTGTTGTCAACGCTCT
CCGCTAA SEQ ID No. 8
>variant enzyme B coding sequence (1bp - 987bp, direct) 987bp
ATGAAGCTGTCTTCTTTCCTCTACACCGCCTCGCTGGTCGCGGCCATTCCCACCGCCATCGAGCCCCGCC
AGGCTGCCGACAGCATCGACAAGCTGATCAAGAACAAGGGCAAGCTCTACTACGGAACCATCACCGACCC
CCCCCTGCTCGGCGTCGCAAAGGACGTCGCCATCATCAAGGCCGACTTTGGCGCCGTTACCCCCGAGAAC
TCGGGCAAGTGGGACGCCACCGAGCCCCAGCAGGGCAAGTTCACCTTCACCAGCTTCGACCAGGTTGTCA
ACTTTGCCCAGCAGAATGGCCTCTACGTCCGAGGTCACACTCTGGTCTGGCACTCTCAGCTCCCTCAGTG
GGTTAAGAACATCAACGACAAGGCTATGCTGACCAAGGTCATTGAGAACCACGTCACCCAACTCGTTGGA
CGCTACAAGGGCAAGATCTACGCCTGGGACGTCGTCAACGAGATCTTCGAGTGGGACGGTACCCTCCGAA
AGGACTCTCACTTCAACCAGGTCTTCGGCAACGACGACTACGTTGGCATTGCCTTCCGCGCCGCCCGCAA
GGCTGACCCCAACGCCAAGCTGTACATCAACGACTACAGCCTCGACTCCCAGAGCGCCTCCAAGGTCACC
AAGGGTATGGTTCCCTACGTCAAGAAGTGGCTCAGCCAGGGCGTTCCCGTCGACGGCATTGGCTCTCAGA
CTCACCTTGACCCCGGTCAGGCTCCCCAAATCCAGGGTGCTCTCACTGCCCTCGCCAATTCTGGTGTCAA
GGAGGTTGCCATCACCGAGCTCGACATCCGCACTGCCCCCGCCAACGACTACGCTACCGTCACCAAGGCC
TGCCTCAACGTCCCCAAGTGCATTGGTATCACCGTCTGGGGTGTCTCTGACAAGAACTCTTGGCGCAAGG
AGCACGACAGTCTTCTGTTCGATGCTAACTACAACCCCAAGCCTGCTTACTACGCTGTTGTCAACGCTCT
CCGCTAA FIGURE 8 Cont'd SEQ ID No. 9

>variant enzyme C coding sequence (1bp - 987bp, direct) 987bp
ATGAAGCTGTCTTCTTTCCTCTACACCGCCTCGCTGGTCGCGGCCATTCCCACCGCCATCGAGCCCCGCC
AGGCTGCCGACAGCATCGACAAGCTGATCAAGAACAAGGGCAAGCTCTACTACGGAACCATCACCGACCC
CCCTCTGCTCGGCGTCGCAAAGGACGTCGCCATCATCAAGGCCGACTTTGGCGCCGTTACCCCCGAGAAC
TCGGGCAAGTGGGACGCCACCGAGCCCAGCCAGGGCAAGTTCAACTTCGGTAGCTTCGACCAGGTTGTCA
ACTTTGCCCAGCAGAATGGCCTCTACGTCCGAGGTCACACTCTGGTCTGGCACGGCCAGCTCCCTCAGTG
GGTTAAGAACATCAACGACAAGGCTACTCTGACCAAGGTCATTGAGAACCACGTCACCCAAGTCGTTGGA
CGCTACAAGGGCAAGATCTACGCCTGGGACGTCGTCAACGAGATCTTCGAGTGGGACGGTACCCTCCGAA
AGGACTCTCACTTCAACAACGTCTTCGGCAACGACGACTACGTTGGCATTGCCTTCCGCGCCGCCCGCAA
GGCTGACCCCAACGCCAAGCTGTACATCAACGACTACAGCCTCGACTCCGGCAGCGCCTCCAAGGTCACC
AAGGGTATGGTTCCCTCCGTCAAGAAGTGGCTCAGCCAGGGCGTTCCCGTCGACGGCATTGGCTCTCAGA
CTCACCTTGACCCCGGTCAGGCTGGCCAAATCCAGGGTGCTCTCACTGCCCTCGCCAATTCTGGTGTCAA
GGAGGTTGCCATCACCGAGCTCGACATCCGCACTGCCCCCGCCAACGACTACGCTACCGTCACCAAGGCC
TGCCTCAACGTCCCCAAGTGCATTGGTATCACCGTCTGGGGTGTCTCTGACAAGAACTCTTGGCGCAAGG
AGCACGACAGTCTTCTGTTCGATGCTAACTACAACCCCAAGCCTGCTTACTACGCTGTTGTCAACGCTCT
CCGCTAA SEQ ID No. 10

>variant enzyme D coding sequence (1bp - 987bp, direct) 987bp
ATGAAGCTGTCTTCTTTCCTCTACACCGCCTCGCTGGTCGCGGCCATTCCCACCGCCATCGAGCCCCGCC
AGGCTGCCGACAGCATCGACAAGCTGATCAAGAACAAGGGCAAGCTCTACTACGGAACCATCACCGACCC
CAACCTGCTCGGCGTCGCAAAGGACGTCGCCATCATCAAGGCCGACTTTGGCGCCGTTACCCCCGAGAAC
TCGGGCAAGTGGGACGCCACCGAGCCCAGCAGGGCAAGTTCACCTTCACCAGCTTCGACCAGGTTGTCA
ACTTTGCCCAGCAGAATGGCCTCTACGTCCGAGGTCACACTCTGGTCTGGCACGGCCAGCTCCCTCAGTG
GGTTAAGAACATCAACGACAAGGCTACTCTGACCAAGGTCATTGAGAACCACGTCACCCAAGTCGTTGGA
CGCTACAAGGGCAAGATCTACGCCTGGGACGTCGTCAACGAGATCTTCGAGTGGGACGGTACCCTCCGAA
AGGACTCTCACTTCAACAACGTCTTCGGCAACGACGACTACGTTGGCATTGCCTTCCGCGCCGCCCGCAA
GGCTGACCCCAACGCCAAGCTGTACATCAACGACTACAGCCTCGACTCCGGCAGCGCCTCCAAGGTCACC
AAGGGTATGGTTCCCTCCGTCAAGAAGTGGCTCAGCCAGGGCGTTCCCGTCGACGGCATTGGCTCTCAGA
CTCACCTTGACCCCGGTCAGGCTGGCCAAATCCAGGGTGCTCTCACTGCCCTCGCCAATTCTGGTGTCAA
GGAGGTTGCCATCACCGAGCTCGACATCCGCACTGCCCCCGCCAACGACTACGCTACCGTCACCAAGGCC
TGCCTCAACGTCCCCAAGTGCATTGGTATCACCGTCTGGGGTGTCTCTGACAAGAACTCTTGGCGCAAGG
AGCACGACAGTCTTCTGTTCGATGCTAACTACAACCCCAAGCCTGCTTACTACGCTGTTGTCAACGCTCT
CCGCTAA FIGURE 8 Cont'd SEQ ID No. 11

```
>variant enzyme E coding sequence (direct) 987bp
ATGAAGCTGTCTTCTTTCCTCTACACCGCCTCGCTGGTCGCGGCCATTCCCACCGCCATCGAGCCCCGCC
AGGCTGCCGACAGCATCGACAAGCTGATCAAGAACAAGGGCAAGCTCTACTACGGAACCATCACCGACCC
CCCCCTGCTCGGCGTCGCAAAGGACGTCGCCATCATCAAGGCCGACTTTGGCGCCGTTACCCCCGAGAAC
TCGGGCAAGTGGGACGCCACCGAGCCCAGCCAGGGCAAGTTCAACTTCACCAGCTTCGACCAGGTTGTCA
ACTTTGCCCAGCAGAATGGCCTCTACGTCCGAGGTCACACTCTGGTCTGGCACGGCCAGCTCCCTCAGTG
GGTTAAGAACATCAACGACAAGGCTACTCTGACCAAGGTCATTGAGAACCACGTCACCCAAGTCGTTGGA
CGCTACAAGGGCAAGATCTACGCCTGGGACGTCGTCAACGAGATCTTCGAGTGGGACGGTACCCTCCGAA
AGGACTCTCACTTCAACAACGTCTTCGGCAACGACGACTACGTTGGCATTGCCTTCCGCGCCGCCCGCAA
GGCTGACCCCAACGCCAAGCTGTACATCAACGACTACAGCCTCGACTCCGGCAGCGCCTCCAAGGTCACC
AAGGGTATGGTTCCCTCCGTCAAGAAGTGGCTCAGCCAGGGCGTTCCCGTCGACGGCATTGGCTCTCAGA
CTCACCTTGACCCCGGTCAGGCTGGCCAAATCCAGGGTGCTCTCACTGCCCTCGCCAATTCTGGTGTCAA
GGAGGTTGCCATCACCGAGCTCGACATCCGCACTGCCCCCGCCAACGACTACGCTACCGTCACCAAGGCC
TGCCTCAACGTCCCCAAGTGCATTGGTATCACCGTCTGGGGTGTCTCTGACAAGAACTCTTGGCGCAAGG
AGCACGACAGTCTTCTGTTCGATGCTAACTACAACCCCAAGCCTGCTTACTACGCTGTTGTCAACGCTCT
CCGCTAA
```

FIGURE 9

SEQ ID No. 12

>variant enzyme A (121bp - 1159bp, direct) 1039bp
ATGAAGCTGTCTTCTTTCCTCTACACCGCCTCGCTGGTCGCGGCCATTCCCACCGCCATCGAGCCCCGCC
AGGCTGCCGACAGCATCGACAAGCTGATCAAGAACAAGGGCAAGCTCTACTACGGAACCATCACCGACCC
CCCCCTGCTCGGCGTCGCAAAGGACGTCGCCATCATCAAGGCCGACTTTGGCGCCGTTACCCCCGAGAAC
TCGGGCAAGTGGGACGCCACCGAGCCCCAGCAGGGCAAGTTCACCTTCGGTAGCTTCGACCAGGTTGTCA
ACTTTGCCCAGCAGAATGGCCTCTACGTCCGAGGTCACACTCTGGTCTGGCACGGCCAGCTCCCTCAGTG
GGTTAAGAACATCAACGACAAGGCTATGCTGACCAAGGTCATTGAGAACCACGTCACCCAACTCGTTGGA
CGCTACAAGGGCAAGATCTACGCCTGGGTATGTTTATTCCCCAGACTTCTTCGAAATGACTTGCTAA
CATGTTCAGGACGTCGTCAACGAGATCTTCGAGTGGACGGTACCCTCCGAAAGGACTCTCACTTCAACC
AGGTCTTCGGCAACGACGACTACGTTGGCATTGCCTTCCGCGCCGCCCGCAAGGCTGACCCCAACGCCAA
GCTGTACATCAACGACTACAGCCTCGACTCCCAGAGCGCCTCCAAGGTCACCAAGGGTATGGTTCCCTAC
GTCAAGAAGTGGCTCAGCCAGGGCGTTCCCGTCGACGGCATTGGCTCTCAGACTCACCTTGACCCCGGTC
AGGCTCCCCAAATCCAGGGTGCTCTCACTGCCCTCGCCAATTCTGGTGTCAAGGAGGTTGCCATCACCGA
GCTCGACATCCGCACTGCCCCCGCCAACGACTACGCTACCGTCACCAAGGCCTGCCTCAACGTCCCCAAG
TGCATTGGTATCACCGTCTGGGGTGTCTCTGACAAGAACTCTTGGCGCAAGGAGCACGACAGTCTTCTGT
TCGATGCTAACTACAACCCCAAGCCTGCTTACTACGCTGTTGTCAACGCTCTCCGCTAA SEQ ID No. 13

>variant enzyme B (121bp - 1159bp, direct) 1039bp
ATGAAGCTGTCTTCTTTCCTCTACACCGCCTCGCTGGTCGCGGCCATTCCCACCGCCATCGAGCCCCGCC
AGGCTGCCGACAGCATCGACAAGCTGATCAAGAACAAGGGCAAGCTCTACTACGGAACCATCACCGACCC
CCCCCTGCTCGGCGTCGCAAAGGACGTCGCCATCATCAAGGCCGACTTTGGCGCCGTTACCCCCGAGAAC
TCGGGCAAGTGGGACGCCACCGAGCCCCAGCAGGGCAAGTTCACCTTCACCAGCTTCGACCAGGTTGTCA
ACTTTGCCCAGCAGAATGGCCTCTACGTCCGAGGTCACACTCTGGTCTGGCACTCTCAGCTCCCTCAGTG
GGTTAAGAACATCAACGACAAGGCTATGCTGACCAAGGTCATTGAGAACCACGTCACCCAACTCGTTGGA
CGCTACAAGGGCAAGATCTACGCCTGGGTATGTTTATTCCCCAGACTTCTTCGAAATGACTTGCTAA
CATGTTCAGGACGTCGTCAACGAGATCTTCGAGTGGACGGTACCCTCCGAAAGGACTCTCACTTCAACC
AGGTCTTCGGCAACGACGACTACGTTGGCATTGCCTTCCGCGCCGCCCGCAAGGCTGACCCCAACGCCAA
GCTGTACATCAACGACTACAGCCTCGACTCCCAGAGCGCCTCCAAGGTCACCAAGGGTATGGTTCCCTAC
GTCAAGAAGTGGCTCAGCCAGGGCGTTCCCGTCGACGGCATTGGCTCTCAGACTCACCTTGACCCCGGTC
AGGCTCCCCAAATCCAGGGTGCTCTCACTGCCCTCGCCAATTCTGGTGTCAAGGAGGTTGCCATCACCGA
GCTCGACATCCGCACTGCCCCCGCCAACGACTACGCTACCGTCACCAAGGCCTGCCTCAACGTCCCCAAG
TGCATTGGTATCACCGTCTGGGGTGTCTCTGACAAGAACTCTTGGCGCAAGGAGCACGACAGTCTTCTGT
TCGATGCTAACTACAACCCCAAGCCTGCTTACTACGCTGTTGTCAACGCTCTCCGCTAA FIGURE 9 Cont'd SEQ ID No. 14
>variant enzyme C (121bp - 1159bp, direct) 1039bp
ATGAAGCTGTCTTCTTTCCTCTACACCGCCTCGCTGGTCGCGGCCATTCCCACCGCCATCGAGCCCCGCC
AGGCTGCCGACAGCATCGACAAGCTGATCAAGAACAAGGGCAAGCTCTACTACGGAACCATCACCGACCC
CCCTCTGCTCGGCGTCGCAAAGGACGTCGCCATCATCAAGGCCGACTTTGGCGCCGTTACCCCCGAGAAC
TCGGGCAAGTGGGACGCCACCGAGCCCAGCCAGGGCAAGTTCAACTTCGGTAGCTTCGACCAGGTTGTCA
ACTTTGCCCAGCAGAATGGCCTCTACGTCCGAGGTCACACTCTGGTCTGGCACGGCCAGCTCCCTCAGTG
GGTTAAGAACATCAACGACAAGGCTACTCTGACCAAGGTCATTGAGAACCACGTCACCCAAGTCGTTGGA
CGCTACAAGGGCAAGATCTACGCCTGGGTATGTTTTATTCCCCCAGACTTCTTCGAAATGACTTTGCTAA
CATGTTCAGGACGTCGTCAACGAGATCTTCGAGTGGGACGGTACCCTCCGAAAGGACTCTCACTTCAACA
ACGTCTTCGGCAACGACGACTACGTTGGCATTGCCTTCCGCGCCGCCCGCAAGGCTGACCCCAACGCCAA
GCTGTACATCAACGACTACAGCCTCGACTCCGGCAGCGCCTCCAAGGTCACCAAGGGTATGGTTCCCTCC
GTCAAGAAGTGGCTCAGCCAGGGCGTTCCCGTCGACGGCATTGGCTCTCAGACTCACCTTGACCCCGGTC
AGGCTGGCCAAATCCAGGGTGCTCTCACTGCCCTCGCCAATTCTGGTGTCAAGGAGGTTGCCATCACCGA
GCTCGACATCCGCACTGCCCCCGCCAACGACTACGCTACCGTCACCAAGGCCTGCCTCAACGTCCCCAAG
TGCATTGGTATCACCGTCTGGGGTGTCTCTGACAAGAACTCTTGGCGCAAGGAGCACGACAGTCTTCTGT
TCGATGCTAACTACAACCCCAAGCCTGCTTACTACGCTGTTGTCAACGCTCTCCGCTAA SEQ ID No. 15
>variant enzyme D (46bp - 1084bp, direct) 1039bp
ATGAAGCTGTCTTCTTTCCTCTACACCGCCTCGCTGGTCGCGGCCATTCCCACCGCCATCGAGCCCCGCC
AGGCTGCCGACAGCATCGACAAGCTGATCAAGAACAAGGGCAAGCTCTACTACGGAACCATCACCGACCC
CAACCTGCTCGGCGTCGCAAAGGACGTCGCCATCATCAAGGCCGACTTTGGCGCCGTTACCCCCGAGAAC
TCGGGCAAGTGGGACGCCACCGAGCCCCAGCAGGGCAAGTTCAACCTTCACCAGCTTCGACCAGGTTGTCA
ACTTTGCCCAGCAGAATGGCCTCTACGTCCGAGGTCACACTCTGGTCTGGCACGGCCAGCTCCCTCAGTG
GGTTAAGAACATCAACGACAAGGCTACTCTGACCAAGGTCATTGAGAACCACGTCACCCAAGTCGTTGGA
CGCTACAAGGGCAAGATCTACGCCTGGGTATGTTTTATTCCCCCAGACTTCTTCGAAATGACTTTGCTAA
CATGTTCAGGACGTCGTCAACGAGATCTTCGAGTGGGACGGTACCCTCCGAAAGGACTCTCACTTCAACA
ACGTCTTCGGCAACGACGACTACGTTGGCATTGCCTTCCGCGCCGCCCGCAAGGCTGACCCCAACGCCAA
GCTGTACATCAACGACTACAGCCTCGACTCCGGCAGCGCCTCCAAGGTCACCAAGGGTATGGTTCCCTCC
GTCAAGAAGTGGCTCAGCCAGGGCGTTCCCGTCGACGGCATTGGCTCTCAGACTCACCTTGACCCCGGTC
AGGCTGGCCAAATCCAGGGTGCTCTCACTGCCCTCGCCAATTCTGGTGTCAAGGAGGTTGCCATCACCGA
GCTCGACATCCGCACTGCCCCCGCCAACGACTACGCTACCGTCACCAAGGCCTGCCTCAACGTCCCCAAG
TGCATTGGTATCACCGTCTGGGGTGTCTCTGACAAGAACTCTTGGCGCAAGGAGCACGACAGTCTTCTGT
TCGATGCTAACTACAACCCCAAGCCTGCTTACTACGCTGTTGTCAACGCTCTCCGCTAA FIGURE 9 Cont'd SEQ ID No. 16

```
>variant enzyme E (46bp - 1084bp, direct) 1039bp
ATGAAGCTGTCTTCTTTCCTCTACACCGCCTCGCTGGTCGCGGCCATTCCCACCGCCATCGAGCCCCGCC
AGGCTGCCGACAGCATCGACAAGCTGATCAAGAACAAGGGCAAGCTCTACTACGGAACCATCACCGACCC
CCCCCTGCTCGGCGTCGCAAAGGACGTCGCCATCATCAAGGCCGACTTTGGCGCCGTTACCCCCGAGAAC
TCGGGCAAGTGGGACGCCACCGAGCCCAGCCAGGGCAAGTTCAACTTCACCAGCTTCGACCAGGTTGTCA
ACTTTGCCCAGCAGAATGGCCTCTACGTCCGAGGTCACACTCTGGTCTGGCACGGCCAGCTCCCTCAGTG
GGTTAAGAACATCAACGACAAGGCTACTCTGACCAAGGTCATTGAGAACCACGTCACCCAAGTCGTTGGA
CGCTACAAGGGCAAGATCTACGCCTGGGTATGTTTTATTCCCCCAGACTTCTTCGAAATGACTTTGCTAA
CATGTTCAGGACGTCGTCAACGAGATCTTCGAGTGGGACGGTACCCTCCGAAAGGACTCTCACTTCAACA
ACGTCTTCGGCAACGACGACTACGTTGGCATTGCCTTCCGCGCCGCCCGCAAGGCTGACCCCAACGCCAA
GCTGTACATCAACGACTACAGCCTCGACTCCGGCAGCGCCTCCAAGGTCACCAAGGGTATGGTTCCCTCC
GTCAAGAAGTGGCTCAGCCAGGGCGTTCCCGTCGACGGCATTGGCTCTCAGACTCACCTTGACCCCGGTC
AGGCTGGCCAAATCCAGGGTGCTCTCACTGCCCTCGCCAATTCTGGTGTCAAGGAGGTTGCCATCACCGA
GCTCGACATCCGCACTGCCCCCGCCAACGACTACGCTACCGTCACCAAGGCCTGCCTCAACGTCCCCAAG
TGCATTGGTATCACCGTCTGGGGTGTCTCTGACAAGAACTCTTGGCGCAAGGAGCACGACAGTCTTCTGT
TCGATGCTAACTACAACCCCAAGCCTGCTTACTACGCTGTTGTCAACGCTCTCCGCTAA
```

FIGURE 10

SEQ ID No. 17

\>variant enzyme A mature 306aa

QAADSIDKLIKNKGKLYYGTITDPPLLGVAKDVAIIKADFGAVTPENSGKWDATEPQQGKFTFGSFDQVV
NFAQQNGLYVRGHTLVWHGQLPQWVKNINDKAMLTKVIENHVTQLVGRYKGKIYAWDVVNEIFEWDGTLR
KDSHFNQVFGNDDYVGIAFRAARKADPNAKLYINDYSLDSQSASKVTKGMVPYVKKWLSQGVPVDGIGSQ
THLDPGQAPQIQGALTALANSGVKEVAITELDIRTAPANDYATVTKACLNVPKCIGITVWGVSDKNSWRK
EHDSLLFDANYNPKPAYYAVVNALR*

SEQ ID No. 18

\>variant enzyme B mature 306aa

QAADSIDKLIKNKGKLYYGTITDPPLLGVAKDVAIIKADFGAVTPENSGKWDATEPQQGKFTFTSFDQVV
NFAQQNGLYVRGHTLVWHSQLPQWVKNINDKAMLTKVIENHVTQLVGRYKGKIYAWDVVNEIFEWDGTLR
KDSHFNQVFGNDDYVGIAFRAARKADPNAKLYINDYSLDSQSASKVTKGMVPYVKKWLSQGVPVDGIGSQ
THLDPGQAPQIQGALTALANSGVKEVAITELDIRTAPANDYATVTKACLNVPKCIGITVWGVSDKNSWRK
EHDSLLFDANYNPKPAYYAVVNALR*

SEQ ID No. 19

\>variant enzyme C mature 306aa

QAADSIDKLIKNKGKLYYGTITDPPLLGVAKDVAIIKADFGAVTPENSGKWDATEPSQGKFNFGSFDQVV
NFAQQNGLYVRGHTLVWHGQLPQWVKNINDKATLTKVIENHVTQVVGRYKGKIYAWDVVNEIFEWDGTLR
KDSHFNNVFGNDDYVGIAFRAARKADPNAKLYINDYSLDSGSASKVTKGMVPSVKKWLSQGVPVDGIGSQ
THLDPGQAGQIQGALTALANSGVKEVAITELDIRTAPANDYATVTKACLNVPKCIGITVWGVSDKNSWRK
EHDSLLFDANYNPKPAYYAVVNALR*

SEQ ID No. 20

\>variant enzyme D mature 306aa

QAADSIDKLIKNKGKLYYGTITDPNLLGVAKDVAIIKADFGAVTPENSGKWDATEPQQGKFTFTSFDQVV
NFAQQNGLYVRGHTLVWHGQLPQWVKNINDKATLTKVIENHVTQVVGRYKGKIYAWDVVNEIFEWDGTLR
KDSHFNNVFGNDDYVGIAFRAARKADPNAKLYINDYSLDSGSASKVTKGMVPSVKKWLSQGVPVDGIGSQ
THLDPGQAGQIQGALTALANSGVKEVAITELDIRTAPANDYATVTKACLNVPKCIGITVWGVSDKNSWRK
EHDSLLFDANYNPKPAYYAVVNALR*

SEQ ID No. 21

\>variant enzyme E 306aa

QAADSIDKLIKNKGKLYYGTITDPPLLGVAKDVAIIKADFGAVTPENSGKWDATEPSQGKFNFTSFDQVV
NFAQQNGLYVRGHTLVWHGQLPQWVKNINDKATLTKVIENHVTQVVGRYKGKIYAWDVVNEIFEWDGTLR
KDSHFNNVFGNDDYVGIAFRAARKADPNAKLYINDYSLDSGSASKVTKGMVPSVKKWLSQGVPVDGIGSQ
THLDPGQAGQIQGALTALANSGVKEVAITELDIRTAPANDYATVTKACLNVPKCIGITVWGVSDKNSWRK
EHDSLLFDANYNPKPAYYAVVNALR*

SEQUENCE LISTING

```
<160> NUMBER OF SEQ ID NOS: 35

<210> SEQ ID NO 1
<211> LENGTH: 305
<212> TYPE: PRT
<213> ORGANISM: Fusarium verticillioides

<400> SEQUENCE: 1

Gln Ala Ala Asp Ser Ile Asn Lys Leu Ile Lys Asn Lys Gly Lys Leu
1               5                   10                  15

Tyr Tyr Gly Thr Ile Thr Asp Pro Asn Leu Leu Gly Val Ala Lys Asp
            20                  25                  30

Thr Ala Ile Ile Lys Ala Asp Phe Gly Ala Val Thr Pro Glu Asn Ser
        35                  40                  45
```

```
Gly Lys Trp Asp Ala Thr Glu Pro Ser Gln Gly Lys Phe Asn Phe Gly
     50                  55                  60

Ser Phe Asp Gln Val Val Asn Phe Ala Gln Gln Asn Gly Leu Lys Val
 65                  70                  75                  80

Arg Gly His Thr Leu Val Trp His Ser Gln Leu Pro Gln Trp Val Lys
                 85                  90                  95

Asn Ile Asn Asp Lys Ala Thr Leu Thr Lys Val Ile Glu Asn His Val
                100                 105                 110

Thr Gln Val Val Gly Arg Tyr Lys Gly Lys Ile Tyr Ala Trp Asp Val
            115                 120                 125

Val Asn Glu Ile Phe Glu Trp Asp Gly Thr Leu Arg Lys Asp Ser His
130                 135                 140

Phe Asn Val Phe Gly Asn Asp Asp Tyr Val Gly Ile Ala Phe Arg
145                 150                 155                 160

Ala Ala Arg Lys Ala Asp Pro Asn Ala Lys Leu Tyr Ile Asn Asp Tyr
                165                 170                 175

Ser Leu Asp Ser Gly Ser Ala Ser Lys Val Thr Lys Gly Met Val Pro
                180                 185                 190

Ser Val Lys Lys Trp Leu Ser Gln Gly Val Pro Val Asp Gly Ile Gly
            195                 200                 205

Ser Gln Thr His Leu Asp Pro Gly Ala Ala Gly Gln Ile Gln Gly Ala
        210                 215                 220

Leu Thr Ala Leu Ala Asn Ser Gly Val Lys Glu Val Ala Ile Thr Glu
225                 230                 235                 240

Leu Asp Ile Arg Thr Ala Pro Ala Asn Asp Tyr Ala Thr Val Thr Lys
                245                 250                 255

Ala Cys Leu Asn Val Pro Lys Cys Ile Gly Ile Thr Val Trp Gly Val
            260                 265                 270

Ser Asp Lys Asn Ser Trp Arg Lys Glu His Asp Ser Leu Leu Phe Asp
        275                 280                 285

Ala Asn Tyr Asn Pro Lys Pro Ala Tyr Thr Ala Val Val Asn Ala Leu
    290                 295                 300

Arg
305

<210> SEQ ID NO 2
<211> LENGTH: 942
<212> TYPE: DNA
<213> ORGANISM: Fusarium verticillioides

<400> SEQUENCE: 2
attcccaccg ccatcgagcc ccgccaggct gccgacagca tcaacaagct gatcaagaac     60
aagggcaagc tctactacgg aaccatcacc gaccccaacc tgctcggcgt cgcaaaggac    120
accgccatca tcaaggccga ctttggcgcc gttaccccg  agaactcggg caagtgggac    180
gccaccgagc ccagccaggg caagttcaac ttcgtagct  tcgaccaggt tgtcaacttt    240
gcccagcaga atggcctcaa ggtccgaggt cacactctgg tctggcactc tcagctccct    300
cagtgggtta agaacatcaa cgacaaggct actctgacca aggtcattga gaaccacgtc    360
acccaagtcg ttggacgcta caagggcaag atctacgcct gggacgtcgt caacgagatc    420
ttcgagtggg acggtaccct ccgaaaggac tctcacttca acgtcttc   ggcaacgac    480 gactacgttg gcattgcctt ccgcgccgcc cgcaaggctg accccaacgc caagctgtac    540
atcaacgact acagcctcga ctccggcagc gcctccaagg tcaccaaggg tatggttccc    600
```

```
tccgtcaaga agtggctcag ccagggcgtt cccgtcgacg gcattggctc tcagactcac      660
cttgaccccg gtgccgctgg ccaaatccag ggtgctctca ctgccctcgc caattctggt      720
gtcaaggagg ttgccatcac cgagctcgac atccgcactg cccccgccaa cgactacgct      780
accgtcacca aggcctgcct caacgtcccc aagtgcattg gtatcaccgt ctggggtgtc      840
tctgacaaga actcttggcg caaggagcac gacagtcttc tgttcgatgc taactacaac      900
cccaagcctg cttacactgc tgttgtcaac gctctccgct aa                        942

<210> SEQ ID NO 3
<211> LENGTH: 305
<212> TYPE: PRT
<213> ORGANISM: Fusarium oxysporum

<400> SEQUENCE: 3

Gln Ala Ser Asp Ser Ile Asn Lys Leu Ile Lys Asn Lys Gly Lys Leu
1               5                   10                  15

Tyr Tyr Gly Thr Ile Thr Asp Pro Asn Leu Leu Gly Val Ala Lys Asp

<210> SEQ ID NO 4
<211> LENGTH: 942
<212> TYPE: DNA
<213> ORGANISM: Fusarium oxysporum

<400> SEQUENCE: 4

```
attcccaccg ccatcgagcc ccgccaggcc tccgacagca tcaacaagct gatcaagaac      60
aagggcaagc tctactacgg aaccatcacc gaccccaacc tgctcggcgt cgcaaaggac     120
actgccatca tcaaggctga ctttggcgcc gtcacacccg agaactcggg taagtgggat     180
gccaccgagc ccagccaggg caagttcaac ttcggcagct tcgaccaggt cgtcaacttt     240
gctcagcaga atggcctcaa ggtccgaggt cacactctag tctggcactc ccagctccct     300
cagtgggtta agaacatcaa cgacaaggct actttgacca aggtcatcga gaaccacgtc     360
accaacgtcg ttggacgcta caagggcaag atctacgcct gggacgtcgt taacgagatc     420
ttcgactggg atggtaccct ccgaaaggac tctcacttca acaacgtctt cggcaacgac     480
gactacgttg gcattgcctt ccgcgctgcc cgcaaggctg accccaacgc caagctgtac     540
atcaacgact acagcctcga ctccggcagc gcctccaagg tcaccaaggg catggttccc     600
tctgtcaaga agtggctcag ccagggcgtc cccgtcgacg gtattggttc tcagactcac     660
cttgaccccg gtgccgctgg ccaaatccag ggtgctctca ctgccctcgc caactctggt     720
gtgaaggagg ttgccatcac cgagctcgac atccgcactg ccccgccaa cgactacgct     780
accgttacca aggcctgcct caacgtcccc aagtgcattg gtatcaccgt ctggggcgta     840
tctgacaaga actcttggcg caaggagcac gacagccttc tgttcgatgc taactacaac     900
cccaaggctg cttacactgc tgttgtcaac gctctccgct aa                         942
```

<210> SEQ ID NO 5
<211> LENGTH: 305
<212> TYPE: PRT
<213> ORGANISM: Fusarium sp.

<400> SEQUENCE: 5

```
Gln Ala Ala Asp Ser Ile Asn Lys Leu Ile Lys Asn Lys Gly Lys Leu
1               5                   10                  15

Tyr Tyr Gly Thr Ile Thr Asp Pro Asn Leu Leu Gly Val Ala Lys Asp
            20                  25                  30

Thr Ala Val Ile Lys Ala Asp Phe Gly Ala Val Thr Pro Glu Asn Ser
        35                  40                  45

Gly Lys Trp Asp Ala Thr Glu Pro Ser Gln Gly Asn Phe Asn Phe Gly
    50                  55                  60

Ser Phe Asp Gln Val Val Asn Phe Ala Gln Gln Asn Gly Leu Lys Val
65                  70                  75                  80

Arg Gly His Thr Leu Val Trp His Ser Gln Leu Pro Gln Trp Val Lys
                85                  90                  95

Asn Ile Asn Asp Lys Ala Thr Leu Thr Lys Val Ile Glu Asn His Val
            100                 105                 110

Thr Gln Val Val Gly Arg Tyr Lys Gly Lys Ile Tyr Ala Trp Asp Val
        115                 120                 125

Val Asn Glu Ile Phe Asp Trp Asp Gly Thr Leu Arg Lys Asp Ser His
    130                 135                 140

Phe Asn Asn Val Phe Gly Asn Asp Asp Tyr Val Gly Ile Ala Phe Arg
145                 150                 155                 160
```

```
Ala Ala Arg Lys Ala Asp Pro Asn Ala Lys Leu Tyr Ile Asn Asp Tyr
            165                 170                 175

Ser Leu Asp Ser Ala Ser Ala Ser Lys Val Thr Lys Gly Met Val Pro
        180                 185                 190

Ser Val Lys Lys Trp Leu Ser Gln Gly Val Pro Val Asp Gly Ile Gly
            195                 200                 205

Ser Gln Ser His Leu Asp Pro Gly Ala Ala Gly Gln Val Gln Gly Ala
    210                 215                 220

Leu Thr Ala Leu Ala Asn Ser Gly Val Lys Glu Val Ala Ile Thr Glu
225                 230                 235                 240

Leu Asp Ile Arg Thr Ala Pro Ala Asn Asp Tyr Ala Thr Val Thr Lys
                245                 250                 255

Ala Cys Leu Asn Val Pro Lys Cys Ile Gly Ile Thr Val Trp Gly Val
            260                 265                 270

Ser Asp Lys Asn Ser Trp Arg Lys Glu His Asp Ser Leu Leu Phe Asp
        275                 280                 285

Ser Asn Tyr Asn Pro Lys Pro Ala Tyr Thr Ala Val Val Asn Ala Leu
    290                 295                 300

Arg
305

<210> SEQ ID NO 6
<211> LENGTH: 942
<212> TYPE: DNA
<213> ORGANISM: Fusarium sp.

<400> SEQUENCE: 6
attcccaccg ccatcgagcc ccgccaggcc gccgacagca tcaacaagct gatcaagaac      60
aagggcaagc tctactacgg aaccatcacc gaccccaacc tgctcggcgt cgcaaaggac     120
accgccgtca tcaaggccga cttggcgcc gtcaccccg agaactcggg caagtgggac      180
gccaccgagc ccagccaggg caacttcaac ttcggtagct tcgaccaggt cgtcaacttt     240
gctcagcaga atggcctcaa ggtccgaggt cacactctgg tctggcactc tcagctccct     300
cagtgggtta agaacatcaa cgacaaggct actctgacca aggtcattga gaaccacgtc     360
acccaagtcg ttggacgcta caagggcaag atctacgcct gggacgttgt caacgagatc     420
ttcgactggg acgttaccct ccgaaaggat tctcacttca acaacgtctt cggcaacgat     480
gactacgttg gcattgcctt ccgcgccgcc cgcaaggctg accccaacgc caagctgtac     540
atcaacgact acagcctcga ctccgccagc gcctccaagg tcaccaaggg catggtcccc     600
tccgtcaaga agtggctcag ccagggcgtt cccgtcgacg gcattggctc ccagtctcac     660
cttgaccccg gtgccgctgg ccaagtccag ggtgctctca ctgccctcgc caactctggt     720
gtcaaggagg ttgccatcac cgagctcgac atccgcactg ccccgccaa cgactacgcc      780 accgtcacca aggcctgcct aaacgtcccc aagtgcattg gtatcaccgt ctggggtgtc     840
tctgacaaga actcttggcg caaggagcac gacagccttc tgttcgactc caactacaac     900
cccaagcctg cttacactgc tgttgtcaac gctctccgct aa                         942

<210> SEQ ID NO 7
<211> LENGTH: 987
<212> TYPE: DNA
<213> ORGANISM: Artificial Sequence
<220> FEATURE:
<223> OTHER INFORMATION: Variant GH10 xylanase sequence

<400> SEQUENCE: 7
```

```
atgaagctgt cttctttcct ctacaccgcc tcgctggtcg cggccattcc caccgccatc    60
gagccccgcc aggctgccga cagcatcgac aagctgatca agaacaaggg caagctctac   120
tacggaacca tcaccgaccc ccccctgctc ggcgtcgcaa aggacgtcgc catcatcaag   180
gccgactttg gcgccgttac ccccgagaac tcgggcaagt gggacgccac cgagccccag   240
cagggcaagt tcaccttcgg tagcttcgac caggttgtca actttgccca gcagaatggc   300
ctctacgtcc gaggtcacac tctggtctgg cacggccagc tccctcagtg ggttaagaac   360
atcaacgaca aggctatgct gaccaaggtc attgagaacc acgtcaccca actcgttgga   420
cgctacaagg gcaagatcta cgcctgggac gtcgtcaacg agatcttcga gtgggacggt   480
accctccgaa aggactctca cttcaaccag gtcttcggca acgacgacta cgttggcatt   540
gccttccgcg ccgcccgcaa ggctgacccc aacgccaagc tgtacatcaa cgactacagc   600
ctcgactccc agagcgcctc caaggtcacc aagggtatgg ttccctacgt caagaagtgg   660
ctcagccagg gcgttcccgt cgacggcatt ggctctcaga ctcaccttga ccccggtcag   720
gctccccaaa tccagggtgc tctcactgcc ctcgccaatt ctggtgtcaa ggaggttgcc   780
atcaccgagc tcgacatccg cactgccccc gccaacgact acgctaccgt caccaaggcc   840
tgcctcaacg tccccaagtg cattggtatc accgtctggg gtgtctctga caagaactct   900
tggcgcaagg agcacgacag tcttctgttc gatgctaact acaaccccaa gcctgcttac   960
tacgctgttg tcaacgctct ccgctaa                                       987

<210> SEQ ID NO 8
<211> LENGTH: 987
<212> TYPE: DNA
<213> ORGANISM: Artificial Sequence
<220> FEATURE:
<223> OTHER INFORMATION: Variant GH10 xylanase sequence

<400> SEQUENCE: 8
atgaagctgt cttctttcct ctacaccgcc tcgctggtcg cggccattcc caccgccatc    60
gagccccgcc aggctgccga cagcatcgac aagctgatca agaacaaggg caagctctac   120
tacggaacca tcaccgaccc ccccctgctc ggcgtcgcaa aggacgtcgc catcatcaag   180
gccgactttg gcgccgttac ccccgagaac tcgggcaagt gggacgccac cgagccccag   240
cagggcaagt tcaccttcac cagcttcgac caggttgtca actttgccca gcagaatggc   300
ctctacgtcc gaggtcacac tctggtctgg cactctcagc tccctcagtg ggttaagaac   360
atcaacgaca aggctatgct gaccaaggtc attgagaacc acgtcaccca actcgttgga   420
cgctacaagg gcaagatcta cgcctgggac gtcgtcaacg agatcttcga gtgggacggt   480
accctccgaa aggactctca cttcaaccag gtcttcggca acgacgacta cgttggcatt   540
gccttccgcg ccgcccgcaa ggctgacccc aacgccaagc tgtacatcaa cgactacagc   600
ctcgactccc agagcgcctc caaggtcacc aagggtatgg ttccctacgt caagaagtgg   660
ctcagccagg gcgttcccgt cgacggcatt ggctctcaga ctcaccttga ccccggtcag   720
gctccccaaa tccagggtgc tctcactgcc ctcgccaatt ctggtgtcaa ggaggttgcc   780
atcaccgagc tcgacatccg cactgccccc gccaacgact acgctaccgt caccaaggcc   840
tgcctcaacg tccccaagtg cattggtatc accgtctggg gtgtctctga caagaactct   900
tggcgcaagg agcacgacag tcttctgttc gatgctaact acaaccccaa gcctgcttac   960
tacgctgttg tcaacgctct ccgctaa                                       987
```

<210> SEQ ID NO 9
<211> LENGTH: 987
<212> TYPE: DNA
<213> ORGANISM: Artificial Sequence
<220> FEATURE:
<223> OTHER INFORMATION: Variant GH10 xylanase sequence

<400> SEQUENCE: 9

```
atgaagctgt cttctttcct ctacaccgcc tcgctggtcg cggccattcc caccgccatc    60
gagccccgcc aggctgccga cagcatcgac aagctgatca agaacaaggg caagctctac   120
tacggaacca tcaccgaccc ccctctgctc ggcgtcgcaa aggacgtcgc catcatcaag   180
gccgactttg gcgccgttac ccccgagaac tcgggcaagt gggacgccac cgagcccagc   240
cagggcaagt tcaacttcgg tagcttcgac caggttgtca actttgccca gcagaatggc   300
ctctacgtcc gaggtcacac tctggtctgg cacggccagc ccctcagtg ggttaagaac    360
atcaacgaca aggctactct gaccaaggtc attgagaacc acgtcaccca agtcgttgga   420
cgctacaagg gcaagatcta cgcctgggac gtcgtcaacg agatcttcga gtgggacggt   480
accctccgaa aggactctca cttcaacaac gtcttcggca acgacgacta cgttggcatt   540
gccttccgcg ccgcccgcaa ggctgacccc aacgccaagc tgtacatcaa cgactacagc   600
ctcgactccg gcagcgcctc caaggtcacc aagggtatgg ttccctccgt caagaagtgg   660
ctcagccagg gcgttcccgt cgacggcatt ggctctcaga ctcaccttga ccccggtcag   720
gctggccaaa tccagggtgc tctcactgcc ctcgccaatt ctggtgtcaa ggaggttgcc   780
atcaccgagc tcgacatccg cactgccccc gccaacgact acgctaccgt caccaaggcc   840
tgcctcaacg tccccaagtg cattggtatc accgtctggg gtgtctctga caagaactct   900
tggcgcaagg agcacgacag tcttctgttc gatgctaact acaaccccaa gcctgcttac   960
tacgctgttg tcaacgctct ccgctaa                                       987
```

<210> SEQ ID NO 10
<211> LENGTH: 987
<212> TYPE: DNA
<213> ORGANISM: Artificial Sequence
<220> FEATURE:
<223> OTHER INFORMATION: Variant GH10 xylanase sequence

<400> SEQUENCE: 10

```
atgaagctgt cttctttcct ctacaccgcc tcgctggtcg cggccattcc caccgccatc    60
gagccccgcc aggctgccga cagcatcgac aagctgatca agaacaaggg caagctctac   120
tacggaacca tcaccgaccc caacctgctc ggcgtcgcaa aggacgtcgc catcatcaag   180
gccgactttg gcgccgttac ccccgagaac tcgggcaagt gggacgccac cgagcccag    240
cagggcaagt tcaccttcac cagcttcgac caggttgtca actttgccca gcagaatggc   300
ctctacgtcc gaggtcacac tctggtctgg cacggccagc ccctcagtg ggttaagaac    360
atcaacgaca aggctactct gaccaaggtc attgagaacc acgtcaccca agtcgttgga   420
cgctacaagg gcaagatcta cgcctgggac gtcgtcaacg agatcttcga gtgggacggt   480
accctccgaa aggactctca cttcaacaac gtcttcggca acgacgacta cgttggcatt   540
gccttccgcg ccgcccgcaa ggctgacccc aacgccaagc tgtacatcaa cgactacagc   600
ctcgactccg gcagcgcctc caaggtcacc aagggtatgg ttccctccgt caagaagtgg   660
ctcagccagg gcgttcccgt cgacggcatt ggctctcaga ctcaccttga ccccggtcag   720
gctggccaaa tccagggtgc tctcactgcc ctcgccaatt ctggtgtcaa ggaggttgcc   780
```

```
atcaccgagc tcgacatccg cactgccccc gccaacgact acgctaccgt caccaaggcc    840
tgcctcaacg tccccaagtg cattggtatc accgtctggg gtgtctctga caagaactct    900
tggcgcaagg agcacgacag tcttctgttc gatgctaact acaaccccaa gcctgcttac    960
tacgctgttg tcaacgctct ccgctaa                                        987

<210> SEQ ID NO 11
<211> LENGTH: 987
<212> TYPE: DNA
<213> ORGANISM: Artificial Sequence
<220> FEATURE:
<223> OTHER INFORMATION: Variant GH10 xylanase sequence

<400> SEQUENCE: 11
atgaagctgt cttctttcct ctacaccgcc tcgctggtcg cggccattcc caccgccatc     60
gagccccgcc aggctgccga cagcatcgac aagctgatca agaacaaggg caagctctac    120
tacggaacca tcaccgaccc ccccctgctc ggcgtcgcaa aggacgtcgc catcatcaag    180
gccgactttg cgccgttac ccccgagaac tcgggcaagt gggacgccac cgagcccagc    240
cagggcaagt tcaacttcac cagcttcgac caggttgtca actttgccca gcagaatggc    300
ctctacgtcc gaggtcacac tctggtctgg cacggccagc tccctcagtg ggttaagaac    360
atcaacgaca aggctactct gaccaaggtc attgagaacc acgtcaccca agtcgttgga    420
cgctacaagg gcaagatcta cgcctgggac gtcgtcaacg agatcttcga gtgggacggt    480
accctccgaa aggactctca cttcaacaac gtcttcggca acgacgacta cgttggcatt    540
gccttccgcg ccgcccgcaa ggctgacccc aacgccaagc tgtacatcaa cgactacagc    600
ctcgactccg gcagcgcctc caaggtcacc aagggtatgg ttccctccgt caagaagtgg    660
ctcagccagg gcgttcccgt cgacggcatt ggctctcaga ctcaccttga ccccggtcag    720
gctggccaaa tccagggtgc tctcactgcc ctcgccaatt ctggtgtcaa ggaggttgcc    780
atcaccgagc tcgacatccg cactgccccc gccaacgact acgctaccgt caccaaggcc    840
tgcctcaacg tccccaagtg cattggtatc accgtctggg gtgtctctga caagaactct    900
tggcgcaagg agcacgacag tcttctgttc gatgctaact acaaccccaa gcctgcttac    960
tacgctgttg tcaacgctct ccgctaa                                        987

<210> SEQ ID NO 12
<211> LENGTH: 1039
<212> TYPE: DNA
<213> ORGANISM: Artificial Sequence
<220> FEATURE:
<223> OTHER INFORMATION: Variant GH10 xylanase sequence

<400> SEQUENCE: 12
atgaagctgt cttctttcct ctacaccgcc tcgctggtcg cggccattcc caccgccatc     60
gagccccgcc aggctgccga cagcatcgac aagctgatca agaacaaggg caagctctac    120
tacggaacca tcaccgaccc ccccctgctc ggcgtcgcaa aggacgtcgc catcatcaag    180
gccgactttg cgccgttac ccccgagaac tcgggcaagt gggacgccac cgagcccag     240 cagggcaagt tcaccttcgg tagcttcgac caggttgtca actttgccca gcagaatggc    300
ctctacgtcc gaggtcacac tctggtctgg cacggccagc tccctcagtg ggttaagaac    360
atcaacgaca aggctatgct gaccaaggtc attgagaacc acgtcaccca actcgttgga    420
cgctacaagg gcaagatcta cgcctgggta tgttttattc ccccagactt cttcgaaatg    480
```

| | |
|---|---|
| actttgctaa catgttcagg acgtcgtcaa cgagatcttc gagtgggacg gtaccctccg | 540 |
| aaaggactct cacttcaacc aggtcttcgg caacgacgac tacgttggca ttgccttccg | 600 |
| cgccgcccgc aaggctgacc ccaacgccaa gctgtacatc aacgactaca gcctcgactc | 660 |
| ccagagcgcc tccaaggtca ccaagggtat ggttccctac gtcaagaagt ggctcagcca | 720 |
| gggcgttccc gtcgacggca ttggctctca gactcacctt gaccccggtc aggctcccca | 780 |
| aatccagggt gctctcactg ccctcgccaa ttctggtgtc aaggaggttg ccatcaccga | 840 |
| gctcgacatc cgcactgccc ccgccaacga ctacgctacc gtcaccaagg cctgcctcaa | 900 |
| cgtccccaag tgcattggta tcaccgtctg gggtgtctct gacaagaact cttggcgcaa | 960 |
| ggagcacgac agtcttctgt tcgatgctaa ctacaacccc aagcctgctt actacgctgt | 1020 |
| tgtcaacgct ctccgctaa | 1039 |

```
<210> SEQ ID NO 13
<211> LENGTH: 1039
<212> TYPE: DNA
<213> ORGANISM: Artificial Sequence
<220> FEATURE:
<223> OTHER INFORMATION: Variant GH10 xylanase sequence

<400> SEQUENCE: 13
```

| | |
|---|---|
| atgaagctgt cttctttcct ctacaccgcc tcgctggtcg cggccattcc caccgccatc | 60 |
| gagccccgcc aggctgccga cagcatcgac aagctgatca gaacaaggg caagctctac | 120 |
| tacggaacca tcaccgaccc ccccctgctc ggcgtcgcaa aggacgtcgc catcatcaag | 180 |
| gccgactttg gcgccgttac ccccgagaac tcgggcaagt gggacgccac cgagcccag | 240 |
| cagggcaagt tcaccttcac cagcttcgac caggttgtca actttgccca gcagaatggc | 300 |
| ctctacgtcc gaggtcacac tctggtctgg cactctcagc tccctcagtg ggttaagaac | 360 |
| atcaacgaca aggctatgct gaccaaggtc attgagaacc acgtcaccca actcgttgga | 420 |
| cgctacaagg gcaagatcta cgcctgggta tgttttattc ccccagactt cttcgaaatg | 480 |
| actttgctaa catgttcagg acgtcgtcaa cgagatcttc gagtgggacg gtaccctccg | 540 |
| aaaggactct cacttcaacc aggtcttcgg caacgacgac tacgttggca ttgccttccg | 600 |
| cgccgcccgc aaggctgacc ccaacgccaa gctgtacatc aacgactaca gcctcgactc | 660 |
| ccagagcgcc tccaaggtca ccaagggtat ggttccctac gtcaagaagt ggctcagcca | 720 |
| gggcgttccc gtcgacggca ttggctctca gactcacctt gaccccggtc aggctcccca | 780 |
| aatccagggt gctctcactg ccctcgccaa ttctggtgtc aaggaggttg ccatcaccga | 840 |
| gctcgacatc cgcactgccc ccgccaacga ctacgctacc gtcaccaagg cctgcctcaa | 900 |
| cgtccccaag tgcattggta tcaccgtctg gggtgtctct gacaagaact cttggcgcaa | 960 |
| ggagcacgac agtcttctgt tcgatgctaa ctacaacccc aagcctgctt actacgctgt | 1020 |
| tgtcaacgct ctccgctaa | 1039 |

```
<210> SEQ ID NO 14
<211> LENGTH: 1039
<212> TYPE: DNA
<213> ORGANISM: Artificial Sequence
<220> FEATURE:
<223> OTHER INFORMATION: Variant GH10 xylanase sequence

<400> SEQUENCE: 14
```

| | |
|---|---|
| atgaagctgt cttctttcct ctacaccgcc tcgctggtcg cggccattcc caccgccatc | 60 |
| gagccccgcc aggctgccga cagcatcgac aagctgatca gaacaaggg caagctctac | 120 |

| | |
|---|---|
| tacggaacca tcaccgaccc ccctctgctc ggcgtcgcaa aggacgtcgc catcatcaag | 180 |
| gccgactttg gcgccgttac ccccgagaac tcgggcaagt gggacgccac cgagcccagc | 240 |
| cagggcaagt tcaacttcgg tagcttcgac caggttgtca actttgccca gcagaatggc | 300 |
| ctctacgtcc gaggtcacac tctggtctgg cacggccagc tccctcagtg ggttaagaac | 360 |
| atcaacgaca aggctactct gaccaaggtc attgagaacc acgtcaccca agtcgttgga | 420 |
| cgctacaagg gcaagatcta cgcctgggta tgttttattc ccccagactt cttcgaaatg | 480 |
| actttgctaa catgttcagg acgtcgtcaa cgagatcttc gagtgggacg gtaccctccg | 540 |
| aaaggactct cacttcaaca acgtcttcgg caacgacgac tacgttggca ttgccttccg | 600 |
| cgccgcccgc aaggctgacc ccaacgccaa gctgtacatc aacgactaca gcctcgactc | 660 |
| cggcagcgcc tccaaggtca ccaagggtat ggttccctcc gtcaagaagt ggctcagcca | 720 |
| gggcgttccc gtcgacggca ttggctctca gactcacctt gaccccggtc aggctggcca | 780 |
| aatccagggt gctctcactg ccctcgccaa ttctggtgtc aaggaggttg ccatcaccga | 840 |
| gctcgacatc cgcactgccc ccgccaacga ctacgctacc gtcaccaagg cctgcctcaa | 900 |
| cgtccccaag tgcattggta tcaccgtctg gggtgtctct gacaagaact cttggcgcaa | 960 |
| ggagcacgac agtcttctgt tcgatgctaa ctacaaccc aagcctgctt actacgctgt | 1020 |
| tgtcaacgct ctccgctaa | 1039 |

<210> SEQ ID NO 15
<211> LENGTH: 1039
<212> TYPE: DNA
<213> ORGANISM: Artificial Sequence
<220> FEATURE:
<223> OTHER INFORMATION: Variant GH10 xylanase sequence

<400> SEQUENCE: 15

| | |
|---|---|
| atgaagctgt cttctttcct ctacaccgcc tcgctggtcg cggccattcc caccgccatc | 60 |
| gagccccgcc aggctgccga cagcatcgac aagctgatca gaacaagggg caagctctac | 120 |
| tacggaacca tcaccgaccc caacctgctc ggcgtcgcaa aggacgtcgc catcatcaag | 180 |
| gccgactttg gcgccgttac ccccgagaac tcgggcaagt gggacgccac cgagcccag | 240 |
| cagggcaagt tcaccttcac cagcttcgac caggttgtca actttgccca gcagaatggc | 300 |
| ctctacgtcc gaggtcacac tctggtctgg cacggccagc tccctcagtg ggttaagaac | 360 |
| atcaacgaca aggctactct gaccaaggtc attgagaacc acgtcaccca agtcgttgga | 420 |
| cgctacaagg gcaagatcta cgcctgggta tgttttattc ccccagactt cttcgaaatg | 480 |
| actttgctaa catgttcagg acgtcgtcaa cgagatcttc gagtgggacg gtaccctccg | 540 |
| aaaggactct cacttcaaca acgtcttcgg caacgacgac tacgttggca ttgccttccg | 600 |
| cgccgcccgc aaggctgacc ccaacgccaa gctgtacatc aacgactaca gcctcgactc | 660 |
| cggcagcgcc tccaaggtca ccaagggtat ggttccctcc gtcaagaagt ggctcagcca | 720 |
| gggcgttccc gtcgacggca ttggctctca gactcacctt gaccccggtc aggctggcca | 780 |
| aatccagggt gctctcactg ccctcgccaa ttctggtgtc aaggaggttg ccatcaccga | 840 |
| gctcgacatc cgcactgccc ccgccaacga ctacgctacc gtcaccaagg cctgcctcaa | 900 |
| cgtccccaag tgcattggta tcaccgtctg gggtgtctct gacaagaact cttggcgcaa | 960 |
| ggagcacgac agtcttctgt tcgatgctaa ctacaaccc aagcctgctt actacgctgt | 1020 |
| tgtcaacgct ctccgctaa | 1039 |

<210> SEQ ID NO 16
<211> LENGTH: 1039
<212> TYPE: DNA
<213> ORGANISM: Artificial Sequence
<220> FEATURE:
<223> OTHER INFORMATION: Variant GH10 xylanase sequence

<400> SEQUENCE: 16

```
atgaagctgt cttctttcct ctacaccgcc tcgctggtcg cggccattcc caccgccatc      60
gagccccgcc aggctgccga cagcatcgac aagctgatca agaacaaggg caagctctac     120
tacggaacca tcaccgaccc ccccctgctc ggcgtcgcaa aggacgtcgc catcatcaag     180
gccgactttg gcgccgttac ccccgagaac tcgggcaagt gggacgccac cgagcccagc     240
cagggcaagt tcaacttcac cagcttcgac caggttgtca actttgccca gcagaatggc     300
ctctacgtcc gaggtcacac tctggtctgg cacggccagc ccctcagtg ggttaagaac      360
atcaacgaca aggctactct gaccaaggtc attgagaacc acgtcaccca agtcgttgga     420
cgctacaagg gcaagatcta cgcctgggta tgttttattc ccccagactt cttcgaaatg     480
actttgctaa catgttcagg acgtcgtcaa cgagatcttc gagtgggacg gtaccctccg     540
aaaggactct cacttcaaca acgtcttcgg caacgacgac tacgttggca ttgccttccg     600
cgccgcccgc aaggctgacc ccaacgccaa gctgtacatc aacgactaca gcctcgactc     660
cggcagcgcc tccaaggtca ccaagggtat ggttccctcc gtcaagaagt ggctcagcca     720
gggcgttccc gtcgacggca ttggctctca gactcacctt gaccccggtc aggctggcca     780
aatccagggt gctctcactg ccctcgccaa ttctggtgtc aaggaggttg ccatcaccga     840
gctcgacatc cgcactgccc ccgccaacga ctacgctacc gtcaccaagg cctgcctcaa     900
cgtccccaag tgcattggta tcaccgtctg gggtgtctct gacaagaact cttggcgcaa     960
ggagcacgac agtcttctgt cgatgctaa ctacaacccc aagcctgctt actacgctgt     1020
tgtcaacgct ctccgctaa                                                 1039
```

<210> SEQ ID NO 17
<211> LENGTH: 305
<212> TYPE: PRT
<213> ORGANISM: Artificial Sequence
<220> FEATURE:
<223> OTHER INFORMATION: Variant GH10 xylanase sequence

<400> SEQUENCE: 17

Gln Ala Ala Asp Ser Ile Asp Lys Leu Ile Lys Asn Lys Gly Lys Leu
1               5                   10                  15

Tyr Tyr Gly Thr Ile Thr Asp Pro Pro Leu Leu Gly Val Ala Lys Asp
                20                  25                  30

Val Ala Ile Ile Lys Ala Asp Phe Gly Ala Val Thr Pro Glu Asn Ser
            35                  40                  45

Gly Lys Trp Asp Ala Thr Glu Pro Gln Gln Gly Lys Phe Thr Phe Gly
        50                  55                  60

Ser Phe Asp Gln Val Val Asn Phe Ala Gln Gln Asn Gly Leu Tyr Val
65                  70                  75                  80

Arg Gly His Thr Leu Val Trp His Gly Gln Pro Gln Trp Val Lys
                85                  90                  95

Asn Ile Asn Asp Lys Ala Met Leu Thr Lys Val Ile Glu Asn His Val
            100                 105                 110

Thr Gln Leu Val Gly Arg Tyr Lys Gly Lys Ile Tyr Ala Trp Asp Val
        115                 120                 125

Val Asn Glu Ile Phe Glu Trp Asp Gly Thr Leu Arg Lys Asp Ser His
    130                 135                 140

Phe Asn Gln Val Phe Gly Asn Asp Asp Tyr Val Gly Ile Ala Phe Arg
145                 150                 155                 160

Ala Ala Arg Lys Ala Asp Pro Asn Ala Lys Leu Tyr Ile Asn Asp Tyr
                165                 170                 175

Ser Leu Asp Ser Gln Ser Ala Ser Lys Val Thr Lys Gly Met Val Pro
            180                 185                 190

Tyr Val Lys Lys Trp Leu Ser Gln Gly Val Pro Val Asp Gly Ile Gly
        195                 200                 205

Ser Gln Thr His Leu Asp Pro Gly Gln Ala Pro Gln Ile Gln Gly Ala
    210                 215                 220

Leu Thr Ala Leu Ala Asn Ser Gly Val Lys Glu Val Ala Ile Thr Glu
225                 230                 235                 240

Leu Asp Ile Arg Thr Ala Pro Ala Asn Asp Tyr Ala Thr Val Thr Lys
                245                 250                 255

Ala Cys Leu Asn Val Pro Lys Cys Ile Gly Ile Thr Val Trp Gly Val
            260                 265                 270

Ser Asp Lys Asn Ser Trp Arg Lys Glu His Asp Ser Leu Leu Phe Asp
        275                 280                 285

Ala Asn Tyr Asn Pro Lys Pro Ala Tyr Ala Val Val Asn Ala Leu
    290                 295                 300

Arg
305

<210> SEQ ID NO 18
<211> LENGTH: 305
<212> TYPE: PRT
<213> ORGANISM: Artificial Sequence
<220> FEATURE:
<223> OTHER INFORMATION: Variant GH10 xylanase sequence

<400> SEQUENCE: 18

Gln Ala Ala Asp Ser Ile Asp Lys Leu Ile Lys Asn Lys Gly Lys Leu
1               5                   10                  15

Tyr Tyr Gly Thr Ile Thr Asp Pro Pro Leu Leu Gly Val Ala Lys Asp
                20                  25                  30

Val Ala Ile Ile Lys Ala Asp Phe Gly Ala Val Thr Pro Glu Asn Ser
            35                  40                  45

Gly Lys Trp Asp Ala Thr Glu Pro Gln Gln Gly Lys Phe Thr Phe Thr
        50                  55                  60

Ser Phe Asp Gln Val Val Asn Phe Ala Gln Gln Asn Gly Leu Tyr Val
65                  70                  75                  80

Arg Gly His Thr Leu Val Trp His Ser Gln Leu Pro Gln Trp Val Lys
                85                  90                  95

Asn Ile Asn Asp Lys Ala Met Leu Thr Lys Val Ile Glu Asn His Val
            100                 105                 110

Thr Gln Leu Val Gly Arg Tyr Lys Gly Lys Ile Tyr Ala Trp Asp Val
        115                 120                 125

Val Asn Glu Ile Phe Glu Trp Asp Gly Thr Leu Arg Lys Asp Ser His
    130                 135                 140

Phe Asn Gln Val Phe Gly Asn Asp Asp Tyr Val Gly Ile Ala Phe Arg
145                 150                 155                 160

Ala Ala Arg Lys Ala Asp Pro Asn Ala Lys Leu Tyr Ile Asn Asp Tyr
                165                 170                 175

```
Ser Leu Asp Ser Gln Ser Ala Ser Lys Val Thr Lys Gly Met Val Pro
            180                 185                 190

Tyr Val Lys Lys Trp Leu Ser Gln Gly Val Pro Val Asp Gly Ile Gly
            195                 200                 205

Ser Gln Thr His Leu Asp Pro Gly Gln Ala Pro Gln Ile Gln Gly Ala
            210                 215                 220

Leu Thr Ala Leu Ala Asn Ser Gly Val Lys Glu Val Ala Ile Thr Glu
225                 230                 235                 240

Leu Asp Ile Arg Thr Ala Pro Ala Asn Asp Tyr Ala Thr Val Thr Lys
                245                 250                 255

Ala Cys Leu Asn Val Pro Lys Cys Ile Gly Ile Thr Val Trp Gly Val
            260                 265                 270

Ser Asp Lys Asn Ser Trp Arg Lys Glu His Asp Ser Leu Leu Phe Asp
            275                 280                 285

Ala Asn Tyr Asn Pro Lys Pro Ala Tyr Tyr Ala Val Val Asn Ala Leu
            290                 295                 300

Arg
305

<210> SEQ ID NO 19
<211> LENGTH: 305
<212> TYPE: PRT
<213> ORGANISM: Artificial Sequence
<220> FEATURE:
<223> OTHER INFORMATION: Variant GH10 xylanase sequence

<400> SEQUENCE: 19

Gln Ala Ala Asp Ser Ile Asp Lys Leu Ile Lys Asn Lys Gly Lys Leu
1               5                   10                  15

Tyr Tyr Gly Thr Ile Thr Asp Pro Pro Leu Leu Gly Val Ala Lys Asp
            20                  25                  30

Val Ala Ile Ile Lys Ala Asp Phe Gly Ala Val Thr Pro Glu Asn Ser
            35                  40                  45

Gly Lys Trp Asp Ala Thr Glu Pro Ser Gln Gly Lys Phe Asn Phe Gly
        50                  55                  60

Ser Phe Asp Gln Val Val Asn Phe Ala Gln Gln Asn Gly Leu Tyr Val
65                  70                  75                  80

Arg Gly His Thr Leu Val Trp His Gly Gln Leu Pro Gln Trp Val Lys
                85                  90                  95

Asn Ile Asn Asp Lys Ala Thr Leu Thr Lys Val Ile Glu Asn His Val
            100                 105                 110

Thr Gln Val Val Gly Arg Tyr Lys Gly Lys Ile Tyr Ala Trp Asp Val
            115                 120                 125

Val Asn Glu Ile Phe Glu Trp Asp Gly Thr Leu Arg Lys Asp Ser His
        130                 135                 140

Phe Asn Asn Val Phe Gly Asn Asp Asp Tyr Val Gly Ile Ala Phe Arg
145                 150                 155                 160

Ala Ala Arg Lys Ala Asp Pro Asn Ala Lys Leu Tyr Ile Asn Asp Tyr
                165                 170                 175

Ser Leu Asp Ser Gly Ser Ala Ser Lys Val Thr Lys Gly Met Val Pro
            180                 185                 190

Ser Val Lys Lys Trp Leu Ser Gln Gly Val Pro Val Asp Gly Ile Gly
            195                 200                 205

Ser Gln Thr His Leu Asp Pro Gly Gln Ala Gly Gln Ile Gln Gly Ala
            210                 215                 220
```

```
Leu Thr Ala Leu Ala Asn Ser Gly Val Lys Glu Val Ala Ile Thr Glu
225                 230                 235                 240

Leu Asp Ile Arg Thr Ala Pro Ala Asn Asp Tyr Ala Thr Val Thr Lys
            245                 250                 255

Ala Cys Leu Asn Val Pro Lys Cys Ile Gly Ile Thr Val Trp Gly Val
        260                 265                 270

Ser Asp Lys Asn Ser Trp Arg Lys Glu His Asp Ser Leu Leu Phe Asp
        275                 280                 285

Ala Asn Tyr Asn Pro Lys Pro Ala Tyr Tyr Ala Val Val Asn Ala Leu
        290                 295                 300

Arg
305

<210> SEQ ID NO 20
<211> LENGTH: 305
<212> TYPE: PRT
<213> ORGANISM: Artificial Sequence
<220> FEATURE:
<223> OTHER INFORMATION: Variant GH10 xylanase sequence

<400> SEQUENCE: 20

Gln Ala Ala Asp Ser Ile Asp Lys Leu Ile Lys Asn Lys Gly Lys Leu
1               5                   10                  15

Tyr Tyr Gly Thr Ile Thr Asp Pro Asn Leu Leu Gly Val Ala Lys Asp
            20                  25                  30

Val Ala Ile Ile Lys Ala Asp Phe Gly Ala Val Thr Pro Glu Asn Ser
        35                  40                  45

Gly Lys Trp Asp Ala Thr Glu Pro Gln Gln Gly Lys Phe Thr Phe Thr
    50                  55                  60

Ser Phe Asp Gln Val Val Asn Phe Ala Gln Gln Asn Gly Leu Tyr Val
65                  70                  75                  80

Arg Gly His Thr Leu Val Trp His Gly Gln Leu Pro Gln Trp Val Lys
                85                  90                  95

Asn Ile Asn Asp Lys Ala Thr Leu Thr Lys Val Ile Glu Asn His Val
            100                 105                 110

Thr Gln Val Val Gly Arg Tyr Lys Gly Lys Ile Tyr Ala Trp Asp Val
        115                 120                 125

Val Asn Glu Ile Phe Glu Trp Asp Gly Thr Leu Arg Lys Asp Ser His
    130                 135                 140

Phe Asn Asn Val Phe Gly Asn Asp Asp Tyr Val Gly Ile Ala Phe Arg
145                 150                 155                 160

Ala Ala Arg Lys Ala Asp Pro Asn Ala Lys Leu Tyr Ile Asn Asp Tyr
                165                 170                 175

Ser Leu Asp Ser Gly Ser Ala Ser Lys Val Thr Lys Gly Met Val Pro
            180                 185                 190

Ser Val Lys Lys Trp Leu Ser Gln Gly Val Pro Val Asp Gly Ile Gly
        195                 200                 205

Ser Gln Thr His Leu Asp Pro Gly Gln Ala Gly Gln Ile Gln Gly Ala
    210                 215                 220

Leu Thr Ala Leu Ala Asn Ser Gly Val Lys Glu Val Ala Ile Thr Glu
225                 230                 235                 240

Leu Asp Ile Arg Thr Ala Pro Ala Asn Asp Tyr Ala Thr Val Thr Lys
                245                 250                 255

Ala Cys Leu Asn Val Pro Lys Cys Ile Gly Ile Thr Val Trp Gly Val
            260                 265                 270
```

Ser Asp Lys Asn Ser Trp Arg Lys Glu His Asp Ser Leu Leu Phe Asp
    275                 280                 285

Ala Asn Tyr Asn Pro Lys Pro Ala Tyr Tyr Ala Val Val Asn Ala Leu
290                 295                 300

Arg
305

<210> SEQ ID NO 21
<211> LENGTH: 305
<212> TYPE: PRT
<213> ORGANISM: Artificial Sequence
<220> FEATURE:
<223> OTHER INFORMATION: Variant GH10 xylanase sequence

<400> SEQUENCE: 21

Gln Ala Ala Asp Ser Ile Asp Lys Leu Ile Lys Asn Lys Gly Lys Leu
1               5                   10                  15

Tyr Tyr Gly Thr Ile Thr Asp Pro Pro Leu Leu Gly Val Ala Lys Asp
            20                  25                  30

Val Ala Ile Ile Lys Ala Asp Phe Gly Ala Val Thr Pro Glu Asn Ser
        35                  40                  45

Gly Lys Trp Asp Ala Thr Glu Pro Ser Gln Gly Lys Phe Asn Phe Thr
    50                  55                  60

Ser Phe Asp Gln Val Val Asn Phe Ala Gln Gln Asn Gly Leu Tyr Val
65                  70                  75                  80

Arg Gly His Thr Leu Val Trp His Gly Gln Leu Pro Gln Trp Val Lys
                85                  90                  95

Asn Ile Asn Asp Lys Ala Thr Leu Thr Lys Val Ile Glu Asn His Val
            100                 105                 110

Thr Gln Val Val Gly Arg Tyr Lys Gly Lys Ile Tyr Ala Trp Asp Val
        115                 120                 125

Val Asn Glu Ile Phe Glu Trp Asp Gly Thr Leu Arg Lys Asp Ser His
    130                 135                 140

Phe Asn Asn Val Phe Gly Asn Asp Tyr Val Gly Ile Ala Phe Arg
145                 150                 155                 160

Ala Ala Arg Lys Ala Asp Pro Asn Ala Lys Leu Tyr Ile Asn Asp Tyr
                165                 170                 175

Ser Leu Asp Ser Gly Ser Ala Ser Lys Val Thr Lys Gly Met Val Pro
            180                 185                 190

Ser Val Lys Lys Trp Leu Ser Gln Gly Val Pro Val Asp Gly Ile Gly
        195                 200                 205

Ser Gln Thr His Leu Asp Pro Gly Gln Ala Gly Gln Ile Gln Gly Ala
    210                 215                 220

Leu Thr Ala Leu Ala Asn Ser Gly Val Lys Glu Val Ala Ile Thr Glu
225                 230                 235                 240

Leu Asp Ile Arg Thr Ala Pro Ala Asn Asp Tyr Ala Thr Val Thr Lys
                245                 250                 255

Ala Cys Leu Asn Val Pro Lys Cys Ile Gly Ile Thr Val Trp Gly Val
            260                 265                 270

Ser Asp Lys Asn Ser Trp Arg Lys Glu His Asp Ser Leu Leu Phe Asp
        275                 280                 285

Ala Asn Tyr Asn Pro Lys Pro Ala Tyr Tyr Ala Val Val Asn Ala Leu
    290                 295                 300

Arg
305

<210> SEQ ID NO 22
<211> LENGTH: 27
<212> TYPE: DNA
<213> ORGANISM: Artificial Sequence
<220> FEATURE:
<223> OTHER INFORMATION: Primer 1

<400> SEQUENCE: 22
caccatgaag ctgtcttctt tcctcta                                          27

<210> SEQ ID NO 23
<211> LENGTH: 27
<212> TYPE: DNA
<213> ORGANISM: Artificial Sequence
<220> FEATURE:
<223> OTHER INFORMATION: Primer 2

<400> SEQUENCE: 23
tttttagcgg agagcgttga caacagc                                          27

<210> SEQ ID NO 24
<211> LENGTH: 1039
<212> TYPE: DNA
<213> ORGANISM: Fusarium verticillioides

<400> SEQUENCE: 24
atgaagctgt cttctttcct ctacaccgcc tcgctggtcg cggccattcc caccgccatc      60
gagccccgcc aggctgccga cagcatcaac aagctgatca agaacaaggg caagctctac 120
tacggaacca tcaccgaccc caacctgctc ggcgtcgcaa aggacaccgc catcatcaag 180
gccgactttg gcgccgttac ccccgagaac tcgggcaagt gggacgccac cgagcccagc 240
cagggcaagt tcaacttcgg tagcttcgac caggttgtca actttgccca gcagaatggc 300
ctcaaggtcc gaggtcacac tctggtctgg cactctcagc tccctcagtg ggttaagaac 360
atcaacgaca aggctactct gaccaaggtc attgagaacc acgtcaccca agtcgttgga 420
cgctacaagg gcaagatcta cgcctgggta tgttttattc cccagactt cttcgaaatg 480 actttgctaa catgttcagg acgtcgtcaa cgagatcttc gagtgggacg gtaccctccg 540
aaaggactct cacttcaaca acgtcttcgg caacgacgac tacgttggca ttgccttccg 600
cgccgcccgc aaggctgacc ccaacgccaa gctgtacatc aacgactaca gcctcgactc 660
cggcagcgcc tccaaggtca ccaagggtat ggttccctcc gtcaagaagt ggctcagcca 720
gggcgttccc gtcgacggca ttggctctca gactcacctt gaccccggtg ccgctggcca 780
aatccagggt gctctcactg ccctcgccaa ttctggtgtc aaggaggttg ccatcaccga 840
gctcgacatc cgcactgccc ccgccaacga ctacgctacc gtcaccaagg cctgcctcaa 900
cgtccccaag tgcattggta tcaccgtctg gggtgtctct gacaagaact cttggcgcaa 960
ggagcacgac agtcttctgt tcgatgctaa ctacaacccc aagcctgctt acactgctgt 1020
tgtcaacgct ctccgctaa 1039

<210> SEQ ID NO 25
<211> LENGTH: 1039
<212> TYPE: DNA
<213> ORGANISM: Fusarium verticillioides

<400> SEQUENCE: 25
atgaagctgt cttctttcct ctacaccgcc tcgctggtcg cggccattcc caccgccatc 60

```
gagccccgcc aggctgccga cagcatcaac aagctgatca agaacaaggg caagctctac      120
tacggaacca tcaccgaccc caacctgctc ggcgtcgcaa aggacaccgc catcatcaag      180
gccgactttg gcgccgttac ccccgagaac tcgggcaagt gggacgccac cgagcccagc      240
cagggcaagt tcaacttcgg tagcttcgac caggttgtca actttgccca gcagaatggc      300
ctcaaggtcc gaggtcacac tctggtctgg cactctcagc ccctcagtg ggttaagaac       360 atcaacgaca aggctactct gaccaaggtc attgagaacc acgtcaccca agtcgttgga      420
cgctacaagg gcaagatcta cgcctgggta tgttttattc ccccagactt cttcgaaatg      480
actttgctaa catgttcagg acgtcgtcaa cgagatcttc gagtgggacg gtaccctccg      540
aaaggactct cacttcaaca acgtcttcgg caacgacgac tacgttggca ttgccttccg      600
cgccgcccgc aaggctgacc ccaacgccaa gctgtacatc aacgactaca gcctcgactc      660
cggcagcgcc tccaaggtca ccaagggtat ggttccctcc gtcaagaagt ggctcagcca      720
gggcgttccc gtcgacggca ttggctctca gactcacctt gaccccggtg ccgctggcca      780
aatccagggt gctctcactg ccctcgccaa ttctggtgtc aaggaggttg ccatcaccga      840
gctcgacatc cgcactgccc ccgccaacga ctacgctacc gtcaccaagg cctgcctcaa      900
cgtccccaag tgcattggta tcaccgtctg gggtgtctct gacaagaact cttggcgcaa      960
ggagcacgac agtcttctgt tcgatgctaa ctacaacccc aagcctgctt acactgctgt     1020
tgtcaacgct ctccgctaa                                                  1039
```

<210> SEQ ID NO 26
<211> LENGTH: 328
<212> TYPE: PRT
<213> ORGANISM: Fusarium verticillioides

<400> SEQUENCE: 26

```
Met Lys Leu Ser Ser Phe Leu Tyr Thr Ala Ser Leu Val Ala Ala Ile
1               5                   10                  15

Pro Thr Ala Ile Glu Pro Arg Gln Ala Ala Asp Ser Ile Asn Lys Leu
            20                  25                  30

Ile Lys Asn Lys Gly Lys Leu Tyr Tyr Gly Thr Ile Thr Asp Pro Asn
        35                  40                  45

Leu Leu Gly Val Ala Lys Asp Thr Ala Ile Ile Lys Ala Asp Phe Gly
    50                  55                  60

Ala Val Thr Pro Glu Asn Ser Gly Lys Trp Asp Ala Thr Glu Pro Ser
65                  70                  75                  80

Gln Gly Lys Phe Asn Phe Gly Ser Phe Asp Gln Val Val Asn Phe Ala
                85                  90                  95

Gln Gln Asn Gly Leu Lys Val Arg Gly His Thr Leu Val Trp His Ser
            100                 105                 110

Gln Leu Pro Gln Trp Val Lys Asn Ile Asn Asp Lys Ala Thr Leu Thr
        115                 120                 125

Lys Val Ile Glu Asn His Val Thr Gln Val Val Gly Arg Tyr Lys Gly
    130                 135                 140

Lys Ile Tyr Ala Trp Asp Val Val Asn Glu Ile Phe Glu Trp Asp Gly
145                 150                 155                 160

Thr Leu Arg Lys Asp Ser His Phe Asn Asn Val Phe Gly Asn Asp Asp
                165                 170                 175

Tyr Val Gly Ile Ala Phe Arg Ala Ala Arg Lys Ala Asp Pro Asn Ala
            180                 185                 190

Lys Leu Tyr Ile Asn Asp Tyr Ser Leu Asp Ser Gly Ser Ala Ser Lys
```

```
            195                 200                 205
Val Thr Lys Gly Met Val Pro Ser Val Lys Lys Trp Leu Ser Gln Gly
210                 215                 220

Val Pro Val Asp Gly Ile Gly Ser Gln Thr His Leu Asp Pro Gly Ala
225                 230                 235                 240

Ala Gly Gln Ile Gln Gly Ala Leu Thr Ala Leu Ala Asn Ser Gly Val
                245                 250                 255

Lys Glu Val Ala Ile Thr Glu Leu Asp Ile Arg Thr Ala Pro Ala Asn
                260                 265                 270

Asp Tyr Ala Thr Val Thr Lys Ala Cys Leu Asn Val Pro Lys Cys Ile
            275                 280                 285

Gly Ile Thr Val Trp Gly Val Ser Asp Lys Asn Ser Trp Arg Lys Glu
            290                 295                 300

His Asp Ser Leu Leu Phe Asp Ala Asn Tyr Asn Pro Lys Pro Ala Tyr
305                 310                 315                 320

Thr Ala Val Val Asn Ala Leu Arg
                325

<210> SEQ ID NO 27
<211> LENGTH: 313
<212> TYPE: PRT
<213> ORGANISM: Fusarium verticillioides

<400> SEQUENCE: 27

Ile Pro Thr Ala Ile Glu Pro Arg Gln Ala Ala Asp Ser Ile Asn Lys
1               5                   10                  15

Leu Ile Lys Asn Lys Gly Lys Leu Tyr Tyr Gly Thr Ile Thr Asp Pro
            20                  25                  30

Asn Leu Leu Gly Val Ala Lys Asp Thr Ala Ile Ile Lys Ala Asp Phe
        35                  40                  45

Gly Ala Val Thr Pro Glu Asn Ser Gly Lys Trp Asp Ala Thr Glu Pro
50                  55                  60

Ser Gln Gly Lys Phe Asn Phe Gly Ser Phe Asp Gln Val Val Asn Phe
65                  70                  75                  80

Ala Gln Gln Asn Gly Leu Lys Val Arg Gly His Thr Leu Val Trp His
                85                  90                  95

Ser Gln Leu Pro Gln Trp Val Lys Asn Ile Asn Asp Lys Ala Thr Leu
            100                 105                 110

Thr Lys Val Ile Glu Asn His Val Thr Gln Val Val Gly Arg Tyr Lys
        115                 120                 125

Gly Lys Ile Tyr Ala Trp Asp Val Val Asn Glu Ile Phe Glu Trp Asp
130                 135                 140

Gly Thr Leu Arg Lys Asp Ser His Phe Asn Asn Val Phe Gly Asn Asp
145                 150                 155                 160

Asp Tyr Val Gly Ile Ala Phe Arg Ala Ala Arg Lys Ala Asp Pro Asn
                165                 170                 175

Ala Lys Leu Tyr Ile Asn Asp Tyr Ser Leu Asp Ser Gly Ser Ala Ser
            180                 185                 190

Lys Val Thr Lys Gly Met Val Pro Ser Val Lys Lys Trp Leu Ser Gln
        195                 200                 205

Gly Val Pro Val Asp Gly Ile Gly Ser Gln Thr His Leu Asp Pro Gly
210                 215                 220

Ala Ala Gly Gln Ile Gln Gly Ala Leu Thr Ala Leu Ala Asn Ser Gly
225                 230                 235                 240
```

```
Val Lys Glu Val Ala Ile Thr Glu Leu Asp Ile Arg Thr Ala Pro Ala
            245                 250                 255

Asn Asp Tyr Ala Thr Val Thr Lys Ala Cys Leu Asn Val Pro Lys Cys
        260                 265                 270

Ile Gly Ile Thr Val Trp Gly Val Ser Asp Lys Asn Ser Trp Arg Lys
        275                 280                 285

Glu His Asp Ser Leu Leu Phe Asp Ala Asn Tyr Asn Pro Lys Pro Ala
    290                 295                 300

Tyr Thr Ala Val Val Asn Ala Leu Arg
305                 310

<210> SEQ ID NO 28
<211> LENGTH: 328
<212> TYPE: PRT
<213> ORGANISM: Fusarium oxysporum

<400> SEQUENCE: 28

Met Lys Leu Ser Ser Phe Leu Tyr Thr Ala Ser Leu Val Ala Ala Ile
1               5                   10                  15

Pro Thr Ala Ile Glu Pro Arg Gln Ala Ser Asp Ser Ile Asn Lys Leu
            20                  25                  30

Ile Lys Asn Lys Gly Lys Leu Tyr Tyr Gly Thr Ile Thr Asp Pro Asn
        35                  40                  45

Leu Leu Gly Val Ala Lys Asp Thr Ala Ile Ile Lys Ala Asp Phe Gly
    50                  55                  60

Ala Val Thr Pro Glu Asn Ser Gly Lys Trp Asp Ala Thr Glu Pro Ser
65                  70                  75                  80

Gln Gly Lys Phe Asn Phe Gly Ser Phe Asp Gln Val Val Asn Phe Ala
                85                  90                  95

Gln Gln Asn Gly Leu Lys Val Arg Gly His Thr Leu Val Trp His Ser
            100                 105                 110

Gln Leu Pro Gln Trp Val Lys Asn Ile Asn Asp Lys Ala Thr Leu Thr
        115                 120                 125

Lys Val Ile Glu Asn His Val Thr Asn Val Val Gly Arg Tyr Lys Gly
    130                 135                 140

Lys Ile Tyr Ala Trp Asp Val Val Asn Glu Ile Phe Asp Trp Asp Gly
145                 150                 155                 160

Thr Leu Arg Lys Asp Ser His Phe Asn Asn Val Phe Gly Asn Asp Asp
                165                 170                 175

Tyr Val Gly Ile Ala Phe Arg Ala Ala Arg Lys Ala Asp Pro Asn Ala
            180                 185                 190

Lys Leu Tyr Ile Asn Asp Tyr Ser Leu Asp Ser Gly Ser Ala Ser Lys
        195                 200                 205

Val Thr Lys Gly Met Val Pro Ser Val Lys Lys Trp Leu Ser Gln Gly
    210                 215                 220

Val Pro Val Asp Gly Ile Gly Ser Gln Thr His Leu Asp Pro Gly Ala
225                 230                 235                 240

Ala Gly Gln Ile Gln Gly Ala Leu Thr Ala Leu Ala Asn Ser Gly Val
                245                 250                 255

Lys Glu Val Ala Ile Thr Glu Leu Asp Ile Arg Thr Ala Pro Ala Asn
            260                 265                 270

Asp Tyr Ala Thr Val Thr Lys Ala Cys Leu Asn Val Pro Lys Cys Ile
        275                 280                 285

Gly Ile Thr Val Trp Gly Val Ser Asp Lys Asn Ser Trp Arg Lys Glu
    290                 295                 300
```

```
His Asp Ser Leu Leu Phe Asp Ala Asn Tyr Asn Pro Lys Ala Ala Tyr
305                 310                 315                 320

Thr Ala Val Val Asn Ala Leu Arg
                325

<210> SEQ ID NO 29
<211> LENGTH: 313
<212> TYPE: PRT
<213> ORGANISM: Fusarium oxysporum

<400> SEQUENCE: 29

Ile Pro Thr Ala Ile Glu Pro Arg Gln Ala Ser Asp Ser Ile Asn Lys
1               5                   10                  15

Leu Ile Lys Asn Lys Gly Lys Leu Tyr Tyr Gly Thr Ile Thr Asp Pro
            20                  25                  30

Asn Leu Leu Gly Val Ala Lys Asp Thr Ala Ile Ile Lys Ala Asp Phe
        35                  40                  45

Gly Ala Val Thr Pro Glu Asn Ser Gly Lys Trp Asp Ala Thr Glu Pro
    50                  55                  60

Ser Gln Gly Lys Phe Asn Phe Gly Ser Phe Asp Gln Val Val Asn Phe
65                  70                  75                  80

Ala Gln Gln Asn Gly Leu Lys Val Arg Gly His Thr Leu Val Trp His
                85                  90                  95

Ser Gln Leu Pro Gln Trp Val Lys Asn Ile Asn Asp Lys Ala Thr Leu
            100                 105                 110

Thr Lys Val Ile Glu Asn His Val Thr Asn Val Val Gly Arg Tyr Lys
        115                 120                 125

Gly Lys Ile Tyr Ala Trp Asp Val Val Asn Glu Ile Phe Asp Trp Asp
    130                 135                 140

Gly Thr Leu Arg Lys Asp Ser His Phe Asn Asn Val Phe Gly Asn Asp
145                 150                 155                 160

Asp Tyr Val Gly Ile Ala Phe Arg Ala Ala Arg Lys Ala Asp Pro Asn
                165                 170                 175

Ala Lys Leu Tyr Ile Asn Asp Tyr Ser Leu Asp Ser Gly Ser Ala Ser
            180                 185                 190

Lys Val Thr Lys Gly Met Val Pro Ser Val Lys Lys Trp Leu Ser Gln
        195                 200                 205

Gly Val Pro Val Asp Gly Ile Gly Ser Gln Thr His Leu Asp Pro Gly
    210                 215                 220

Ala Ala Gly Gln Ile Gln Gly Ala Leu Thr Ala Leu Ala Asn Ser Gly
225                 230                 235                 240

Val Lys Glu Val Ala Ile Thr Glu Leu Asp Ile Arg Thr Ala Pro Ala
                245                 250                 255

Asn Asp Tyr Ala Thr Val Thr Lys Ala Cys Leu Asn Val Pro Lys Cys
            260                 265                 270

Ile Gly Ile Thr Val Trp Gly Val Ser Asp Lys Asn Ser Trp Arg Lys
        275                 280                 285

Glu His Asp Ser Leu Leu Phe Asp Ala Asn Tyr Asn Pro Lys Ala Ala
    290                 295                 300

Tyr Thr Ala Val Val Asn Ala Leu Arg
305                 310

<210> SEQ ID NO 30
<211> LENGTH: 1039
<212> TYPE: DNA
```

<213> ORGANISM: Fusarium oxysporum

<400> SEQUENCE: 30

```
atgaagctgt cttccttcct ctacaccgcc tcgctggtcg cggccattcc caccgccatc      60
gagccccgcc aggcctccga cagcatcaac aagctgatca agaacaaggg caagctctac     120
tacggaacca tcaccgaccc caacctgctc ggcgtcgcaa aggacactgc catcatcaag     180
gctgactttg gcgccgtcac acccgagaac tcgggtaagt gggatgccac cgagcccagc     240
cagggcaagt tcaacttcgg cagcttcgac caggtcgtca ctttgctcca gcagaatggc     300
ctcaaggtcc gaggtcacac tctagtctgg cactcccagc tccctcagtg ggttaagaac     360
atcaacgaca aggctacttt gaccaaggtc atcgagaacc acgtcaccaa cgtcgttgga     420
cgctacaagg gcaagatcta cgcctgggta tgttttcttc actcgaactt cttataaatg     480
gctttactaa catgttcagg acgtcgttaa cgagatcttc gactgggatg gtaccctccg     540
aaaggactct cacttcaaca acgtcttcgg caacgacgac tacgttggca ttgccttccg     600
cgctgcccgc aaggctgacc ccaacgccaa gctgtacatc aacgactaca gcctcgactc     660
cggcagcgcc tccaaggtca ccaagggcat ggttccctct gtcaagaagt ggctcagcca     720
gggcgtcccc gtcgacggta ttggttctca gactcacctt gaccccggtg ccgctggcca     780
aatccagggt gctctcactg ccctcgccaa ctctggtgtg aaggaggttg ccatcaccga     840
gctcgacatc cgcactgccc ccgccaacga ctacgctacc gttaccaagg cctgcctcaa     900
cgtccccaag tgcattggta tcaccgtctg gggcgtatct gacaagaact cttggcgcaa     960
ggagcacgac agccttctgt tcgatgctaa ctacaacccc aaggctgctt acactgctgt    1020
tgtcaacgct ctccgctaa                                                1039
```

<210> SEQ ID NO 31
<211> LENGTH: 987
<212> TYPE: DNA
<213> ORGANISM: Fusarium oxysporum

<400> SEQUENCE: 31

```
atgaagctgt cttccttcct ctacaccgcc tcgctggtcg cggccattcc caccgccatc      60
gagccccgcc aggcctccga cagcatcaac aagctgatca agaacaaggg caagctctac     120
tacggaacca tcaccgaccc caacctgctc ggcgtcgcaa aggacactgc catcatcaag     180
gctgactttg gcgccgtcac acccgagaac tcgggtaagt gggatgccac cgagcccagc     240
cagggcaagt tcaacttcgg cagcttcgac caggtcgtca ctttgctcca gcagaatggc     300
ctcaaggtcc gaggtcacac tctagtctgg cactcccagc tccctcagtg ggttaagaac     360
atcaacgaca aggctacttt gaccaaggtc atcgagaacc acgtcaccaa cgtcgttgga     420
cgctacaagg gcaagatcta cgcctgggac gtcgttaacg agatcttcga ctgggatggt     480
accctccgaa aggactctca cttcaacaac gtcttcggca acgacgacta cgttggcatt     540
gccttccgcg ctgcccgcaa ggctgacccc aacgccaagc tgtacatcaa cgactacagc     600
ctcgactccg gcagcgcctc caaggtcacc aagggcatgt tccctctgt caagaagtgg     660
ctcagccagg gcgtccccgt cgacggtatt ggttctcaga ctcaccttga ccccggtgcc     720
gctggccaaa tccagggtgc tctcactgcc ctcgccaact ctggtgtgaa ggaggttgcc     780
atcaccgagc tcgacatccg cactgccccc gccaacgact acgctaccgt taccaaggcc     840
tgcctcaacg tccccaagtg cattggtatc accgtctggg gcgtatctga caagaactct     900
```

```
tggcgcaagg agcacgacag ccttctgttc gatgctaact acaaccccaa ggctgcttac    960
actgctgttg tcaacgctct ccgctaa                                        987
```

<210> SEQ ID NO 32
<211> LENGTH: 1039
<212> TYPE: DNA
<213> ORGANISM: Fusarium sp.

<400> SEQUENCE: 32

```
atgaagctgt cttctttcct ctacaccgcc tcgctggtcg cggccattcc caccgccatc     60
gagccccgcc aggccgccga cagcatcaac aagctgatca agaacaaggg caagctctac    120
tacggaacca tcaccgaccc caacctgctc ggcgtcgcaa aggacaccgc cgtcatcaag    180
gccgactttg gcgccgtcac ccccgagaac tcgggcaagt gggacgccac cgagcccagc    240
cagggcaact tcaacttcgg tagcttcgac caggtcgtca ctttgctcag cagaatggc    300 ctcaaggtcc gaggtcacac tctggtctgg cactctcagc tccctcagtg ggttaagaac    360
atcaacgaca aggctactct gaccaaggtc attgagaacc acgtcaccca gtcgttgga    420 cgctacaagg gcaagatcta cgcctgggta tgttttcttg cctcgacctt ctcaaagatg    480
aatttgctaa catgttcagg acgttgtcaa cgagatcttc gactgggacg gtaccctccg    540
aaaggattct cacttcaaca acgtcttcgg caacgatgac tacgttggca ttgccttccg    600
cgccgcccgc aaggctgacc ccaacgccaa gctgtacatc aacgactaca gcctcgactc    660
cgccagcgcc tccaaggtca ccaagggcat ggtcccctcc gtcaagaagt ggctcagcca    720
gggcgttccc gtcgacggca ttggctccca gtctcaccttt gaccccggtg ccgctggcca    780
agtccagggt gctctcactg ccctcgccaa ctctggtgtc aaggaggttg ccatcaccga    840
gctcgacatc cgcactgccc ccgccaacga ctacgccacc gtcaccaagg cctgcctaaa    900
cgtccccaag tgcattggta tcaccgtctg gggtgtctct gacaagaact cttggcgcaa    960
ggagcacgac agccttctgt tcgactccaa ctacaacccc aagcctgctt acactgctgt    1020
tgtcaacgct ctccgctaa                                                1039
```

<210> SEQ ID NO 33
<211> LENGTH: 987
<212> TYPE: DNA
<213> ORGANISM: Fusarium sp.

<400> SEQUENCE: 33

```
atgaagctgt cttctttcct ctacaccgcc tcgctggtcg cggccattcc caccgccatc     60
gagccccgcc aggccgccga cagcatcaac aagctgatca agaacaaggg caagctctac    120
tacggaacca tcaccgaccc caacctgctc ggcgtcgcaa aggacaccgc cgtcatcaag    180
gccgactttg gcgccgtcac ccccgagaac tcgggcaagt gggacgccac cgagcccagc    240
cagggcaact tcaacttcgg tagcttcgac caggtcgtca ctttgctcag cagaatggc    300 ctcaaggtcc gaggtcacac tctggtctgg cactctcagc tccctcagtg ggttaagaac    360
atcaacgaca aggctactct gaccaaggtc attgagaacc acgtcaccca gtcgttgga    420 cgctacaagg gcaagatcta cgcctgggac gttgtcaacg atcttcga ctgggacggt    480 accctccgaa aggattctca cttcaacaac gtcttcggca acgatgacta cgttggcatt    540
gccttccgcg ccgcccgcaa ggctgacccc aacgccaagc tgtacatcaa cgactacagc    600
ctcgactccg ccagcgcctc caaggtcacc aagggcatgg tcccctccgt caagaagtgg    660
ctcagccagg gcgttcccgt cgacggcatt ggctcccagt ctcaccttga ccccggtgcc    720
```

```
gctggccaag tccagggtgc tctcactgcc ctcgccaact ctggtgtcaa ggaggttgcc      780
atcaccgagc tcgacatccg cactgccccc gccaacgact acgccaccgt caccaaggcc      840
tgcctaaacg tccccaagtg cattggtatc accgtctggg gtgtctctga caagaactct      900
tggcgcaagg agcacgacag ccttctgttc gactccaact acaacccccaa gcctgcttac     960 actgctgttg tcaacgctct ccgctaa                                           987

<210> SEQ ID NO 34
<211> LENGTH: 40
<212> TYPE: DNA
<213> ORGANISM: Artificial Sequence
<220> FEATURE:
<223> OTHER INFORMATION: Primer 1

<400> SEQUENCE: 34
ccgcggccgc accatgaagc tgtcttcctt cctctacacc                             40

<210> SEQ ID NO 35
<211> LENGTH: 37
<212> TYPE: DNA
<213> ORGANISM: Artificial Sequence
<220> FEATURE:
<223> OTHER INFORMATION: Primer 2

<400> SEQUENCE: 35
ccggcgcgcc cttattagcg gagagcgttg acaacag                                37
```

GH10 FAMILY XYLANASE

FIELD OF THE INVENTION

The present invention relates to novel xylanases which are thermostable and the use of said xylanases in applications, including in feedstuffs, in brewing or malting, in the treatment of arabinoxylan containing raw materials like grain-based materials, e.g. in the production of biofuel or other fermentation products, including biochemicals (e.g. bio-based isoprene), and/or in the wheat gluten-starch separation industry, and methods using these xylanases, as well as compositions (such as feed additive compositions) comprising said xylanases.

BACKGROUND OF THE INVENTION

For many years, endo-β-1,4-xylanases (EC 3.2.1.8) (referred to herein as xylanases) have been used for the modification of complex carbohydrates derived from plant cell wall material. It is well known in the art that the functionality of different xylanases (derived from different microorganisms or plants) differs enormously. Xylanase is the name given to a class of enzymes which degrade the linear polysaccharide beta-1,4-xylan into xylooligosaccharides or xylose, thus breaking down hemicellulose, one of the major components of plant cell walls.

Based on structural and genetic information, xylanases have been classified into different Glycoside Hydrolase (GH) families (Henrissat, (1991) *Biochem. J.* 280, 309-316). Initially all known and characterized xylanases belonged to the families GH10 or GH11. Further work then identified numerous other types of xylanases belonging to the families GH5, GH7, GH8 and GH43 (Collins et al (2005) *FEMS Microbiol Rev.*, 29 (1), 3-23).

Until now the GH11 family differs from all other GH's, being the only family solely consisting of xylan specific xylanases. The structure of the GH11 xylanases can be described as a β-Jelly roll structure or an all β-strand sandwich fold structure (Himmel et al 1997 Appl. Biochem. Biotechnol. 63-65, 315-325). GH11 enzymes have a catalytic domain of around 20 kDa.

GH10 xylanases have a catalytic domain with molecular weights in the range of 32-39 kDa. The structure of the catalytic domain of GH10 xylanases consists of an eightfold β/α barrel (Harris et al 1996—Acta. Crystallog. Sec. D 52, 393-401).

Three-dimensional structures are available for a large number of Family GH10 enzymes, the first solved being those of the *Streptomyces lividans* xylanase A (Derewenda et al J Biol Chem 1994 Aug. 19; 269(33) 20811-4), the *C. fimi* endo-glycanase Cex (White et al Biochemistry 1994 Oct. 25; 33(42) 12546-52), and the *Cellvibrio japonicus* Xyn10A (previously *Pseudomonas fluorescens* subsp. xylanase A) (Harris et al Structure 1994 Nov. 15; 2(11) 1107-16.). As members of Clan GHA they have a classical $(\alpha/\beta)_8$ TIM barrel fold with the two key active site glutamic acids located at the C-terminal ends of beta-strands 4 (acid/base) and 7 (nucleophile) (Henrissat et al Proc Natl Acad Sci USA 1995 Jul. 18; 92(15) 7090-4).

Comprehensive studies characterising the functionality of xylanases have been done on well characterised and pure substrates (Kormelink et al., 1992 Characterisation and mode of action of xylanases and some accessory enzymes. Ph.D. Thesis, Agricultural University Wageningen, Holland (175 pp., English and Dutch summaries)). These studies show that different xylanases have different specific requirements with respect to substitution of the xylose backbone of the arabinoxylan (AX). Some xylanases require three un-substituted xylose residues to hydrolyse the xylose backbone; others require only one or two. The reasons for these differences in specificity are thought to be due to the three dimensional structure within the catalytic domains, which in turn is dependent on the primary structure of the xylanase, i.e. the amino acid sequence. However, the translation of these differences in the amino acid sequences into differences in the functionality of the xylanases, has up until now not been documented when the xylanase acts in a complex environment, such as a plant material, e.g. in a feedstuff.

The xylanase substrates in plant material, e.g. in wheat, have traditionally been divided into two fractions: The water un-extractable AX (WU-AX) and the water extractable AX (WE-AX). There have been numerous explanations as to why there are two different fractions of AX. The older literature (D'Appolonia and MacArthur—(1976, Cereal Chem. 53. 711-718) and Montgomery and Smith (1955, J. Am. Chem. Soc. 77. 3325-332) describes quite high differences in the substitution degree between WE-AX and WU-AX. The highest degree of substitution was found in WE-AX. This was used to explain why some of the AX was extractable. The high degree of substitution made the polymer soluble, compared to a lower substitution degree, which would cause hydrogen bonding between polymers and consequently precipitation.

The difference between the functionality of different xylanases has been thought to be due to differences in xylanase specificity and thereby their preference for the WU-AX or the WE-AX substrates.

Xylanase enzymes have been reported from nearly 100 different organisms, including plants, fungi and bacteria. The xylanase enzymes are classified into several of the more than 40 families of glycosyl hydrolase enzymes. The glycosyl hydrolase enzymes, which include xylanases, mannanases, amylases, β-glucanases, cellulases, and other carbohydrases, are classified based on such properties as the sequence of amino acids, their three dimensional structure and the geometry of their catalytic site (Gilkes, et al., 1991, Microbiol. Reviews 55: 303-315).

BRIEF DESCRIPTION OF THE DRAWINGS

FIG. 1A shows a polypeptide sequence (SEQ ID No. 26) of a xylanase of the present invention (FveXyn4). Underlined (lower case) portion of the sequence reflects an N terminal signal peptide can be cleaved before the enzyme is matured. The amino acids shown in bold and italicized may also be cleaved by post-translational modification before the enzyme is fully matured. In some embodiments this sequence may be the backbone sequence.

FIG. 1B shows a polypeptide sequence (SEQ ID No. 27) of a xylanase of the present invention (FveXyn4). The amino acids shown in bold and italicized may also be cleaved by post-translational modification before the enzyme is fully matured. In some embodiments this sequence may be the backbone sequence.

FIG. 1C shows a polypeptide sequence (SEQ ID No. 1) of a xylanase referred to herein as FveXyn4. This is the active form of the enzyme. This may be referred to herein as the mature form of the enzyme (in some embodiments this sequence a backbone sequence).

FIG. 2A shows a nucleotide sequence (SEQ ID No. 24) encoding a xylanase of the present invention (FveXyn4). The lower case nucleotides which are in bold show the intron sequence. The sequence that encodes the signal sequence is shown bold (upper case).

FIG. 2B shows a nucleotide sequence (SEQ ID No. 25) encoding a xylanase of the present invention (FveXyn4). The sequence that encodes the signal sequence is shown bold (upper case).

FIG. 2C shows a nucleotide sequence (SEQ ID No. 2) encoding a xylanase referred to herein as FveXyn4.

FIG. 3A shows a polypeptide sequence (SEQ ID No. 28) of a xylanase of the present invention (FoxXyn2). Underlined (lower case) portion of the sequence may reflect an N terminal signal peptide which can be cleaved before the enzyme is matured. The amino acids shown in bold and italicized may also be cleaved by post-translational modification before the enzyme is fully matured. In some embodiments this sequence is a backbone sequence.

FIG. 3B shows a polypeptide sequence (SEQ ID No. 29) of a xylanase of the present invention (FoxXyn2). The amino acids shown in bold and italicized may also be cleaved by post-translational modification before the enzyme is fully matured. This sequence may be an active form of the protein and may be one active form of the protein. This may be referred to herein as the mature form of the enzyme. In some embodiments this sequence is a backbone sequence.

FIG. 3C shows a polypeptide sequence (SEQ ID No. 3) of a xylanase referred to herein as FoxXyn2. This is another active form of the enzyme. In some embodiments, this may be referred to herein as the mature form of the enzyme. In some embodiments this sequence is a backbone sequence.

FIG. 4A shows a nucleotide sequence (SEQ ID No. 30) encoding a xylanase of the present invention (FoxXyn2). The lower case nucleotides which are in bold show the intron sequence. The sequence that encodes the signal sequence is shown bold (upper case).

FIG. 4B shows a nucleotide sequence (SEQ ID No. 31) encoding a xylanase of the present invention (FoxXyn2). The sequence that encodes the signal sequence is shown bold (upper case).

FIG. 4C shows a nucleotide sequence (SEQ ID No. 4) encoding a xylanase referred to herein as FoxXyn2.

FIG. 5 shows a polypeptide sequence (SEQ ID No. 5) of a xylanase from *Fusarium-Fusarium* Comparative Sequencing Project, Broad Institute of Harvard and MIT (http://www.broadinstitute.org/)). In some embodiments, this sequence is a backbone sequence.

FIG. 6A shows a nucleotide sequence (SEQ ID No. 32) encoding a xylanase for use in the present invention from *Fusarium*-obtained from *Fusarium* Comparative Sequencing Project, Broad Institute of Harvard and MIT (http://www.broadinstitute.org/)). The lower case nucleotides which are in bold show the intron sequence. The sequence that encodes the signal sequence is shown bold (upper case). Changes compared with SEQ ID No. 24 are underlined.

FIG. 6B shows a nucleotide sequence (SEQ ID No. 33) encoding a xylanase for use in the present invention from *Fusarium*-obtained from *Fusarium* Comparative Sequencing Project, Broad Institute of Harvard and MIT (http://www.broadinstitute.org/)). The sequence that encodes the signal sequence is shown bold (upper case). Changes compared with SEQ ID No. 25 are underlined.

FIG. 6C shows a nucleotide sequence (SEQ ID No. 6) encoding a xylanase for use in the present invention from *Fusarium*-obtained from *Fusarium* Comparative Sequencing Project, Broad Institute of Harvard and MIT (http://www.broadinstitute.org/)), changes compared with SEQ ID No. 4 are underlined.

FIG. 8 shows nucleotide sequences (without introns) of the coding sequences of variant GH10 xylanases in accordance with the present invention (SEQ ID No. 7, SEQ ID No. 8, SEQ ID No. 9, SEQ ID No. 10, and SEQ ID No. 11).

FIG. 9 shows nucleotide sequences (with introns shown underlined) of the coding sequences of variant GH10 xylanases in accordance with the present invention (SEQ ID No. 12, SEQ ID No. 13, SEQ ID No. 14, SEQ ID No. 15, and SEQ ID No. 16).

FIG. 10 shows amino acid sequences of mature variant GH10 xylanases in accordance with the present invention (SEQ ID No. 17, SEQ ID No. 18, SEQ ID No. 19, SEQ ID No. 20, and SEQ ID No. 21).

SUMMARY OF THE INVENTION

Figure 7:
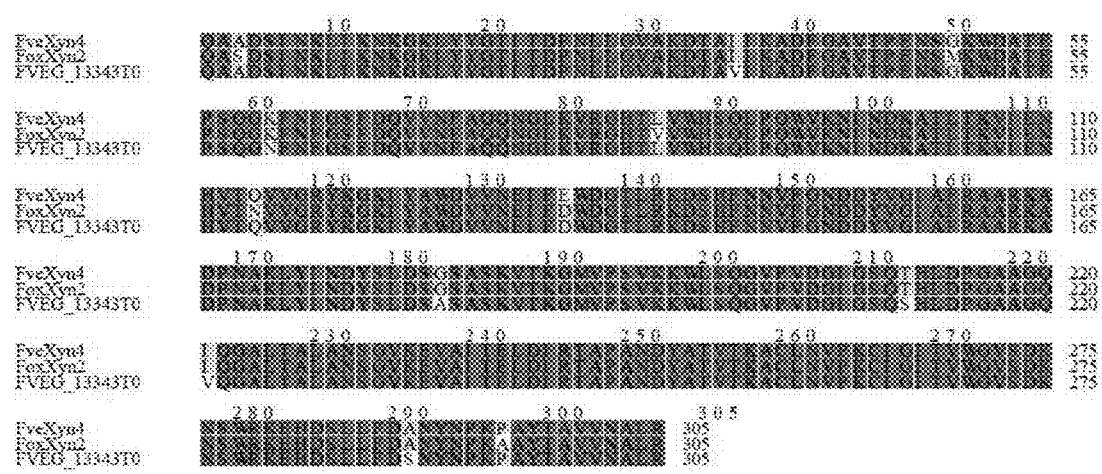
FIG. 7 shows an alignment of the mature proteins for FveXyn4 (SEQ ID No. 1), FoxXyn2 (SEQ ID No. 3) and the xylanase shown herein as SEQ ID No. 5 (FVEG_13343 T0).

A seminal finding of the present invention is the modification of a GH10 xylanase to render the GH10 xylanase more thermostable.

For the first time, the present inventors have identified key residues for modification in order to render GH10 xylanases thermostable.

In addition, for the first time, the present inventors have identified key substitutions/modification in order to render GH10 xylanases thermostable.

In particular, the invention relates to identifying specific residues in and specific modifications of a xylanase, e.g. a GH10 xylanase, to render it more thermostable, whilst ensuring that the other properties of the xylanase remain unchanged.

The other properties of the xylanase of the present invention is its ability to break down (solubilising) insoluble arabinoxylans (AXinsol).

In particular the variant xylanases of the present invention efficiently breakdown (solubilise) AXinsol from a wide range of substrates, including corn, wheat, DDGS, etc., in particular corn and corn based substrates, in particular both wheat (including wheat-based) products and corn (including corn-based products). This contrasts with prior-known enzymes, which are often inferior at solubilising AXinsol in corn or corn-based substrates or which are not efficient in both wheat- and corn-based substrates.

In addition, the variant xylanases of the present invention are particularly good at not only breaking down (solubilising) AXinsol, but also breaking down (or degrading) the solubilized polymers efficiently. By being able to efficiently (quickly) breakdown (degrade) the solubilized polymers (obtained from dissolving AXinsol), a (fast) reduction in viscosity is obtained or the solubilized polymers (obtained from dissolving AXinsol) cannot contribute to increasing viscosity. This latter effect is essential in some of the claimed applications.

Without wishing to be bound by theory, the variant enzyme of the present invention mainly releases polymers, which do not contribute to viscosity, because the released polymers are short.

Typically, conventional xylanases may breakdown AXinsol, but will often lead to an increase in viscosity of the mixture. This increased viscosity is disadvantageous in many applications.

Without wishing to be bound by theory, although some conventional xylanases breakdown AXinsol, they lead to an increase in soluble degradation products of high molecular weight, which leads to an increase in viscosity in the mixture.

Furthermore or alternatively and again without wishing to be bound by theory, conventional xylanase enzymes may breakdown AXinsol, but because they do not degrade the solubilised products of high molecular weight fast enough the viscosity in the mixture is not ideal. In contrast, with the methods and uses of the present invention, the variant xylanases breakdown AXinsol without increasing viscosity and/or whilst reducing viscosity quickly compared with conventional enzymes. Without wishing to be being bound by theory, it is believed that high molecular weight products are not formed by the enzymes of the present invention.

The enzymes of the present invention and as described herein have been found to not only breakdown (solubilise) insoluble arabinoxylans (AXinsol) from a wide range of substrates, including corn, wheat, DDGS, etc., in particular corn and corn-based substrates, in particular both wheat (including wheat-based) products and corn (including corn-based products), but also efficiently ensuring that viscosity is not raised and/or reducing viscosity. Without wishing to be being bound by theory, it is believed that high molecular weight products are not formed by the enzymes of the present invention.

Thus the present invention relates to enzymes capable of solubilising pentosans, in particular xylan-containing materials, such as arabinoxylans, in particular insoluble arabinoxylans. In particular the enzyme is particularly good at solubilising pentosans in particular xylan-containing materials, such as arabinoxylans, in particular insoluble arabinoxylans, in a broad spectrum of substrates, including corn based substrates.

The present invention further relates to enzymes capable of degrading AXsol or the breakdown products of AXinsol to ensure viscosity is not increased and/or is reduced in the reaction mixture.

Many of the xylanases commercialized for use in feedstuffs for solubilizing pentosans are GH11 enzymes. It had been considered by those skilled in the art that GH10 xylanases were not as strong at solublizing pentosans, particularly AXinsol, compared with GH11 xylanases. Surprisingly it has been found that the novel xylanase disclosed herein which is a GH10 xylanase is particularly good at degrading AXinsol in a broad spectrum of substrates, including corn based substrates. Surprisingly, the present inventors have found that the variant GH10 xylanases of the present invention outperform commercial GH11 xylanases in their ability to solubilize pentosans. In addition the variant OH10 xylanases are thermostable.

The fact that the present enzymes efficiently degrade AXinsol from corn and corn-based substrates is significantly advantageous as corn holds much more AX in the insoluble form compared with other cereals, such as wheat and rye for example. Therefore only xylanases that can breakdown AXinsol can show significant benefit to animals fed on corn-based diet, such as corn-soy diet for example.

It was completely unexpected for a OH10 xylanase to be so good at degrading AXinsol in cereals, particularly in corn or corn-based substrates.

The enzymes of the present invention are able to efficiently (and quickly) degrade the polymers and oligomers that are produced from degradation of AXinsol or that are present in grain-based material. This leads to an unexpected advantage for the GH10 xylanases taught herein in that they are particularly good in a number of applications to keep viscosity low or to reduce viscosity, e.g. in feedstuffs; in brewing and/or malting; in grain-based production of glucose, e.g. for further processing to biofuels and/or biochemicals (e.g. bio-based isoprene); or in the wheat gluten-starch separation industry for the production of starch for example.

Notably it has been found that the degradation product on average is shorter for the GH10 enzymes tested herein compared with GH11 enzymes. This means that the degradation products do not contribute to or cause an increase in viscosity.

Based on these findings, the variant xylanases according to the present invention can be used to degrade a xylan-containing material, particularly arabinoxylans, particularly AXinsol. In addition or alternatively, the xylanases according to the present invention can be used to degrade soluble polymers (e.g. oligomers) that are produced from degradation of AXinsol or that are (naturally) present in grain-based materials. Surprisingly it has been found that the variant xylanases according the present invention can be used to both degrade a xylan-containing material, particularly arabinoxylans, particularly AXinsol, and to degrade soluble polymers (e.g. oligomers) that are produced from degradation of AXinsol.

Such enzymes finds useful application in many industries, including feedstuffs, malting and brewing, in the treatment of arabinoxylan containing raw materials like grain-based materials, herein grain-based materials includes grains and cereals, in the wheat gluten-starch separation industry, in the production of starch derived syrups, in biofuel production, and the like.

The term "variant xylanase(s)" as used herein may be used interchangeably with "modified xylanase(s)".

STATEMENTS OF THE INVENTION

In a first aspect the present invention provides, a modified GH10 xylanase enzyme or a fragment thereof having xylanase activity wherein said modified GH10 xylanase or fragment thereof has increased thermostability compared with a parent GH10 xylanase enzyme, the parent GH10 xylanase having been modified at two or more of (preferably at three or more of, more preferably at least all five of) the following positions 7, 33, 79, 217 and 298, wherein the numbering is based on the amino acid numbering of FveXyn4 (SEQ ID No. 1).

In another aspect, the present invention provides a nucleic acid molecule (e.g. an isolated or recombinant nucleic acid molecule) encoding a thermostable xylanase and comprising (or consisting of) a backbone polynucleotide sequence comprising (or consisting of) a nucleotide sequence selected from the group consisting of:
  a. a nucleotide sequence shown herein as SEQ ID No. 2, SEQ ID No. 24, SEQ ID No. 25, SEQ ID No. 4, SEQ ID No. 30, SEQ ID No. 31, SEQ ID No. 6, SEQ ID No 32 or SEQ ID No. 33; or
  b. a nucleotide sequence having at least 70% identity (suitably at least 80%, suitably at least 90%, suitably at least 95%, suitably at least 98%, suitably at least 99% identity) with SEQ ID No. 2, SEQ ID No. 24, SEQ ID No. 25, SEQ ID No. 4, SEQ ID No. 30, SEQ ID No. 31, SEQ ID No. 6, SEQ ID No 32 or SEQ ID No. 33; or
  c. a nucleotide sequence which can hybridize to SEQ ID No. 2, SEQ ID No. 24, SEQ ID No. 25, SEQ ID No. 4, SEQ ID No. 30, SEQ ID No. 31, SEQ ID No. 6, SEQ ID No 32 or SEQ ID No. 33 under high stringency conditions;
  which backbone polynucleotide sequence is modified at two or more of (preferably at three or more, more preferably at least all five of) the codons encoding amino acids 7, 33, 79, 217 and 298 in the encoded polypeptide, wherein the numbering is based on the amino acid numbering of FveXyn4 (SEQ ID No. 1).

In a yet further aspect, the present invention provides a vector (e.g. a plasmid) or construct comprising (or consisting of) a backbone polynucleotide sequence comprising a nucleotide sequence selected from the group consisting of:
  a. a nucleotide sequence shown herein as SEQ ID No. 2, SEQ ID No. 24, SEQ ID No. 25, SEQ ID No. 4, SEQ ID No. 30, SEQ ID No. 31, SEQ ID No. 6, SEQ ID No 32 or SEQ ID No. 33; or
  b. a nucleotide sequence having at least 70% identity (suitably at least 80%, suitably at least 90%, suitably at least 95%, suitably at least 98%, suitably at least 99% identity) with SEQ ID No. 2, SEQ ID No. 24, SEQ ID No. 25, SEQ ID No. 4, SEQ ID No. 30, SEQ ID No. 31, SEQ ID No. 6, SEQ ID No 32 or SEQ ID No. 33; or
  c. a nucleotide sequence which can hybridize to SEQ ID No. 2, SEQ ID No. 24, SEQ ID No. 25, SEQ ID No. 4, SEQ ID No. 30, SEQ ID No. 31, SEQ ID No. 6, SEQ ID No 32 or SEQ ID No. 33 under high stringency conditions;
  which backbone polynucleotide sequence is modified at two or more of (preferably at three or more, more preferably at least all five of) the codons encoding amino acids 7, 33, 79, 217 and 298 in the encoded polypeptide, wherein the numbering is based on the amino acid numbering of FveXyn4 (SEQ ID No. 1.

The present invention yet further provides a host cell comprising the nucleic acid according to the present invention or a vector or construct according to the present invention.

The present invention, in one aspect, provides a method for improving the thermostability of a GH10 xylanase, comprising: modifying a parent GH10 xylanase at two or more of (preferably at three or more of, more preferably at least all five of) the following positions: 7, 33, 79, 217 and 298, wherein the numbering is based on amino acid numbering of FveXyn4 (SEQ ID No. 1).

In a further aspect, the present invention provides an enzyme having xylanase activity, said enzyme being a GH10 xylanase or a fragment thereof, said enzyme having modifications at two or more (suitably three or more, suitably at least all) of the following positions 7, 33, 79, 217 and 298 wherein the numbering is based on the amino acid numbering of FveXyn4 (SEQ ID No. 1) and said enzyme having increased thermostability compared to a GH10 xylanase which comprises an amino acid sequence which is identical to said enzyme except for said modifications.

The present invention yet further provides a GH10 xylanase enzyme or a fragment thereof having xylanase activity wherein said GH10 xylanase enzyme comprises a polypeptide having at least 70% (suitably at least 80%, suitably at least 90%, suitably at least 95%, suitably at least 98%, suitably at least 99%) identity to a GH10 xylanase (e.g. a parent GH10 xylanase); and comprises the following amino acids at two or more of (suitably at three or more of, suitably at all of) the positions indicated: 7D; 33V; 79Y, V, F, I, L or M (preferably 79Y, F or V, more preferably Y); 217Q, E, P, D or M (preferably 217Q, E or P, more preferably Q); and 298Y, F or W (preferably Y or F, more preferably Y) wherein the numbering is based on the amino acid numbering of FveXyn4 (SEQ ID No. 1).

In a yet further aspect, there is provided a GH10 xylanase enzyme or a fragment thereof having xylanase activity wherein said GH10 xylanase enzyme comprises a polypeptide having at least 90% (suitably at least 95%, suitably at least 98%, suitably at least 99%) identity to a GH10 xylanase (e.g. a parent or backbone GH10 xylanase); and comprises at the following amino acids at two or more of (suitably at three or more of, suitably at all of) the positions indicated: 7D; 33V; 79Y; 217Q); and 298Y wherein the numbering is based on the amino acid numbering of FveXyn4 (SEQ ID No. 1).

The present invention also provides a method of producing a xylanase variant, comprising:
  a. modifying (e.g. transforming) a host cell with a nucleic acid molecule according to the present invention, or a vector or construct (e.g. DNA construct) according to the present invention, or with a DNA construct comprising a promoter having transcriptional activity in the host cell operably linked with a heterologous polynucleotide sequence according to the present invention, or with a DNA construct comprising a promoter having transcriptional activity in the host cell operably linked with a heterologous polynucleotide sequence encoding a xylanase variant according to the present invention;
  b. cultivating the modified (e.g. transformed) host cell in a suitable culture medium to allow expression of the xylanase.

In a further aspect of the present invention there is provided a fermentate produced by the method of the present invention.

A yet further aspect of the present invention is the provision of a xylanase produced by the method of the present invention.

The present invention yet further provides an enzyme composition comprising a) an enzyme having xylanase activity, e.g. the GH10 xylanase enzyme (such as the modified GH10 xylanase enzyme) or a fragment thereof, according to the present invention, b) the fermentate according to the present invention, or c) a combination thereof.

The present invention further provides a feed additive composition comprising a) an enzyme having xylanase activity, e.g. the GH10 xylanase enzyme (such as the modified GH10 xylanase enzyme) or a fragment thereof, according to the present invention, b) the fermentate according to the present invention, or c) a combination thereof.

In a further aspect of the present invention there is provided a premix comprising a) an enzyme having xylanase activity, e.g. the GH10 xylanase enzyme (such as the modified GH10 xylanase enzyme) or a fragment thereof, according to the present invention, b) the fermentate according to the present invention, c) the enzyme composition according to the present invention, d) a feed additive composition according to the present invention or e) a combination thereof; and at least one vitamin and/or at least one mineral.

The present invention yet further provides a feed (or feedstuff) comprising a) an enzyme having xylanase activity, e.g. the GH10 xylanase enzyme (such as the modified GH10 xylanase enzyme) or a fragment thereof, according to the present invention, b) the fermentate according to the present invention, c) the enzyme composition according to the present invention, d) a feed additive composition according to the present invention, e) a premix according to the present invention or f) a combination thereof.

In a further aspect there is provided a method of preparing a feedstuff comprising admixing a feed component with a) an enzyme having xylanase activity, e.g. the GH10 xylanase enzyme (such as the modified GH10 xylanase enzyme) or a fragment thereof, according to the present invention, b) the fermentate according to the present invention, c) the enzyme composition according to the present invention, d) a feed additive composition according to the present invention, e) a premix according to the present invention or f) a combination thereof.

The present invention yet further provides a method for degrading arabinoxylan-containing material in a xylan-containing material, comprising admixing said xylan-containing material with a) an enzyme having xylanase activity, e.g. the GH10 xylanase enzyme (such as the modified GH10 xylanase enzyme) or a fragment thereof, according to the present invention, b) the fermentate according to the present invention, c) the enzyme composition according to the present invention, d) a feed additive composition according to the present invention, e) a premix according to the present invention or f) a combination thereof.

In another aspect, there is provided use of a) an enzyme having xylanase activity, e.g. the GH10 xylanase enzyme (such as the modified GH10 xylanase enzyme) or a fragment thereof according to the present invention, b) the fermentate according to the present invention, c) the enzyme composition according to the present invention, d) a feed additive composition according to the present invention, e) a premix according to the present invention or f) a combination thereof for solubilizing arabinoxylan in a xylan-containing material.

DETAILED DISCLOSURE OF THE PREFERRED EMBODIMENTS OF THE INVENTION

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure which can be had by reference to the specification as a whole. Accordingly, the terms defined immediately below are more fully defined by reference to the specification as a whole.

Amino acids are referred to herein using the name of the amino acid, the three letter abbreviation or the single letter abbreviation.

The term "protein", as used herein, includes proteins, polypeptides, and peptides.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to understand that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "an enzyme" includes a plurality of such candidate agents and reference to "the feed" includes reference to one or more feeds and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

Increasing prices of raw material traditionally used as energy source in animal feed, as a feedstock in biofuel production, as an ingredient in brewing or malting, or as a feedstock in wheat gluten-starch separation processes for instance have resulted in inclusion of low-cost fibrous materials in the starting substrates for these industries, particularly the use of low-cost fibrous by-products in animal feed.

Fibre addition may cause several disadvantageous effects. For example in animal feed fibre addition may cause anti-nutritional effects. The presence of un-degraded polymers present in the animal's intestine causes a highly viscous content and impeded diffusion with reduced nutrient absorption as a result. Also, the polymers possess a high water holding capacity hindering an effective re-absorption of water, and the water retention increases the volume of the gut content, which leads to a decrease intestinal transit time (Englyst & Kingman (1993) in Human Nutrition and Dietetics, 9th edition (Garrow J. S., James W. P. T., eds.) p. 53).

In feedstuffs, hemicellulose and cellulose (including insoluble arabinoxylan) also form physical barriers encapsulating (or entrapping) nutrients like starch and protein and thereby retaining access to these nutrients for the animal.

Hemicellulose and cellulose (including insoluble arabinoxylans (AXinsol)) by themselves are also potential energy sources, as they consist of C5- and C6-saccharides. Mono C6-saccharides can be used as energy source by the animal, while oligo C5-saccharides can be transformed into short chain fatty acids by the micro flora present in the animal gut (van den Broek et al., 2008 Molecular Nutrition & Food Research, 52, 146-63), which short chain fatty acids can be taken up and digested by the animal's gut.

Release of nutrients and water from feedstuffs as a consequence of physical barrier degradation is dependent on the ability of the xylanase to degrade insoluble fibre components (e.g. insoluble arabanoxylans (AXinsol)).

The present invention provides an enzyme wherein said enzyme is a GH10 xylanase or a fragment thereof having xylanase activity, wherein said enzyme or fragment thereof has increased thermostability compared with a parent GH10 xylanase enzyme, the parent GH10 xylanase having been modified at, at least, two of the following positions 7, 33, 79, 217 and 298, wherein the numbering is based on the amino acid numbering of FveXyn4 (SEQ ID No. 1).

The present invention further provides, an enzyme wherein said enzyme is a GH10 xylanase or a fragment thereof having xylanase activity, wherein said enzyme or fragment thereof has increased thermostability compared with a parent GH10 xylanase enzyme, the parent GH10 xylanase having been modified at, at least, three of the following positions 7, 33, 79, 217 and 298, wherein the numbering is based on the amino acid numbering of FveXyn4 (SEQ ID No. 1).

The present invention provides, an enzyme wherein said enzyme is a GH10 xylanase or a fragment thereof having xylanase activity, wherein said enzyme or fragment thereof has increased thermostability compared with a parent GH10 xylanase enzyme, the parent GH10 xylanase having been modified at, at least, the following positions 7, 33, 79, 217 and 298, wherein the numbering is based on the amino acid numbering of FveXyn4 (SEQ ID No. 1).

In one embodiment the enzyme having xylanase activity, e.g. the GH10 xylanase enzyme (such as the modified GH10 xylanase enzyme) or a fragment thereof, according to the present invention comprises at least two of (preferably at least three of) the following modifications:
N7D;
T33V;
K79Y, V, F, I, L or M;
A217Q, E, P, D or M; and
T298Y, F or W.

In one embodiment the enzyme having xylanase activity, e.g. the GH10 xylanase enzyme (such as the modified GH10 xylanase enzyme) or a fragment thereof, according to the present invention comprises the following amino acids at least two of (preferably at least three of) the positions indicated:
7D;
33V;
79Y, V, F, I, L or M;
217Q, E, P, D or M; and
298Y, F or W.

In one embodiment the modified xylanase enzyme according to the present invention comprises at least two of (preferably at least three of) the following modifications:
N7D;
T33V;
K79Y, F or V;
A217Q, E or P; and
T298Y or F.

In one embodiment the enzyme having xylanase activity, e.g. the GH10 xylanase enzyme (such as the modified GH10 xylanase enzyme) or a fragment thereof, according to the present invention comprises the following amino acids at least two of (preferably at least three of) the positions indicated:
7D;
33V;
79Y, F or V;
217Q, E or P; and
298Y or F.

In one embodiment the modified xylanase enzyme according to the present invention comprises at least two of (preferably at least three of) the following modifications:
N7D;
T33V;
K79Y;
A217Q; and
T298Y.

In one embodiment the enzyme having xylanase activity, e.g. the GH10 xylanase enzyme (such as the modified GH10 xylanase enzyme) or a fragment thereof, according to the present invention comprises the following amino acids at least two of (preferably at least three of) the positions indicated:
7D;
33V;
79Y;
217Q; and
298Y.

In one embodiment the modified xylanase enzyme according to the present invention comprises at least the following modifications:
N7D;
T33V;
K79Y, V, F, I, L or M;
A217Q, E, P, D or M; and
T298Y, F or W.

In one embodiment the enzyme having xylanase activity, e.g. the GH10 xylanase enzyme (such as the modified GH10 xylanase enzyme) or a fragment thereof, according to the present invention comprises the following amino acids at the positions indicated:
7D;
33V;
79Y, V, F, I, L or M;
217Q, E, P, D or M; and
298Y, F or W.

In one embodiment the modified xylanase enzyme according to the present invention comprises at least the following modifications:
N7D;
T33V;
K79Y, F or V;
A217Q, E or P; and
T298Y or F.

In one embodiment the enzyme having xylanase activity, e.g. the GH10 xylanase enzyme (such as the modified GH10 xylanase enzyme) or a fragment thereof, according to the present invention comprises the following amino acids at the positions indicated:
7D;
33V;
79Y, F or V;
217Q, E or P; and
298Y or F.

In one embodiment the modified xylanase enzyme according to the present invention comprises at least the following modifications:
N7D;
T33V;
K79Y;
A217Q; and
T298Y.

In one embodiment the enzyme having xylanase activity, e.g. the GH10 xylanase enzyme (such as the modified GH10 xylanase enzyme) or a fragment thereof, according to the present invention comprises the following amino acids at the positions indicated:
7D;
33V;
79Y;
217Q; and
298Y.

In one embodiment in addition to being modified at two or more (preferably at three or more, more preferably at all) of positions 7, 33, 79, 217 and 298 the modified xylanase enzyme according to the present invention may be further modified at one or more of the following positions: 25, 57, 62, 64, 89, 103, 115, 147, 181, 193, 219.

In one embodiment in addition to being modified at two or more (preferably at three or more, more preferably at all) of positions 7, 33, 79, 217 and 298 the modified xylanase enzyme according to the present invention may be further modified at two or more of the following positions: 25, 57, 62, 64, 89, 103, 115, 147, 181, 193, 219.

In one embodiment in addition to being modified at two or more (preferably at three or more, more preferably at all) of positions 7, 33, 79, 217 and 298 the modified xylanase enzyme according to the present invention may be further modified at three or more of the following positions: 25, 57, 62, 64, 89, 103, 115, 147, 181, 193, 219.

In one embodiment in addition to being modified at two or more (preferably at three or more, more preferably at all) of positions 7, 33, 79, 217 and 298 the modified xylanase enzyme according to the present invention may be further modified at four or more of the following positions: 25, 57, 62, 64, 89, 103, 115, 147, 181, 193, 219.

In one embodiment in addition to being modified at two or more (preferably at three or more, more preferably at all) of positions 7, 33, 79, 217 and 298 the modified xylanase enzyme according to the present invention may be further modified at five or more of the following positions: 25, 57, 62, 64, 89, 103, 115, 147, 181, 193, 219.

In one embodiment in addition to being modified at two or more (preferably at three or more, more preferably at all) of positions 7, 33, 79, 217 and 298 the modified xylanase enzyme according to the present invention may be further modified at seven or more of the following positions: 25, 57, 62, 64, 89, 103, 115, 147, 181, 193, 219.

In one embodiment in addition to being modified at two or more (preferably at three or more, more preferably at all) of positions 7, 33, 79, 217 and 298 the modified xylanase enzyme according to the present invention may be further modified at nine or more of the following positions: 25, 57, 62, 64, 89, 103, 115, 147, 181, 193, 219.

When the modified xylanase enzyme is further modified at position 25, the modification may be N25P. In other words the amino acid at residue 25 of the GH10 xylanase of the present invention is preferably P.

When the modified xylanase enzyme is further modified at position 57, the modification may be selected from S57Q, T or V (preferably Q). In other words the amino acid at residue 57 of the GH10 xylanase of the present invention is preferably Q, T or V (preferably Q).

When the modified xylanase enzyme is further modified at position 62, the modification may be selected from N62T or S (preferably T). In other words the amino acid at residue 62 of the GH10 xylanase of the present invention is preferably T or S (preferably T).

When the modified xylanase enzyme is further modified at position 64, the modification may be selected from G64T or S (preferably T). In other words the amino acid at residue 64 of the GH10 xylanase of the present invention is preferably T or S (preferably T).

When the modified xylanase enzyme is further modified at position 89, the modification may be selected from S89G, N, Q, L or M (preferably G or Q, more preferably G). In other words the amino acid at residue 89 of the GH10 xylanase of the present invention is preferably G, N, Q, L or M (preferably G or Q, more preferably G).

When the modified xylanase enzyme is further modified at position 103, the modification may be selected from T103M or K (preferably M). In other words the amino acid at residue 103 of the GH10 xylanase of the present invention is preferably M or K (preferably M).

When the modified xylanase enzyme is further modified at position 115, the modification may be selected from V115E or L (preferably L). In other words the amino acid at residue 115 of the GH10 xylanase of the present invention is preferably E or L (preferably L).

When the modified xylanase enzyme is further modified at position 147, the modification may be N147Q. In other words the amino acid at residue 147 of the GH10 xylanase of the present invention is preferably Q.

When the modified xylanase enzyme is further modified at position 181, the modification may be selected from G181Q, A, D or P (preferably Q). In other words the amino acid at residue 181 of the GH10 xylanase of the present invention is preferably Q, A, D or P (preferably Q).

When the modified xylanase enzyme is further modified at position 193, the modification may be selected from S193Y or N (preferably Y). In other words the amino acid at residue 193 of the GH10 xylanase of the present invention is preferably 193Y or N (preferably Y).

When the modified xylanase enzyme is further modified at position 219, the modification may be selected from G219D or P (preferably P). In other words the amino acid at residue 219 of the GH10 xylanase of the present invention is preferably D or P (preferably P).

In one embodiment, the modified xylanase enzyme according to the present invention in addition to comprising modifications at two or more (preferably at three or more, more preferably at all) of positions 7, 33, 79, 217 and 298 further comprises modifications in the following residues: 25 and 89 (preferably N25P and S89G).

In one embodiment, the modified xylanase enzyme according to the present invention in addition to comprising modifications at two or more (preferably at three or more, more preferably at all) of positions 7, 33, 79, 217 and 298 further comprises modifications in the following residues: 57, 62, 64 and 89 (preferably S57Q, N62T, G64T and S89G).

In one embodiment, the modified xylanase enzyme according to the present invention in addition to comprising modifications at two or more (preferably at three or more, more preferably at all) of positions 7, 33, 79, 217 and 298 further comprises modifications in the following residues: 25, 57, 62, 64, 103, 115, 147, 181, 193 and 219 (preferably N25P, S57Q, N62T, G64T T103M, V115L, N147Q, G181Q, S193Y and G219P).

In one embodiment, the modified xylanase enzyme according to the present invention in addition to comprising modifications at two or more (preferably at three or more, more preferably at all) of positions 7, 33, 79, 217 and 298 further comprises modifications in the following residues: 25, 57, 62, 89, 103, 115, 147, 181, 193 and 219 (preferably N25P, S57Q, N62T, S89G, T103M, V115L, N147Q, G181Q, S193Y, G219P and T298Y.

In one embodiment, the modified xylanase enzyme according to the present invention in addition to comprising modifications at two or more (preferably at three or more, more preferably at all) of positions 7, 33, 79, 217 and 298 further comprises modifications in the following residues: 25, 89 and 64 (preferably N25P, S89G, G64T)

In one embodiment, the modified xylanase enzyme (or the GH10 xylanase) according to the present invention may comprise the following amino acids at the positions indicated:
 a. 7D, 25P, 33V, 64T, 79Y, 89G, 217Q and 298Y;
 b. 7D, 25P, 33V, 79Y, 89G, 217Q and 298Y;
 c. 7D, 25P, 33V, 57Q, 62T, 64T, 79Y, 103M, 115L, 147Q, 181Q, 193Y, 217Q, 219P and 298Y;
 d. 7D, 25P, 33V, 57Q, 62T, 79Y, 89G, 103M, 115L, 147Q, 181Q, 193Y, 217Q, 219P and 298Y;
 e. 7D, 33V, 57Q, 62T, 64T, 79Y, 89G, 217Q and 298Y;
 f. 79F 217 Q and 298F;
 g. 7D, 33, 217 Q and 298F;
 h. 7D, 79F and 298F;
 i. 33V, 79F and 217 Q;
 j. 7D, 33V and 298 Y;
 k. 33V, 217 Q and 298Y;
 l. 7D, 217Q and 298F;
 m. 7D, 33V and 217Q;
 n. 79F and 298F;
 o. 7D and 79F;
 p. 33V and 79F;
 q. 33V and 298 Y;
 r. 7D and 33V; or
 s. 33V and A217Q.

In one embodiment, the modified xylanase enzyme (or the GH10 xylanase) according to the present invention may comprise the following amino acids at the positions indicated:
 a. 7D, 25P, 33V, 64T, 79Y, 89G, 217Q and 298Y;
 b. 7D, 25P, 33V, 79Y, 89G, 217Q and 298Y;
 c. 7D, 25P, 33V, 57Q, 62T, 64T, 79Y, 103M, 115L, 147Q, 181Q, 193Y, 217Q, 219P and 298Y;
 d. 7D, 25P, 33V, 57Q, 62T, 79Y, 89G, 103M, 115L, 147Q, 181Q, 193Y, 217Q, 219P and 298Y;
 e. 7D, 33V, 57Q, 62T, 64T, 79Y, 89G, 217Q and 298Y;

In one embodiment, the modified xylanase enzyme (or the GH10 xylanase) according to the present invention may comprise the following modifications:
 a. N7D, N25P, T33V, G64T, K79Y, S89G, A217Q and T298Y;
 b. N7D, N25P, T33V, K79Y, S89G, A217Q and T298Y;
 c. N7D, N25P, T33V, S57Q, N62T, G64T, K79Y, T103M, V115L, N147Q, G181Q, S193Y, A217Q, G219P and T298Y;
 d. N7D, N25P, T33V, S57Q, N62T, K79Y, S89G, T103M, V115L, N147Q, G181Q, S193Y, A217Q, G219P and T298Y;
 e. N7D, T33V, S57Q, N62T, G64T, K79Y, S89G, A217Q and T298Y;
 f. K79F A217Q T298F;
 g. N7D T33V A217Q T298F;
 h. N7D K79F T298F;
 i. T33V K79F A217Q;
 j. N7D T33V T298Y;
 k. T33V A217Q T298Y;
 l. N7D A217Q T298F;
 m. N7D T33V A217Q;
 n. K79F T298F;
 o. N7D K79F;
 p. T33V K79F;
 q. T33V T298Y;
 r. N7D T33V; or
 s. T33V A217Q.

In one embodiment, the modified xylanase enzyme (or the GH10 xylanase) according to the present invention may comprise the following modifications:
 a. N7D, N25P, T33V, G64T, K79Y, S89G, A217Q and T298Y;
 b. N7D, N25P, T33V, K79Y, S89G, A217Q and T298Y;
 c. N7D, N25P, T33V, S57Q, N62T, G64T, K79Y, T103M, V115L, N147Q, G181Q, S193Y, A217Q, G219P and T298Y;
 d. N7D, N25P, T33V, S57Q, N62T, K79Y, S89G, T103M, V115L, N147Q, G181Q, S193Y, A217Q, G219P and T298Y;
 e. N7D, T33V, S57Q, N62T, G64T, K79Y, S89G, A217Q and T298Y;

In one embodiment the xylanase enzyme according to the present invention (e.g. the modified xylanase enzyme) has a backbone amino acid sequence (before modification) which comprises (or consists of) an amino acid sequence selected from the group consisting of SEQ ID No. 1, SEQ ID No. 26, SEQ ID No. 27, SEQ ID No. 3, SEQ ID No 28, SEQ ID No. 29, or SEQ ID No. 5; or an amino acid sequence having at least 70% identity (suitably at least 80%, suitably at least 90%, suitably at least 95%, suitably at least 98%, suitably at least 99% identity) with SEQ ID No. 1, SEQ ID No. 26, SEQ ID No. 27, SEQ ID No. 3, SEQ ID No 28, SEQ ID No. 29, or SEQ ID No. 5; or an amino acid sequence encoded by a nucleotide sequence comprising the nucleotide sequence shown herein as SEQ ID No. 2, SEQ ID No. 24, SEQ ID No. 25, SEQ ID No. 4, SEQ ID No. 30, SEQ ID No. 31, SEQ ID No. 6, SEQ ID No 32 or SEQ ID No. 33; or an amino acid sequence encoded by a nucleotide sequence comprising a nucleotide sequence having at least 70% identity (suitably at least 80%, suitably at least 90%, suitably at least 95%, suitably at least 98%, suitably at least 99% identity) with SEQ ID No. 2, SEQ ID No. 24 or SEQ ID No. 25, SEQ ID No. 4, SEQ ID No. 30, SEQ ID No. 31, SEQ ID No. 6, SEQ ID No 32 or SEQ ID No. 33; or an amino acid sequence encoded by a nucleotide sequence which can hybridize to SEQ ID No. 2, SEQ ID No. 24, SEQ ID No. 25, SEQ ID No. 4, SEQ ID No. 30, SEQ ID No. 31, SEQ ID No. 6, SEQ No 32 or SEQ ID No. 33 under high stringency conditions.

The term "parent" means a xylanase, preferably a GH10 xylanase, to which an alteration is made to produce a modified enzyme of the present invention. In one embodiment the parent enzyme is a GH10 xylanase. Suitably the parent enzyme may be a naturally occurring (wild-type) polypeptide or a variant or fragment thereof. In a preferred embodiment the parent enzyme is a naturally occurring (wild-type polypeptide).

Suitably the modified xylanase or the GH10 xylanase according to the present invention comprises (or consists essentially of, or consists of) an amino acid sequence which is identical or substantially identical to said parent enzyme except for a modification at two or more (preferably at three or more, more preferably at least all five of) the following positions 7, 33, 79, 217 and 298, wherein the numbering is based on the amino acid numbering of FveXyn4 (SEQ ID No. 1).

In some embodiments, the modified xylanase or the GH10 xylanase according to the present invention comprises (or consists essentially of, or consists of) an amino acid sequence which is identical or substantially identical to said parent enzyme except for a modification at two or more (preferably at three or more, more preferably at least all five of) the following positions 7, 33, 79, 217 and 298, as well as at one or more of the following positions 25, 57, 62, 64, 89, 103, 115, 147, 181, 193, 219, wherein the numbering is based on the amino acid numbering of FveXyn4 (SEQ ID No. 1).

The modified GH10 xylanase or GH10 xylanase according to the present invention (and claimed in claim 1 for instance) suitably has about at least 90% sequence identity (preferably at least 93%, suitably at least 97%, suitably at least 99% sequence identity to the parent enzyme.

The term "backbone" as used herein means a polypeptide sequence that is a GH10 xylanase polypeptide, which is modified to comprise the following amino acids at two or more (preferably at three or more, more preferably at all) of the positions indicated: 7D; 33V; 79Y, V, F, I, L or M (preferably 79Y, F or V, more preferably Y); 217Q, E, P, D or M (preferably 217Q, E or P, more preferably Q); and 298Y, F or W (preferably Y or F, more preferably Y) wherein the numbering is based on the amino acid numbering of FveXyn4 (SEQ ID No. 1).

The enzyme having xylanase activity, e.g. the GH10 xylanase enzyme, of the present invention (e.g. the modified GH10 xylanase enzyme) preferably comprises a polypeptide having at least 70% (suitably at least 80%, suitably at least 90%, suitably at least 95%, suitably at least 98%, suitably at least 99%) identity to a GH10 xylanase (e.g. a parent or backbone GH10 xylanase); and comprises the following amino acids at two or more (preferably at three or more, more preferably at all) of the positions indicated: 7D; 33V; 79Y, V, F, I, L or M (preferably 79Y, F or V, more preferably Y); 217Q, E, P, D or M (preferably 217Q, E or P, more preferably Q); and 298Y, F or W (preferably Y or F, more preferably Y) wherein the numbering is based on the amino acid numbering of FveXyn4 (SEQ ID No. 1).

The enzyme having xylanase activity, e.g. the GH10 xylanase enzyme, of the present invention (e.g. the modified GH10 xylanase enzyme) preferably comprises a polypeptide having at least at least 95% (suitably at least 98%, suitably at least 99%) identity to a GH10 xylanase (e.g. a parent or backbone GH10 xylanase); and comprises the following amino acids at two or more (preferably at three or more, more preferably at all) of the positions indicated: 7D; 33V; 79Y; 217Q); and 298Y wherein the numbering is based on the amino acid numbering of FveXyn4 (SEQ ID No. 1).

In one embodiment the parent or backbone GH10 xylanase (before modification) is:
   a. a xylanase comprising an amino acid sequence selected from the group consisting of SEQ ID No. 1, SEQ ID No. 26, SEQ ID No. 27, SEQ ID No. 3, SEQ ID No 28, SEQ ID No. 29, or SEQ ID No. 5; or
   b. a xylanase enzyme comprising an amino acid sequence having at least 70% identity (suitably at least 80%, suitably at least 90%, suitably at least 95%, suitably at least 98%, suitably at least 99% identity) with SEQ ID No. 1, SEQ ID No. 26, SEQ ID No. 27, SEQ ID No. 3, SEQ ID No 28, SEQ ID No. 29, or SEQ ID No. 5; or
   c. a xylanase enzyme encoded by a nucleotide sequence comprising the nucleotide sequence shown herein as SEQ ID No. 2, SEQ ID No. 24, SEQ ID No. 25, SEQ ID No. 4, SEQ ID No. 30, SEQ ID No. 31, SEQ ID No. 6, SEQ ID No 32 or SEQ ID No. 33; or
   d. a xylanase enzyme encoded by a nucleotide sequence comprising a nucleotide sequence having at least 70% identity (suitably at least 80%, suitably at least 90%, suitably at least 95%, suitably at least 98%, suitably at least 99% identity) with SEQ ID No. 2, SEQ ID No. 24, SEQ ID No. 25, SEQ ID No. 4, SEQ ID No. 30, SEQ ID No. 31, SEQ ID No. 6, SEQ ID No 32 or SEQ ID No. 33; or
   e. a xylanase enzyme encoded by a nucleotide sequence which can hybridize to SEQ ID No. 2, SEQ ID No. 24, SEQ ID No. 25, SEQ ID No. 4, SEQ ID No. 30, SEQ ID No. 31, SEQ ID No. 6, SEQ ID No 32 or SEQ ID No. 33 under high stringency conditions.

In one embodiment the parent or backbone amino acid sequence has at least 80% identity with SEQ ID No. 1, SEQ ID No. 26, SEQ ID No. 27, SEQ ID No. 3, SEQ ID No 28, SEQ ID No. 29, or SEQ ID No. 5.

In one embodiment the parent or backbone amino acid sequence has at least 90% identity with SEQ ID No. 1, SEQ ID No. 26, SEQ ID No. 27, SEQ ID No. 3, SEQ ID No 28, SEQ ID No. 29, or SEQ ID No. 5.

In one embodiment the parent or backbone amino acid sequence has at least 95% identity with SEQ ID No. 1, SEQ ID No. 26, SEQ ID No. 27, SEQ ID No. 3, SEQ ID No 28, SEQ ID No. 29, or SEQ ID No. 5.

In one embodiment the parent or backbone amino acid sequence has at least 98% identity with SEQ ID No. 1, SEQ ID No. 26, SEQ ID No. 27, SEQ ID No. 3, SEQ ID No 28, SEQ ID No. 29, or SEQ ID No. 5.

In one embodiment the parent or backbone xylanase enzyme may be encoded by a nucleotide sequence comprising a nucleotide sequence having at least 80% identity with SEQ ID No. 2, SEQ ID No. 24, SEQ ID No. 25, SEQ ID No. 4, SEQ ID No. 30, SEQ ID No. 31, SEQ ID No. 6, SEQ ID No 32 or SEQ ID No. 33.

In one embodiment the parent or backbone xylanase enzyme may be encoded by a nucleotide sequence comprising a nucleotide sequence having at least 90% identity with SEQ ID No. 2, SEQ ID No. 24, SEQ ID No. 25, SEQ ID No. 4, SEQ ID No. 30, SEQ ID No. 31, SEQ ID No. 6, SEQ ID No 32 or SEQ ID No. 33.

In one embodiment the parent or backbone xylanase enzyme may be encoded by a nucleotide sequence comprising a nucleotide sequence having at least 95% identity with SEQ ID No. 2, SEQ ID No. 24, SEQ ID No. 25, SEQ ID No. 4, SEQ ID No. 30, SEQ ID No. 31, SEQ ID No. 6, SEQ ID No 32 or SEQ ID No. 33.

In one embodiment the parent or backbone xylanase enzyme may be encoded by a nucleotide sequence comprising a nucleotide sequence having at least 98% identity with SEQ ID No. 2, SEQ ID No. 24, SEQ ID No. 25, SEQ ID No. 4, SEQ ID No. 30, SEQ ID No. 31, SEQ ID No. 6, SEQ ID No 32 or SEQ ID No. 33.

Suitably, the parent or backbone GH10 xylanase may be obtainable (suitably obtained) from a *Fusarium* organism.

Suitably the parent or backbone xylanase is an endo-1,4-β-d-xylanase.

The modified xylanase or GH10 xylanase according to the present invention is preferably an endo-1,4-β-d-xylanase.

In a preferred embodiment, the enzyme having xylanase activity, e.g. the GH10 xylanase enzyme (such as the modified GH10 xylanase enzyme) or a fragment thereof according to the present invention has a Tm value of more than 70° C. (preferably more than 75° C.), wherein the Tm value is measured as the temperature at which 50% residual activity is obtained after 10 min incubation.

The thermostability of a xylanase (e.g. a modified xylanase) in accordance with the present invention may be determined using the "Assay for measurement of thermostability" (see below).

Assay for Measurement of Thermostability

The thermal denaturation profiles of the FveXyn4 variants was measured by diluting and pre-incubating the enzyme samples in 25 mM MES buffer, pH 6.0 for 10 min at varying temperatures (66, 66.7, 68.2, 70.6, 73.5, 76, 76.5, 76.8, 79.7, 81.9, 83.5, 84.6, and 85° C., respectively) and subsequently measuring the residual activity by the xylanase activity method described in Example 1. Activity measured without pre-incubation was set to 100% and the residual activity of each variant at each temperature was calculated as relative to this. Tm value is calculated from the thermal denaturation profiles as the temperature at which 50% residual activity is obtained.

In one embodiment, an enzyme is considered to be thermostable in accordance with the present invention if it has a Tm value of more than 70° C., wherein the Tm value is the temperature at which 50% residual activity is obtained after 10 min incubation. This Tm value may be measured in accordance with the assay for measurement of thermostability as taught herein.

In one embodiment, an enzyme is considered to be thermostable in accordance with the present invention if it has a Tm value of more than 76° C., wherein the Tm value is the temperature at which 50% residual activity is obtained after 10 min incubation. This Tm value may be measured in accordance with the assay for measurement of thermostability as taught herein.

In one embodiment, an enzyme is considered to be thermostable in accordance with the present invention if it has a Tm value of more than 85° C., wherein the Tm value is the temperature at which 50% residual activity is obtained after 10 min incubation. This Tm value may be measured in accordance with the assay for measurement of thermostability as taught herein.

Preferably, the enzyme having xylanase activity, e.g. the GH10 xylanase enzyme (such as the modified GH10 xylanase enzyme) or a fragment thereof according to the present invention (or composition comprising same) can withstand a heat treatment (e.g. during the pelleting process for example) of up to about 70° C.; e.g. up to 75° C., e.g. up to 76° C., e.g. up to about 85° C.; e.g. or up to about 95° C. The heat treatment may be performed for up to about 1 minute; up to about 5 minutes; up to about 10 minutes; up to about 30 minutes; up to about 60 minutes. To withstand such heat treatment means that at least about 50% of the enzyme that was present/active in the additive before heating to the specified temperature is still present/active after it cools to room temperature. Preferably, at least about 80% of the enzyme that is present and active in the additive before heating to the specified temperature is still present and active after it cools to room temperature.

The term "thermostability" is the ability of an enzyme to resist irreversible inactivation (usually by denaturation) at a relatively high temperature. This means that the enzyme retains a specified amount of enzymatic activity after exposure to an identified temperature over a given period of time.

There are many ways of measuring thermostability. By way of example, enzyme samples may be incubated without substrate for a defined period of time (e.g. 10 min or 1 to 30 min) at an elevated temperature compared to the temperature at which the enzyme is stable for a longer time (days). Following the incubation at elevated temperature the enzyme sample is assayed for residual activity at the permissive temperature of e.g. 30° C. (alternatively 25-50° C. or even up to 70° C.). Residual activity is calculated as relative to a sample of the enzyme that has not been incubated at the elevated temperature.

Thermostability can also be measured as enzyme inactivation as function of temperature. Here enzyme samples are incubated without substrate for a defined period of time (e.g. 10 min or 1 to 30 min) at various temperatures and following incubation assayed for residual activity at the permissive temperature of e.g. 30° C. (alternatively 25-70° C. or even higher). Residual activity at each temperature is calculated as relative to a sample of the enzyme that has not been incubated at the elevated temperature. The resulting thermal denaturation profile (temperature versus residual activity) can be used to calculate the temperature at which 50% residual activity is obtained. This value is defined as the Tm value.

Even further, thermostability can be measured as enzyme inactivation as function of time. Here enzyme samples are incubated without substrate at a defined elevated temperature (e.g. 76° C.) for various time periods (e.g. between 10 sec and 30 min) and following incubation assayed for residual activity at the permissive temperature of e.g. 30° C. (alternatively 25-70° C. or even higher). Residual activity at each temperature is calculated as relative to an enzyme sample that has not been incubated at the elevated temperature. The resulting inactivation profile (time versus residual activity) can be used to calculate the time at which 50% residual activity is obtained. This is usually given as T112.

These are examples of how to measure thermostability. Thermostability can also be measured by other methods. Preferably thermostability is assessed by use of the "Assay for measurement of thermostability" as taught herein.

In contradistinction to thermostability, thermoactivity is enzyme activity as a function of temperature. To determine thermoactivity enzyme samples may be incubated (assayed) for the period of time defined by the assay at various temperatures in the presence of substrate. Enzyme activity is obtained during or immediately after incubation as defined by the assay (e.g. reading an OD-value which reflects the amount of formed reaction product). The temperature at which the highest activity is obtained is the temperature optimum of the enzyme at the given assay conditions. The activity obtained at each temperature can be calculated relative to the activity obtained at optimum temperature. This will provide a temperature profile for the enzyme at the given assay conditions.

In the present application thermostability is not the same as thermoactivity.

Suitably the modified xylanase according to the present invention has a pH optimum in the range of 4.6 to 7, preferably about 5 to 6.

In a preferred embodiment, the modified xylanase according to the present invention comprises one of the amino acid sequences shown herein as SEQ ID No. 17, SEQ ID No. 18, SEQ ID No. 19, SEQ ID No. 20, or SEQ ID No. 21, or a fragment thereof having xylanase activity.

In one embodiment the modifications in the backbone polynucleotide sequence are such to render the above detailed modifications in the encoded amino acid sequence:

The methods of the present invention are suitable to render the modifications as taught above in the polynucleotide or amino acid sequence.

The host cell of the present invention may be selected from the group consisting of a bacterial cell, fungal cell, a yeast cell, a filamentous fungal cell and a plant cell. Preferably the host cell is a bacterial or fungal cell.

In one preferred embodiment the enzyme having xylanase activity, e.g. the GH10 xylanase enzyme (such as the modified GH10 xylanase enzyme) or a fragment thereof according to the present invention produced in accordance with a method of the present invention is recovered.

In one preferred embodiment the enzyme having xylanase activity, e.g. the GH10 xylanase enzyme (such as the modified GH10 xylanase enzyme) or a fragment thereof according to the present invention produced in accordance with a method of the present invention is isolated and/or purified.

In some embodiments the enzyme having xylanase activity, e.g. the GH10 xylanase enzyme (such as the modified GH10 xylanase enzyme) or a fragment thereof according to the present invention may be used directly as a fermentate without isolation and/or purification of the enzyme.

In some embodiments the feed additive composition according to the present invention or the premix according to the present invention further comprises one or more of the enzymes selected from the group consisting of a protease (e.g. subtilisin (E.C. 3.4.21.62) or a bacillolysin (E.C. 3.4.24.28) or an alkaline serine protease (E.C. 3.4.21.x) or a keratinase (E.C. 3.4.x.x)) and/or an amylase (including α-amylases (E.C. 3.2.1.1), G4-forming amylases (E.C. 3.2.1.60), β-amylases (E.C. 3.2.1.2) and γ-amylases (E.C. 3.2.1.3)).

The enzyme having xylanase activity, e.g. the GH10 xylanase enzyme (such as the modified GH10 xylanase enzyme) or a fragment thereof according to the present invention may be used in a method for degrading arabinoxylan-containing material in a xylan-containing material.

Suitably, the arabinoxylan may be insoluble arabinoxylan (AXinsol).

In one embodiment the xylan-containing material is selected from one or more of the group consisting of: a feed or feedstuff; a feed component; a grain-based material; a mash; a wort; a malt; malted barley; an adjunct, a barley mash; and a cereal flour.

In a preferred embodiment the arabinoxylans are solubilized without increasing viscosity in the reaction medium.

In one embodiment of the present invention the feed or feedstuff or feed component comprises or consists of corn, DDGS (such as cDDGS), wheat, wheat bran or a combination thereof.

In one preferred embodiment the feed or feedstuff is a corn-based feedstuff.

The enzyme having xylanase activity, e.g. the GH10 xylanase enzyme (such as the modified GH10 xylanase enzyme) or a fragment thereof according to the present invention according to the present invention may be used in combination with one or more of the enzymes selected from the group consisting of a protease (e.g. subtilisin (E.C. 3.4.21.62) or a bacillolysin (E.C. 3.4.24.28) or an alkaline serine protease (E.C. 3.4.21.x) or a keratinase (E.C. 3.4.x.x)) and/or an amylase (including α-amylases (E.C. 3.2.1.1), G4-forming amylases (E.C. 3.2.1.60), β-amylases (E.C. 3.2.1.2) and γ-amylases (E.C. 3.2.1.3)).

In one embodiment the method or use according to the present invention comprises administering a subject with an enzyme having xylanase activity, e.g. the GH10 xylanase enzyme (such as the modified GH10 xylanase enzyme) or a fragment thereof according to the present invention, or a fermentate comprising said enzyme according to the present invention, or an enzyme composition comprising said xylanase enzyme according to the present invention, or a feed additive composition comprising said xylanase enzyme according to the present invention, or a premix comprising said xylanase enzyme according to the present invention or a feedstuff comprising said xylanase enzyme according to the present invention.

In one embodiment the method or use of the present invention is (or is part of) a wheat gluten-starch separation process.

In another embodiment, the method or use of the present invention is (or is part of) a biofuel (e.g. bioethanol) or biochemical (e.g. bio-based isoprene) production process.

In another embodiment, the method or use of the present invention is (or is part of) a malting or brewing process.

Suitably, a fermented beverage, e.g. beer, produced by a method according to the present invention in envisaged by the present invention.

In one embodiment the parent xylanase enzyme of the present invention may be referred to herein as FveXyn4.

Both the polypeptide sequences and the nucleic acid sequences taught herein are preferably isolated.

The xylanase of the present invention is preferably a GH10 xylanase. In other words the xylanase may have a molecular weight in the range of 32-39 kDa and/or the catalytic domain of the xylanase consists of an eightfold β/α barrel structure (as taught in Harris et al 1996—Acta. Crystallog. Sec. D 52, 393-401).

In one aspect of the invention, the xylanase of the invention is a xylanase of Glycoside Hydrolyase (GH)

Family 10. The term "of Glycoside Hydrolyase (GH) Family 10" means that the xylanase in question is or can be classified in the GH family 10.

Protein similarity searches (e.g. protein blast at http://blast.ncbi.nlm.nih.gov/Blast.cgi?CMD=Web&PAGE_TYPE=BlastHome) may determine whether an unknown sequence falls under the term of a OHIO xylanase family member, particularly the GH families may be categorised based on sequence homology in key regions. In addition or alternatively, to determine whether an unknown protein sequence is a xylanase protein within the GH10 family, the evaluation can be done, not only on sequence similarity/homology/identity, but also on 3D structure similarity. The classification of GH-families is often based on the 3D fold. Software that will predict the 3D fold of an unknown protein sequence is HHpred (http://toolkit.tuebingen.mpg.de/hhpred). The power of this software for protein structure prediction relies on identifying homologous sequences with known structure to be used as template. This works so well because structures diverge much more slowly than primary sequences. Proteins of the same family may have very similar structures even when their sequences have diverged beyond recognition.

In practice, an unknown sequence can be pasted into the software (http://toolkit.tuebingen.mpg.de/hhpred) in FASTA format. Having done this, the search can be submitted. The output of the search will show a list of sequences with known 3D structures. To confirm that the unknown sequence indeed is a GH10 xylanase, GH10 xylanases may be found within the list of homologues having a probability of >90. Not all proteins identified as homologues will be characterised as GH10 xylanases, but some will. The latter proteins are proteins with a known structure and biochemically characterisation identifying them as xylanases. The former have not been biochemically characterised as GH10 xylanases. Several references describes this protocol such as Söding J. (2005) Protein homology detection by HMM-HMM comparison—Bioinformatics 21, 951-960 (doi: 10.1093/bioinformatics/bti125) and Söding J, Biegert A, and Lupas A N. (2005) The HHpred interactive server for protein homology detection and structure prediction—Nucleic Acids Research 33, W244-W248 (Web Server issue) (doi: 10.1093/nar/gki40).

According to the Cazy site (http://www.cazy.org/), Family 10 glycoside hydrolases can be characterised as follows:

Known Activities: endo-1,4-β-xylanase (EC 3.2.1.8); endo-1,3-β-xylanase (EC 3.2.1.32); tomatinase (EC 3.2.1.-)

Mechanism: Retaining

Clan: GH-A

Catalytic Nucleophile/Base: Glu (experimental)

Catalytic Proton Donor: Glu (experimental)

3D Structure Status: $(\beta/\alpha)_8$

The GH10 xylanase of the present invention may have a catalytic domain with molecular weights in the range of 32-39 kDa. The structure of the catalytic domain of the GH10 xylanase of the present invention consists of an eightfold β/α barrel (Harris et al 1996—Acta. Crystallog. Sec. D 52, 393-401).

Three-dimensional structures are available for a large number of Family GH10 enzymes, the first solved being those of the *Streptomyces lividans* xylanase A (Derewenda et al J Biol Chem 1994 Aug. 19; 269(33) 20811-4), the *C. fimi* endo-glycanase Cex (White et al Biochemistry 1994 Oct. 25; 33(42) 12546-52), and the *Cellvibrio japonicus* Xyn10A (previously *Pseudomonas fluorescens* subsp. xylanase A) (Harris et al Structure 1994 Nov. 15; 2(11) 1107-16.). As members of Clan GHA they have a classical $(\alpha/\beta)_8$ TIM barrel fold with the two key active site glutamic acids located at the C-terminal ends of beta-strands 4 (acid/base) and 7 (nucleophile) (Henrissat et al *Proc Natl Acad Sci USA* 1995 Jul. 18; 92(15) 7090-4).

The term "GH10 xylanase" as used herein means a polypeptide having xylanase activity and having a $(\alpha/\beta)_8$ TIM barrel fold with the two key active site glutamic acids located at the C-terminal ends of beta-strands 4 (acid/base) and 7 (nucleophile).

The backbone (or parent) xylanase enzyme used herein may be referred to as FveXyn4 or FoxXyn 2 (these terms refer to the active proteins, e.g. the mature proteins).

In one embodiment preferably the xylanase is a fungal xylanase.

The enzyme having xylanase activity, e.g. the GH10 xylanase enzyme (such as the modified GH10 xylanase enzyme) or a fragment thereof according to the present invention and/or parent enzyme is a GH10 xylanase.

In one embodiment preferably the enzyme having xylanase activity, e.g. the GH10 xylanase enzyme (such as the modified GH10 xylanase enzyme) or a fragment thereof according to the present invention (and/or parent xylanase) is a fungal GH10 xylanase.

In one embodiment preferably the enzyme having xylanase activity, e.g. the GH10 xylanase enzyme (such as the modified GH10 xylanase enzyme) or a fragment thereof according to the present invention (and/or parent xylanase) is an endoxylanase, e.g. an endo-1,4-β-d-xylanase. The classification for an endo-1,4-β-d-xylanase is E.C. 3.2.1.8.

In some embodiments the enzyme having xylanase activity, e.g. the GH10 xylanase enzyme (such as the modified GH10 xylanase enzyme) or a fragment thereof of the present invention has an optimum pH at about 6.

Preferably the enzyme having xylanase activity, e.g. the GH10 xylanase enzyme (such as the modified GH10 xylanase enzyme) or a fragment thereof according to the present invention retains greater than 70% of maximum activity between pH4 and 8, suitably between pH 4.6 and 7.

In some embodiments, e.g. in feed applications, the enzyme having xylanase activity, e.g. the GH10 xylanase enzyme (such as the modified GH10 xylanase enzyme) or a fragment thereof according to the present invention preferably retains greater than 70% of maximum activity between 5.1 and 7.

Without wishing to be bound by theory, pH may also have an important effect on enzyme efficacy and efficiency. For feed applications in particular the pH profile of the xylanases of the present invention favor activity in the small intestine, under neutral conditions.

In one embodiment, the enzyme having xylanase activity, e.g. the GH10 xylanase enzyme (such as the modified GH10 xylanase enzyme) or a fragment thereof according to the present invention is capable of degrading (or degrades) a xylan-containing material, particularly arabinoxylans, particularly insoluble arabinoxylans (AXinsol).

In another embodiment the enzyme having xylanase activity, e.g. the GH10 xylanase enzyme (such as the modified GH10 xylanase enzyme) or a fragment thereof according to the present invention is capable of degrading (or degrades) soluble polymers (e.g. oligomers) that are produced from degradation of AXinsol or that are (naturally) present in grain-based material.

In a further embodiment the enzyme having xylanase activity, e.g. the GH10 xylanase enzyme (such as the modified GH10 xylanase enzyme) or a fragment thereof according to the present invention is capable of degrading (or degrades) both a xylan-containing material, particularly arabinoxylans, particularly AXinsol, and soluble polymers (e.g. oligomers) that are produced from degradation of AXinsol.

In one embodiment the enzyme having xylanase activity, e.g. the GH10 xylanase enzyme (such as the modified GH10 xylanase enzyme) or a fragment thereof according to the present invention are unaffected by wheat xylanases inhibitors, e.g. proteinaceous inhibitors, e.g. TAXI-like proteinaceous inhibitors in wheat. Prior art fungal xylanases can be inhibited by as much as 70-95% by wheat proteinaceous inhibitors. Preferably the xylanases of the present invention are only inhibited by 20-30% at most in wheat applications.

TAXI are *Triticum aestivum* xylanases inhibitors, present in cereals.

The term "consisting essentially of" as used herein means that unspecified components may be present if the characteristics of the claimed composition are thereby not materially affected.

The term "consisting of" means that the proportions of the specific ingredients must total 100%.

The term "comprising" used herein may be amended in some embodiments to refer to consisting essentially of or consisting of (both having a more limited meaning that "comprising").

In one embodiment the insoluble arabinoxylan containing material is not wheat straw.

The term "fragment thereof" as used herein means an active fragment. In other words the fragment is one which has xylanase activity. Suitably the fragment may have the same xylanase activity as the full length modified GH10 xylanase enzyme from which the fragment is derived. Alternatively, the fragment may have a modified activity (e.g. enhanced specificity, specific activity, pH or temperature profile) compared with the full length modified GH10 xylanase enzyme from which the fragment is derived. In addition the fragment must retain the thermostable properties of the modified GH10 xylanase enzyme of which it is a fragment.

In one embodiment the fragment is at least 60% of the full length of the modified GH10 xylanase enzyme from which the fragment is derived.

In one embodiment the fragment is at least 75% of the full length of the modified GH10 xylanase enzyme from which the fragment is derived.

In one embodiment the fragment is at least 85% of the full length of the modified GH10 xylanase enzyme from which the fragment is derived.

In one embodiment the fragment is at least 95% of the full length of the modified GH10 xylanase enzyme from which the fragment is derived.

In one embodiment the fragment is at least 98% of the full length of the modified GH10 xylanase enzyme from which the fragment is derived.

In one embodiment the fragment is a fragment of one or more of the sequences selected from the group consisting of SEQ ID No. 17, SEQ ID No. 18, SEQ ID No. 19, SEQ ID No. 20, or SEQ ID No. 21.

In one embodiment the enzyme having xylanase activity, e.g. the GH10 xylanase enzyme (such as the modified GH10 xylanase enzyme) or a fragment, thereof according to the present invention a) comprises one of the amino acid sequences shown herein as SEQ ID No. 17, SEQ ID No. 18, SEQ ID No. 19, SEQ ID No. 20, or SEQ ID No. 21, or b) comprises an amino acid sequence which is at least 96%, preferably at least 98.5%, identical with the amino acid sequences shown herein as SEQ ID No. 17, SEQ ID No. 18, SEQ ID No. 19, SEQ ID No. 20, or SEQ ID No. 21 so long as the amino acids at positions 7, 33, 79, 217 and 298 are identical with those shown in SEQ ID No. 17, SEQ ID No. 18, SEQ ID No. 19, SEQ ID No. 20, or SEQ ID No. 21.

In one embodiment the present invention provides a nucleic acid molecule according to the present invention or a vector or construct comprising same, wherein the nucleotide sequence is selected from the group consisting of: SEQ ID No. 7, SEQ ID No. 8, SEQ ID No. 9, SEQ ID No. 10, SEQ ID No. 11, SEQ ID No. 12. SEQ ID No. 13, SEQ ID No. 14, SEQ ID No. 15 and SEQ ID No. 16; or a nucleotide sequence which is at least 96%, preferably 98.5%, identical with the nucleotide sequences shown herein as SEQ ID No. 7, SEQ ID No. 8, SEQ ID No. 9, SEQ ID No. 10, SEQ ID No. 11, SEQ ID No. 12. SEQ ID No. 13, SEQ ID No. 14, SEQ ID No. 15 or SEQ ID No. 16 so long as the codons encoding amino acid positions 7, 33, 79, 217 and 298 in the mature protein the same as those of SEQ ID No. 7, SEQ ID No. 8, SEQ ID No. 9, SEQ ID No. 10, SEQ ID No. 11, SEQ ID No. 12. SEQ ID No. 13, SEQ ID No. 14, SEQ ID No. 15 or SEQ ID No. 16.

The term "modifying" as used herein means changing or altering. In particular, the term "modifying" as used herein means altering from the naturally occurring. In other words, when modifying the enzyme, one changes the enzyme in such a way that renders the enzyme altered from the parent backbone enzyme. Preferably the modified enzyme does not exist itself in nature. Thus the modified enzyme is a non-naturally-occurring enzyme.

The term "modified" as used herein means altered, e.g. from its naturally occurring form. The modified enzymes according to the present invention are preferably not naturally occurring enzymes or naturally occurring variants. In other words, the modified enzymes according to the present invention are preferably modified enzymes that have not been found in nature. The modified enzymes of the present invention have preferably not occurred spontaneously.

In some embodiments the enzyme having xylanase activity, e.g. the GH10 xylanase enzyme (such as the modified GH10 xylanase enzyme) or a fragment thereof of the present invention is prepared by modifying a parent enzyme or a backbone enzyme. However in other embodiments the enzyme having xylanase activity, e.g. the GH10 xylanase enzyme (such as the modified GH10 xylanase enzyme) or a fragment thereof of the present invention is prepared without modifying a parent enzyme or a backbone enzyme, e.g. it may be prepared synthetically. The term "modified xylanase" or "modified GH10 xylanase" as used herein does not dictate that the xylanase has been prepared by mutating a parent enzyme. The modified xylanase may suitably have been prepared by other means, e.g. synthetically.

Uses

The enzyme having xylanase activity, e.g. the GH10 xylanase enzyme (such as the modified GH10 xylanase enzyme) or a fragment thereof of the present invention can be suitably used in any one of the following applications:

a) An additive in animal feedstuffs; and/or
b) A feed supplement for an animal; and/or
c) Breakdown of grain-based material (e.g. this can be whole grain or part of grain). The breakdown products (e.g. glucose) can be used as a feedstock for any fermentation process, such as in biofuel (e.g. bioethanol) production or in the production of other products such as biochemicals (e.g., bio-based isoprene). Therefore in one embodiment the present invention relates to the production of biofuel (e.g. bioethanol) and to the enhanced utilisation of grain-based material in the biofuel industry; and/or d) Cereal (e.g. wheat) gluten-starch separation industry. The resultant product(s) may be starch (e.g. purified starch) and/or gluten and/or fibres and/or water solubles (such as soluble pentosans). In one embodiment the present invention relates to the production of starch and/or gluten; and/or
e) Improving malting and brewing, e.g. by breaking down grain-based material (e.g. malted barley) and/or
f) to degrade AXsol or the breakdown products of AXinsol to ensure viscosity is not increased and/or viscosity is reduced in the reaction mixture;
g) to reducing viscosity when degrading grain-based materials, e.g. in biofuel (e.g. bioethanol) production processes.

In one embodiment the enzyme having xylanase activity, e.g. the GH10 xylanase enzyme (such as the modified GH10 xylanase enzyme) or a fragment thereof of the present invention is used in a feedstuff. Preferably a feedstuff comprising corn or is a corn-based feedstuff.

In one embodiment the enzyme having xylanase activity, e.g. the GH10 xylanase enzyme (such as the modified GH10 xylanase enzyme) or a fragment thereof of the present invention is used in malting or brewing.

In a further embodiment the enzyme having xylanase activity, e.g. the GH10 xylanase enzyme (such as the modified GH10 xylanase enzyme) or a fragment thereof of the present invention is used in wheat gluten-starch separation.

In a yet further embodiment the enzyme having xylanase activity, e.g. the GH10 xylanase enzyme (such as the modified GH10 xylanase enzyme) or a fragment thereof of the present invention is used in the breakdown of grain-based material and may be part of the biofuel (e.g. bioethanol) production process.

Advantages

The novel enzyme having xylanase activity, e.g. the GH10 xylanase enzyme (such as the modified GH10 xylanase enzyme) or a fragment thereof taught herein has many advantages compared with known xylanases.

The enzyme having xylanase activity, e.g. the GH10 xylanase enzyme (such as the modified GH10 xylanase enzyme) or a fragment thereof of the present invention is thermostable. For example the enzyme having xylanase activity, e.g. the GH10 xylanase enzyme (such as the modified GH10 xylanase enzyme) or a fragment thereof of the present invention is significantly more stable than the parent (backbone) xylanase before modification. Suitably the modified xylanase has a Tm value of more than 70° C. (preferably more than 75° C.), wherein the Tm value is measured as the temperature at which 50% residual activity is obtained after 10 min incubation.

The enzyme having xylanase activity, e.g. the GH10 xylanase enzyme (such as the modified GH10 xylanase enzyme) or a fragment thereof of the present invention are also unexpectedly good at solubilising pentosans.

The enzyme having xylanase activity, e.g. the GH10 xylanase enzyme (such as the modified GH10 xylanase enzyme) or a fragment thereof of the present invention are unexpectedly good at solubilising AXinsol.

Surprisingly it has been found that the enzyme having xylanase activity, e.g. the GH10 xylanase enzyme (such as the modified GH10 xylanase enzyme) or a fragment thereof of the present invention is particularly good at degrading xylan-containing materials, such as arabinoxylans, e.g. AXinsol, in a broad spectrum of substrates, corn, wheat, DDGS, etc., in particular corn and corn based substrates, in particular both wheat (including wheat-based) products and corn (including corn-based products). Compared with the benchmark xylanases which are all commercially produced and marketed xylanases, the novel xylanase taught herein was capable of much more efficient degradation and pentosan release from more plant based materials (in particular corn-based substrates) compared with the marketed xylanases. This was completely unexpected. This contrasts with prior-known enzymes, which are often inferior at solubilising AXinsol in corn or corn-based substrates or which are not as efficient in both wheat- and corn-based substrates.

In addition, the enzyme having xylanase activity, e.g. the GH10 xylanase enzyme (such as the modified GH10 xylanase enzyme) or a fragment thereof, of the present invention is particularly good at not only breaking down (solubilising) AXinsol, but also breaking down (or degrading) the solubilized polymers efficiently. By being able to efficiently (quickly) breakdown (degrade) the solubilized polymers (obtained from dissolving AXinsol) a reduction in viscosity is obtained. This latter effect is essential in some of the claimed applications.

Typically, conventional xylanases may breakdown AXinsol, but will lead to an increase is the polymer production products which will lead to an increase in viscosity of the mixture. This increased viscosity is disadvantageous in many applications.

The enzyme having xylanase activity, e.g. the GH10 xylanase enzyme (such as the modified GH10 xylanase enzyme) or a fragment thereof, of the present invention and as described herein have been found to not only breakdown (solubilise) insoluble arabinoxylans (AXinsol) from a wide range of substrates, including corn, wheat, DDGS, etc., in particular corn and corn-based substrates, in particular both wheat (including wheat-based) products and corn (including corn-based products), but also efficiently breakdown the thus solubilised polymers to ensure viscosity is not raised and/or to reduce viscosity.

The enzyme having xylanase activity, e.g. the GH10 xylanase enzyme (such as the modified GH10 xylanase enzyme) or a fragment thereof, of the present invention and as described herein are capable of degrading AXsol or the breakdown products of AXinsol to ensure viscosity is not increased and/or viscosity is reduced in the reaction mixture.

Many of the xylanases commercialized for use in feedstuffs for solubilizing pentosans are GH11 enzymes. It had been considered by those skilled in the art that GH10 xylanases were not as strong at solubilizing pentosans, particularly AXinsol, compared with GH11 xylanases. Surprisingly it has been found that the novel modified xylanase(s) disclosed herein which is a/are GH10 xylanase(s) is/are particularly good at solubilizing AXinsol in a broad spectrum of substrates, including corn based substrates. Surprisingly, the present inventors have found that the modified GH10 xylanases of the present invention (and taught herein) outperform commercial GH11 xylanases in their ability to solubilize pentosans.

The fact that the present enzymes efficiently solubilize AXinsol from corn and corn-based substrates is significantly advantageous as corn holds much more AX in the insoluble form compared with other cereals, such as wheat and rye for example. Therefore only xylanases that can breakdown AXinsol can show significant benefit to animals fed on corn-soy diet for example.

It was completely unexpected for a GH10 xylanase to be so good on solubilizing AXinsol in cereals, particularly in corn or corn-based substrates.

The enzymes of the present invention are able to efficiently (and quickly) degrade the polymers and/or oligomers that are produced from solubilisation of AXinsol or that are present in grain-based materials. This leads to an unexpected advantage for the modified GH10 xylanases taught herein in that they are particularly good in a number of applications to keep viscosity low or to reduce viscosity, e.g. in feedstuffs; in brewing and/or malting; in grain-based production of glucose, e.g. for further processing to biofuels and/or biochemicals (e.g., bio-based isoprene); or in the wheat gluten-starch separation industry for the production of starch for example.

In addition, the modified GH10 xylanase of the present invention is particularly thermostable. This provides significant advantages in some applications. In particular, in feed applications, enzymes can be subject to heat treatment, e.g. during pelleting processes. Thus the enzymes need to be able to maintain their activity after such processing. The modified xylanases of the present invention are particularly and unexpectedly thermostable.

Furthermore, an improved thermostability is also very beneficial during degradation of starch, which takes place at elevated temperatures during liquefaction (around 85-95 C). Being thermostable allows the addition of the enzyme during this step.

Notably it has been found that the degradation product from use of the modified xylanase on average is shorter for the GH10 enzymes tested herein compared with GH11 enzymes. This enhances the lowering of viscosity effect.

In addition, a further advantage of the enzyme having xylanase activity, e.g. the GH10 xylanase enzyme (such as the modified GH10 xylanase enzyme) or a fragment thereof, of the present invention (unlike many GH11 xylanases) are unaffected by wheat xylanase inhibitors, e.g. TAXI like proteinaceous inhibitors, which occur in wheat.

One advantage of the present invention is that it improves wheat gluten-starch separation.

The enzyme of the present invention is particularly effective at enhancing the performance of a subject or improving the digestibility of a raw material in a feed and/or for improving feed efficiency in a subject.

Xylan-Containing Material

The enzyme having xylanase activity, e.g. the GH10 xylanase enzyme (such as the modified GH10 xylanase enzyme) or a fragment thereof, of the present invention (or composition comprising the modified xylanase of the present invention) may be used to degrade any xylan-containing material.

In one embodiment the xylan-containing material is any plant material comprising arabinoxylan.

In one embodiment the xylan-containing material is any plant material comprising insoluble arabinoxylan (AXinsol).

In one embodiment the xylan-containing material is a feedstuff or feed component.

In one embodiment the xylan-containing material is a grain-based material (including whole grains or partial grains or malted grains, e.g. malted barley). When the method relates to biofuel production (e.g. bioethanol production) then preferably the xylan-containing material is a grain-based material.

In another embodiment the xylan-containing material may be a barley malt or mash, or malted barley or combinations thereof.

In a yet further embodiment the xylan-containing material may be a cereal flour (e.g. wheat, oat, rye or barley flour). When the method relates to a gluten-starch separation process preferably the xylan-containing material is a cereal flour (e.g. wheat oat, rye or barley flour).

Breakdown or Degradation

The enzyme having xylanase activity, e.g. the GH10 xylanase enzyme (such as the modified GH10 xylanase enzyme) or a fragment thereof, of the present invention (or composition comprising the enzyme) may be used to breakdown (degrade) AXinsol or AXsol or degradation products of AXinsol.

The term "breakdown" or "degrade" in synonymous with hydrolyses.

Solubilisation/Degradation

The present invention relates to a method of degrading a xylan-containing material (preferably an arabinoxylan-containing material, preferably an insoluble arabinoxylan (AXinsol)-containing material) to produce soluble pentosans (which can be polymeric, oligomeric or monomeric).

This method may be described herein as pentosan solubilisation or arabinoxylan solubilisation or AXinsol solubilisation or degradation of AXinsol.

In one embodiment, the present invention relates to a method of degrading (or breaking down) insoluble arabinoxylan (AXinsol). This can also be referred to as solubilisation of insoluble arabinoxylan and/or solubilisation of pentosans.

In a further embodiment of the present invention the method relates to degrading (e.g. breaking down) polymers derived from the degradation of insoluble arabinoxylans.

Arabinoxylan (AX)

The term "arabinoxylans" (AX) as used herein means a polysaccharide consisting of a xylan backbone (1,4-linked xylose units) with L-arabinofuranose (L-arabinose in its 5-atom ring form) attached randomly by $1\alpha \rightarrow 2$ and/or $1\alpha \rightarrow 3$ linkages to the xylose units throughout the chain. Arabinoxylan is a hemicellulose found in both the primary and secondary cell walls of plants. Arabinoxylan can be found in the bran of grains such as wheat, maize (corn), rye, and barley.

Arabinoxylan (AX) is found in close association with the plant cell wall, where it acts as a glue linking various building blocks of the plant cell wall and tissue, give it both structural strength and rigidity.

The term "pentosan" as used herein is any of a group of carbohydrates which yield pentoses on complete hydrolysis. Since xylose and arabinose (the constituents of arabinoxylans) are both pentoses, arabinoxylans are usually classified as pentosans.

AX is the principal Non Starch Polysaccharide (NSP)-fraction in several of the most important feed raw material, including wheat and corn.

Its abundance, location within vegetable material and molecular structure cause AX to have a severe, negative impact on feed digestibility, effectively reducing the nutritional value of the raw materials in which it is present. This makes AX an important anti-nutritional factor, reducing animal production efficiency.

In addition AX can have a severe, negative impact when trying to breakdown plant material for example in processes such as brewing, malting, biofuel manufacture, effectively reducing the amount of substrate accessible in the raw plant material.

AXs can also hold substantial amounts of water (which can be referred to as their water holding capacity)—this can cause soluble arabinoxylans to result in (high) viscosity—which is a disadvantage in many applications.

The term "Hemicellulose"—as used herein means the polysaccharide components of plant cell walls other than cellulose. The term "hemicellulose" as used herein may mean polysaccharides in plant cell walls which are extractable by dilute alkaline solutions. Hemicelluloses comprise almost one-third of the carbohydrates in woody plant tissue. The chemical structure of hemicelluloses consists of long chains of a variety of pentoses, hexoses, and their corresponding uronic acids. Hemicelluloses may be found in fruit, plant stems, and grain hulls. Xylan is an example of a pentosan consisting of D-xylose units with 1β→4 linkages.

Water Insoluble Arabinoxylan (AXinsol)

Water-insoluble arabinoxylan (AXinsol) also known as water-unextractable arabinoxylan (WU-AX) constitutes a significant proportion of the dry matter of plant material.

In wheat AXinsol can account for 6.3% of the dry matter. In wheat bran and wheat DDGS AXinsol can account for about 20.8% or 13.4% of the dry matter (w/w).

In rye AXinsol can account for 5.5% of the dry matter.

In corn AXinsol can account for 3.5-6% (e.g. 5.1%) of the dry matter. In corn DDGS AXinsol can account for 10-20% (e.g. 12.6%) of the dry matter.

AXinsol causes nutrient entrapment in feed. Large quantities of well digestible nutrients such as starch and proteins remain either enclosed in clusters of cell wall material or bound to side chains of the AX. These entrapped nutrients will not be available for digestion and subsequent absorption in the small intestine.

Water-Soluble Arabinoxylan (AXsol)

Water-soluble arabinoxylan (AXsol) also known as water extractable arabinoxylan (WE-AX) can cause problems in biofuel production, biochemical production, carbohydrate processing and/or malting and/or brewing and/or in feed as they can cause increased viscosity due to the water-binding capacity of AXsol.

In feed AXsol can have an anti-nutritional effect particularly in monogastrics as they cause a considerable increase of the viscosity of the intestinal content, caused by the extraordinary water-binding capacity of AXsol. The increase viscosity can affect feed digestion and nutrient use as it can prevent proper mixing of feed with digestive enzymes and bile salts and/or it slows down nutrient availability and absorption and/or it stimulates fermentation in the hindgut.

In wheat AXsol can account for 1.8% of the dry matter. In wheat bran and wheat DDGS AXsol can account for about 1.1% or 4.9% of the dry matter (w/w).

In rye AXsol can account for 3.4% of the dry matter.

In barley AXsol can account for 0.4-0.8% of the dry matter.

In corn AXsol can account for 0.1-0.4% (e.g. 0.1%) of the dry matter. In corn DDGS AXinsol can account for 0.3-2.5% (e.g. 0.4%) of the dry matter.

In addition, however, to the amount of AXsol present in plant material, when a xylanase solubilises AXinsol in the plant material this can release pentosans and/or oligomers which contribute to AXsol content of the plant material.

One significant advantage of the modified xylanases disclosed herein is that they have the ability to solubilise AXinsol without increasing viscosity. It is presently believed that high molecular weight products are not formed A breakdown of AXsol can decrease viscosity.

A breakdown of AXsol can release nutrients.

Viscosity

The present invention can be used to ensure that the viscosity is not increased and/or to reduce viscosity in any process where the water-binding capacity of AXsol causes an undesirable increase in viscosity.

The present invention relates to ensuring that viscosity is not increased and/or to reducing viscosity by breaking down (degrading) AXsol or by breaking down (degrading) the polymers and/or oligomers produced by solubilising AXinsol.

Without wishing to be bound by theory, by being able to efficiently (quickly) breakdown (degrade) the solubilized polymers (e.g. oligomers) obtained from dissolving AXinsol an undesirable increase in viscosity can be avoided and/or a reduction in viscosity can be obtained. The term "efficiently" as used herein means that the enzyme is capable of degrading the polymers (e.g. oligomers) being formed by solubilisation of the AXinsol faster than the speed with which the AXinsol is degraded (or solubilized).

Reducing viscosity has advantages in many applications as taught herein.

An in vitro assay which attempts to mimic the environment in the small intestine of a chicken was originally described by Bedford & Classen (1993 Poultry Sci., 72, 137-143). The assay consists of a two step incubation of the feed first at low pH with pepsin followed by incubation with pancreatin at neutral pH. It is generally accepted that the viscosity of the supernatant after end incubation correlates with the viscosity created in vivo in broilers.

Without increasing viscosity and/or a reduction in viscosity as taught herein for feed applications means that addition of the xylanase will result in an unchanged or lower viscosity measured by the method described in Example 1. By unchanged it is meant that the measured value, being the average of three repetitions, falls within two standard deviation of the measured value for a wheat sample without xylanase addition.

Viscosity can be measured using the following devices: Rapid ViscoAnalyzer (RVA) (e.g. in bioethanol processing) and Haake VT550 viscometer (Thermofisher) (e.g. is wheat-gluten starch processing). Both devices can monitor viscosity profiles of fuel ethanol processes and wheat starch separation processes, of which the experimental conditions are taught in Example 6 and 7, respectively.

In the present invention a reduction in viscosity can be calculated by comparing one sample comprising the xylanase of the present invention (or taught herein) compared with another comparable sample without the xylanase of the present invention (or taught herein).

Comparing the viscosity reduction profiles of the xylanase of the present invention with those of the market benchmark xylanase(s) demonstrates the enzyme performance. The aim is to improve enzyme performance compared to the market benchmark. The benchmark enzyme(s) for the individual applications are provided in the examples below.

The benchmark enzyme for comparing viscosity reduction in feed applications may be Econase® XT.

An example of a xylanase used in the bioethanol industry is Xylathin™.

An example of a Xylanase used in the wheat gluten-starch separation Industry is Shearzyme™.

The benchmark enzyme for review of thermostability may be the parent (backbone) xylanase (e.g. before modification).

In one embodiment of the present invention the xylanases taught herein are viscosity reducers.

Generally, wheat (or other cereal) is first dry-milled to separate the bran and germ from the endosperm, which is ground into flour. This endosperm flour is then further fractionated through a wheat starch separation process into several product streams of varying commercial value. The major aim is to produce a refined grade of A-starch, consisting of large, lenticular granules of 15-40 µm. The second stream B-starch consists of less purified starch granules, which are spherical and small (1-10 µm). (C. C. Maningat, P. A. Seib, S. D. Bassi, K. S. Woo, G. D. Lasater, Chapter 10 from the book "*Starch*" (2009) 441-451, *Wheat starch: production, properties, modification and uses*). Isolated wheat starch forms the starting material for modified starch production with applications in both food- and nonfood-applications. Vital gluten is the third product of added-value in wheat separation processes.

The vitality of the isolated wheat gluten is determined by the ability to form viscoelastic networks, required for bread-making. Vital gluten encapsulate the carbon dioxide formed in dough preparation during baking, and consequently increase the bread volume. (Anne van der Borght, Hans Goesaert, Wim S. Veraverbeke, Jan A. Delcour, *Journal of Cereal Science* 41 (2005) 221-237, Fractionation of wheat and wheat flour into starch and gluten: overview of the main processes and the factors involved.) It is therefore often used to enrich flours for bread making, to achieve improved bread products. Other markets for gluten include as an additive in vegetarian, meat, fish or poultry products, including those in pet-food industry; in cereal breakfast; or in soy sauce. Due to its thermoplasticity and good film-forming properties, gluten is also used in non-food markets as adhesives. (L. Day, M. A. Augustin, I. L. Batey, C. W. Wrigley, *Trends in Food Science & Technology* 17 (2006) 82-90, *Wheat-gluten uses and industry needs*.).

The modified xylanases taught herein can be used to reduce the viscosity (or not increase viscosity) in processes for separating cereal flour (e.g. wheat, oat, rye or barley flour) into starch and gluten fractions and to improve the separation by degrading oligosaccharides that hinder gluten agglomeration.

Wort viscosity, and the viscosity of barley mash and barley malt in brewing and malting can cause significant disadvantages during brewing and/or malting. The present invention relates to reducing the viscosity (or not increase the viscosity) of wort, barley mash, barley malt or a combination thereof.

Feed or Feedstuff

The enzyme having xylanase activity, e.g. the GH10 xylanase enzyme (such as the modified GH10 xylanase enzyme) or a fragment thereof, of the present invention or feed additive composition of the present invention may be used as—or in the preparation of—a feed.

The term "feed" is used synonymously herein with "feedstuff".

Preferably the arabinoxylan-containing material of the present invention is a feedstuff, or a constituent of a feedstuff, or a feed component.

The feed may be in the form of a solution or as a solid or as a semi-solid—depending on the use and/or the mode of application and/or the mode of administration.

When used as—or in the preparation of—a feed—such as functional feed—the enzyme or composition of the present invention may be used in conjunction with one or more of: a nutritionally acceptable carrier, a nutritionally acceptable diluent, a nutritionally acceptable excipient, a nutritionally acceptable adjuvant, a nutritionally active ingredient.

In a preferred embodiment the enzyme or feed additive composition of the present invention is admixed with a feed component to form a feedstuff.

The term "feed component" as used herein means all or part of the feedstuff. Part of the feedstuff may mean one constituent of the feedstuff or more than one constituent of the feedstuff, e.g. 2 or 3 or 4. In one embodiment the term "feed component" encompasses a premix or premix constituents.

Preferably the feed may be a fodder, or a premix thereof, a compound feed, or a premix thereof. In one embodiment the feed additive composition according to the present invention may be admixed with a compound feed, a compound feed component or to a premix of a compound feed or to a fodder, a fodder component, or a premix of a fodder.

The term "fodder" as used herein means any food which is provided to an animal (rather than the animal having to forage for it themselves). Fodder encompasses plants that have been cut.

The term fodder includes silage, compressed and pelleted feeds, oils and mixed rations, and also sprouted grains and legumes.

Fodder may be obtained from one or more of the plants selected from: corn (maize), alfalfa (Lucerne), barley, birdsfoot trefoil, brassicas, Chau moellier, kale, rapeseed (canola), rutabaga (swede), turnip, clover, alsike clover, red clover, subterranean clover, white clover, fescue, brome, millet, oats, sorghum, soybeans, trees (pollard tree shoots for tree-hay), wheat, and legumes.

The term "compound feed" means a commercial feed in the form of a meal, a pellet, nuts, cake or a crumble. Compound feeds may be blended from various raw materials and additives. These blends are formulated according to the specific requirements of the target animal.

Compound feeds can be complete feeds that provide all the daily required nutrients, concentrates that provide a part of the ration (protein, energy) or supplements that only provide additional micronutrients, such as minerals and vitamins.

The main ingredients used in compound feed are the feed grains, which include corn, wheat, canola meal, rapeseed meal, lupin, soybeans, sorghum, oats, and barley.

Suitably a premix as referred to herein may be a composition composed of microingredients such as vitamins, minerals, chemical preservatives, antibiotics, fermentation products, and other essential ingredients. Premixes are usually compositions suitable for blending into commercial rations.

Any feedstuff of the present invention may comprise one or more feed materials selected from the group comprising a) cereals, such as small grains (e.g., wheat, barley, rye, oats, triticale and combinations thereof) and/or large grains such as maize or sorghum; b) by products from cereals, such as corn gluten meal, wet-cake (particularly corn based wet-cake), Distillers Dried Grain (DDG) (particularly corn based Distillers Dried Grain (cDDG)), Distillers Dried Grain Solubles (DDGS) (particularly corn based Distillers Dried Grain Solubles (cDDGS)), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

In one embodiment the feedstuff comprises or consists of corn, DDGS (such as cDDGS), wheat, wheat bran or a combination thereof.

In one embodiment the feed component may be corn, DDGS (e.g. cDDGS), wheat, wheat bran or a combination thereof.

In one embodiment the feedstuff comprises or consists of corn, DDGS (such as cDDGS) or a combination thereof.

In one embodiment a feed component may be corn, DDGS (such as cDDGS) or a combination thereof.

A feedstuff of the present invention may contain at least 30%, at least 40%, at least 50% or at least 60% by weight corn and soybean meal or corn and full fat soy, or wheat meal or sunflower meal.

A feedstuff of the present invention may contain between about 5 to about 40% corn DDGS. For poultry—the feedstuff on average may contain between about 7 to 15% corn DDGS. For swine (pigs)—the feedstuff may contain on average 5 to 40% corn DDGS.

A feedstuff of the present invention may contain corn as a single grain, in which case the feedstuff may comprise between about 35% to about 80% corn.

In feedstuffs comprising mixed grains, e.g. comprising corn and wheat for example, the feedstuff may comprise at least 10% corn.

In addition or in the alternative, a feedstuff of the present invention may comprise at least one high fibre feed material and/or at least one by-product of the at least one high fibre feed material to provide a high fibre feedstuff. Examples of high fibre feed materials include: wheat, barley, rye, oats, by products from cereals, such as corn gluten meal, corn gluten feed, wet-cake, Distillers Dried Grain (DDG), Distillers Dried Grain Solubles (DDGS), wheat bran, wheat middlings, wheat shorts, rice bran, rice hulls, oat hulls, palm kernel, and citrus pulp. Some protein sources may also be regarded as high fibre: protein obtained from sources such as sunflower, lupin, fava beans and cotton.

In one embodiment the feedstuff of the present invention comprises at least one high fibre material and/or at least one by-product of the at least one high fibre feed material selected from the group consisting of Distillers Dried Grain Solubles (DDGS)—particularly cDDGS, wet-cake, Distillers Dried Grain (DDG)—particularly cDDG, wheat bran, and wheat for example.

In one embodiment the feedstuff of the present invention comprises at least one high fibre material and/or at least one by-product of the at least one high fibre feed material selected from the group consisting of Distillers Dried Grain Solubles (DDGS)—particularly cDDGS, wheat bran, and wheat for example.

In the present invention the feed may be one or more of the following: a compound feed and premix, including pellets, nuts or (cattle) cake; a crop or crop residue: corn, soybeans, sorghum, oats, barley copra, straw, chaff, sugar beet waste; fish meal; meat and bone meal; molasses; oil cake and press cake; oligosaccharides; conserved forage plants: silage; seaweed; seeds and grains, either whole or prepared by crushing, milling etc.; sprouted grains and legumes; yeast extract.

The term "feed" in the present invention encompasses in some embodiments pet food. A pet food is plant or animal material intended for consumption by pets, such as dog food or cat food. Pet food, such as dog and cat food, may be either in a dry form, such as kibble for dogs, or wet canned form. Cat food may contain the amino acid taurine.

The term "feed" in the present invention encompasses in some embodiments fish food. A fish food normally contains macro nutrients, trace elements and vitamins necessary to keep captive fish in good health. Fish food may be in the form of a flake, pellet or tablet. Pelleted forms, some of which sink rapidly, are often used for larger fish or bottom feeding species. Some fish foods also contain additives, such as beta carotene or sex hormones, to artificially enhance the colour of ornamental fish.

The term "feed" in the present invention encompasses in some embodiment bird food. Bird food includes food that is used both in birdfeeders and to feed pet birds. Typically bird food comprises of a variety of seeds, but may also encompass suet (beef or mutton fat).

As used herein the term "contacted" refers to the indirect or direct application of the enzyme (or composition comprising the enzyme) of the present invention to the product (e.g. the feed). Examples of the application methods which may be used, include, but are not limited to, treating the product in a material comprising the feed additive composition, direct application by mixing the feed additive composition with the product, spraying the feed additive composition onto the product surface or dipping the product into a preparation of the feed additive composition.

In one embodiment the feed additive composition of the present invention is preferably admixed with the product (e.g. feedstuff). Alternatively, the feed additive composition may be included in the emulsion or raw ingredients of a feedstuff.

For some applications, it is important that the composition is made available on or to the surface of a product to be affected/treated. This allows the composition to impart one or more of the following favourable characteristics: performance benefits.

The modified enzyme (or composition comprising the modified enzyme) of the present invention may be applied to intersperse, coat and/or impregnate a product (e.g. feedstuff or raw ingredients of a feedstuff) with a controlled amount of said enzyme.

In a particularly preferred embodiment the enzyme (or composition comprising the enzyme) of the present invention is homogenized to produce a powder.

In an alternative preferred embodiment, the enzyme (or composition comprising the enzyme) of the present invention is formulated to granules as described in WO2007/044968 (referred to as TPT granules) or WO1997/016076 or WO1992/012645 incorporated herein by reference.

In another preferred embodiment when the feed additive composition is formulated into granules the granules comprise a hydrated barrier salt coated over the protein core. The advantage of such salt coating is improved thermo-tolerance, improved storage stability and protection against other feed additives otherwise having adverse effect on the enzyme.

Preferably, the salt used for the salt coating has a water activity greater than 0.25 or constant humidity greater than 60% at 20° C.

Preferably, the salt coating comprises a $Na_2SO_4$.

The method of preparing an enzyme (or composition comprising the enzyme) of the present invention may also comprise the further step of pelleting the powder. The powder may be mixed with other components known in the art. The powder, or mixture comprising the powder, may be forced through a die and the resulting strands are cut into suitable pellets of variable length.

Optionally, the pelleting step may include a steam treatment, or conditioning stage, prior to formation of the pellets. The mixture comprising the powder may be placed in a conditioner, e.g. a mixer with steam injection. The mixture is heated in the conditioner up to a specified temperature, such as from 60-100° C., typical temperatures would be 70° C., 80° C., 85° C., 90° C. or 95° C. The residence time can be variable from seconds to minutes and even hours. Such as 5 seconds, 10 seconds, 15 seconds, 30 seconds, 1 minutes 2 minutes., 5 minutes, 10 minutes, 15 minutes, 30 minutes and 1 hour.

It will be understood that the enzyme (or composition comprising the enzyme) of the present invention is suitable for addition to any appropriate feed material.

It will be understood by the skilled person that different animals require different feedstuffs, and even the same animal may require different feedstuffs, depending upon the purpose for which the animal is reared.

Optionally, the feedstuff may also contain additional minerals such as, for example, calcium and/or additional vitamins.

Preferably, the feedstuff is a corn soybean meal mix.

In one embodiment, preferably the feed is not pet food.

In another aspect there is provided a method for producing a feedstuff. Feedstuff is typically produced in feed mills in which raw materials are first ground to a suitable particle size and then mixed with appropriate additives. The feedstuff may then be produced as a mash or pellets; the later typically involves a method by which the temperature is raised to a target level and then the feed is passed through a die to produce pellets of a particular size. The pellets are allowed to cool. Subsequently liquid additives such as fat and enzyme may be added. Production of feedstuff may also involve an additional step that includes extrusion or expansion prior to pelleting—in particular by suitable techniques that may include at least the use of steam.

The feedstuff may be a feedstuff for a monogastric animal, such as poultry (for example, broiler, layer, broiler breeders, turkey, duck, geese, water fowl), and swine (all age categories), a ruminant such as cattle (e.g. cows or bulls (including calves)), horses, sheep, a pet (for example dogs, cats) or fish (for example agastric fish, gastric fish, freshwater fish such as salmon, cod, trout and carp, e.g. koi carp, marine fish such as sea bass, and crustaceans such as shrimps, mussels and scallops). Preferably the feedstuff is for poultry.

Corn Based Feedstuff

In a preferred embodiment the feedstuff may be a corn based feedstuff. The term "corn based feedstuff" as used herein means a feedstuff which comprises or consists of corn (maize) or a by-product of corn.

Preferably the corn based feedstuff comprises corn or a by-product of corn as the major constituent. For example the corn based feedstuff may comprise at least 35% corn or a by-product of corn, such as at least 40% corn or a by-product of corn, such as at least 50% corn or a by-product of corn, such as at least 60% corn or a by-product of corn, such as at least 70% corn or a by-product of corn, such as at least 80% or a by-product of corn, such as at least 90% corn or a by-product of corn, for example 100% corn or a by-product of corn.

In some embodiments the corn based feedstuff may comprise corn or a by-product of corn as a minor constituent; in which case the feedstuff may be supplemented with corn or a by-product of corn. By way of example only the feedstuff may comprise for example wheat supplemented with corn or a by-product of corn.

When corn or the by-product of corn is a minor constituent of the feedstuff, the corn or by-product of corn is at least 5%, preferably at least 10%, preferably at least 20%, preferably at least 30% of the feedstuff.

For the avoidance of doubt the term "corn" as used herein is synonymous with maize, e.g. *Zea mays*.

In one embodiment the by-product of corn may be corn Distillers Dried Grain Solubles (cDDGS) or corn wet-cake or corn Distillers Dried Grain (DDG) or corn gluten meal or corn gluten feed or combinations thereof.

In one embodiment preferably the arabinoxylan-containing material of the present invention comprises a by-product of corn, such as corn Distillers Dried Grain Solubles (cDDGS) or corn wet-cake or corn Distillers Dried Grain (DDG) or corn gluten meal or corn gluten feed or combinations thereof.

Wheat Based Feedstuff

In a preferred embodiment the feedstuff may be a wheat based feedstuff. The term "wheat based feedstuff" as used herein means a feedstuff which comprises or consists of wheat or a by-product of wheat.

Preferably the wheat based feedstuff comprises wheat or a by-product of wheat as the major constituent. For example the wheat based feedstuff may comprise at least 40% wheat or a by-product of wheat, such as at least 60% wheat or a by-product of wheat, such as at least 80% or a by-product of wheat, such as at least 90% wheat or a by-product of wheat, for example 100% wheat or a by-product of wheat.

In some embodiments the wheat based feedstuff may comprise wheat or a by-product of wheat as a minor constituent; in which case the feedstuff may be supplemented with wheat or a by-product of wheat. By way of example only the feedstuff may comprise for example wheat supplemented with wheat or a by-product of wheat.

When wheat or the by-product of wheat is a minor constituent of the feedstuff, the wheat or by-product of wheat is at least 5%, preferably at least 10%, preferably at least 20%, preferably at least 30% of the feedstuff.

In one embodiment the by-product of wheat may be wheat bran, wheat middlings, wheat fibres for example.

Bran is the hard outer layer of grain and consists of combined aleurone and pericarp. Along with germ, it is an integral part of whole grains, and is often produced as a by-product of milling in the production of refined grains. When bran is removed from grains, the grains lose a portion of their nutritional value. Bran is present in and may be milled from any cereal grain, including rice, corn (maize), wheat, oats, barley and millet. Bran is particularly rich in dietary fibre and essential fatty acids and contains significant quantities of starch, protein, vitamins and dietary minerals.

Wheat middlings is coarse and fine particles of wheat bran and fine particles of wheat shorts, wheat germ, wheat flour and offal from the "tail of the mill".

Wheat middlings is an inexpensive by-product intermediate of human food and animal feed. In one embodiment preferably the arabinoxylan-containing material of the present invention comprises wheat bran and/or wheat middlings.

Wet-Cake, Distillers Dried Grains (DDG) and Distillers Dried Grain Solubles (DDGS)

Wet-cake, Distillers Dried Grains and Distillers Dried Grains with Solubles are products obtained after the removal of ethyl alcohol by distillation from yeast fermentation of a grain or a grain mixture by methods employed in the grain distilling industry.

Stillage coming from the distillation (e.g. comprising water, remainings of the grain, yeast cells etc.) is separated into a "solid" part and a liquid part.

The solid part is called "wet-cake" and can be used as animal feed as such. The liquid part is (partially) evaporated into a syrup (solubles).

When the wet-cake is dried it is Distillers Dried Grains (DDG).

When the wet-cake is dried together with the syrup (solubles) it is Distillers Dried Grains with Solubles (DDGS).

Wet-cake may be used in dairy operations and beef cattle feedlots.

The dried DDGS may be used in livestock, e.g. dairy, beef and swine) feeds and poultry feeds.

Corn DDGS is a very good protein source for dairy cows.

Corn Gluten Meal

In one aspect, the by-product of corn may be corn gluten meal (CGM).

CGM is a powdery by-product of the corn milling industry. CGM has utility in, for example, animal feed. It can be used as an inexpensive protein source for feed such as pet food, livestock feed and poultry feed. It is an especially good source of the amino acid cysteine, but must be balanced with other proteins for lysine.

Feed Additive Composition

The feed additive composition of the present invention and/or the feedstuff comprising same may be used in any suitable form.

The feed additive composition of the present invention may be used in the form of solid or liquid preparations or alternatives thereof. Examples of solid preparations include powders, pastes, boluses, capsules, pellets, tablets, dusts, and granules which may be wettable, spray-dried or freeze-dried. Examples of liquid preparations include, but are not limited to, aqueous, organic or aqueous-organic solutions, suspensions and emulsions.

In some applications, the feed additive compositions of the present invention may be mixed with feed or administered in the drinking water.

In one aspect the present invention relates to a method of preparing a feed additive composition, comprising admixing a xylanase as taught herein with a feed acceptable carrier, diluent or excipient, and (optionally) packaging.

Premix

The feedstuff and/or feed additive composition may be combined with at least one mineral and/or at least one vitamin. The compositions thus derived may be referred to herein as a premix.

Malting and Brewing

The enzyme having xylanase activity, e.g. the GH10 xylanase enzyme (such as the modified GH10 xylanase enzyme) or a fragment thereof, of the present invention (or composition comprising the enzyme) of the present invention may be used in malting and brewing.

Barley grains contain 1.7 to 4.1% (w/w) water-extractable and 3.6 to 6.4% (w/w) total beta-glucan (Anderson, M. A., Cook, J. A., & Stone, B. A., Journal of the Institute of Brewing, 1978, 84, 233-239; Henry, J., Journal of the Science of Food and Agriculture, 1985, 36, 1243).

Wheat grains contain 0.1 to 0.8% (w/w) water-extractable and 0.6 to 1.4% (w/w) total beta-glucan (Anderson, M. A. et al (1978) supra).

Efficient hydrolysis of arabinoxylans (AXsol) and beta-glucan is important because such compounds can be involved in production problems such as wort viscosity (Ducroo, P. & Frelon, P. G., Proceedings of the European Brewery Convention Congress, Zurich, 1989, 445; Viëtor, R. J. & Voragen, A. G. J., Journal of the Institute of Brewing, 1993, 99, 243) and filterability and haze formation (Coote, N. & Kirsop, B. H. 1976., Journal of the Institute of Brewing, 1976, 82, 34; Izawa, M., Kano, Y. & Kanimura, M. 1991. Proceedings Aviemore Conference on Malting, brewing and Distilling, 1990, 427).

The present invention provides a method of hydrolysing arabinoxylans (e.g. AXinsol and AXsol) during malting and brewing wherein wheat grains, barley grains or a combination thereof, or portions of the wheat and/or barley grains, are admixed with the modified xylanase of the present invention.

In one aspect of the present invention may relate to a food composition that is a beverage, including, but not limited to, a fermented beverage such as beer and wine, comprising an enzyme having xylanase activity, e.g. the GH10 xylanase enzyme (such as the modified GH10 xylanase enzyme) or a fragment thereof, of the present invention.

In another aspect of the present invention may relate to a food composition that is a beverage, including, but not limited to, a fermented beverage such as beer and wine, comprising a modified xylanase according to the present invention.

In the context of the present invention, the term "fermented beverage" is meant to comprise any beverage produced by a method comprising a fermentation process, such as a microbial fermentation, such as a bacterial and/or yeast fermentation.

In an aspect of the invention the fermented beverage is beer. The term "beer" is meant to comprise any fermented wort produced by fermentation/brewing of a starch-containing plant material. Often, beer is produced from malt or adjunct, or any combination of malt and adjunct as the starch-containing plant material. As used herein the term "malt" is understood as any malted cereal grain, such as malted barley or wheat.

As used herein the term "adjunct" refers to any starch and/or sugar containing plant material which is not malt, such as barley or wheat malt. As examples of adjuncts, mention can be made of materials such as common corn grits, refined corn grits, brewer's milled yeast, rice, sorghum, refined corn starch, barley, barley starch, dehusked barley, wheat, wheat starch, torrified cereal, cereal flakes, rye, oats, corn (maize), potato, tapioca, cassava and syrups, such as corn syrup, sugar cane syrup, inverted sugar syrup, barley and/or wheat syrups, and the like may be used as a source of starch.

As used herein, the term "mash" refers to an aqueous slurry of any starch and/or sugar containing plant material such as grist, e. g. comprising crushed barley malt, crushed barley, and/or other adjunct or a combination hereof, mixed with water later to be separated into wort and spent grains.

As used herein, the term "wort" refers to the unfermented liquor run-off following extracting the grist during mashing.

In another aspect the invention relates to a method of preparing a fermented beverage such as beer comprising mixing the modified xylanase of the present invention with malt or adjunct.

Examples of beers comprise: full malted beer, beer brewed under the "Reinheitsgebot", ale, IPA, lager, bitter, Happoshu (second beer), third beer, dry beer, near beer, light beer, low alcohol beer, low calorie beer, porter, bock beer, stout, malt liquor, non-alcoholic beer, non-alcoholic malt liquor and the like, but also alternative cereal and malt beverages such as fruit flavored malt beverages, e. g. citrus flavored, such as lemon-, orange-, lime-, or berry-flavored malt beverages, liquor flavored malt beverages, e. g., vodka-, rum-, or tequila-flavored malt liquor, or coffee flavored malt beverages, such as caffeine-flavored malt liquor, and the like.

Breakdown of Grain-Based Material E.G. for Biofuel Production

The enzyme having xylanase activity, e.g. the GH10 xylanase enzyme (such as the modified GH10 xylanase enzyme) or a fragment thereof, of the present invention (or composition comprising the enzyme) may be used to breakdown (degrade) AXinsol and AXsol during grain processing from e.g. grain-based material. The grain-based material may be whole grains (e.g. whole wheat, barley, rye, triticale or corn grains or mixtures thereof) or portions of the whole grains, or mixtures thereof.

In one embodiment the enzyme having xylanase activity, e.g. the GH10 xylanase enzyme (such as the modified GH10 xylanase enzyme) or a fragment thereof, of the present invention (or composition comprising the enzyme) may be used to breakdown (degrade) AXinsol and AXsol in grain-based materials or whole grains.

For the avoidance of doubt the whole grains can be mechanically broken.

The grain-based material may be broken down or degraded to glucose. The glucose may subsequently be used as a feedstock for any fermentation process, e.g. for biofuel (e.g. bioethanol) production and/or biochemicals (e.g., bio-based isoprene) production.

The grain-based material may be feedstock for a biofuel (e.g. bioethanol) production process.

Today most fuel ethanol is produced from corn (maize) grain, which is milled or grinded, treated with amylase enzymes to hydrolyse starch to sugars, fermented, and distilled. While substantial progress has been made in reducing costs of ethanol production, substantial challenges remain. Improved techniques are still needed to reduce the cost of biofuel feedstocks for ethanol production. For example, in grain-based ethanol production degradation of arabinoxylans may increase accessibility of starch.

The present invention provides a modified xylanase for use in the breakdown of hemicelluloses, e.g. arabinoxylan—particularly AXinsol and AXsol.

By way of example only, in the European fuel alcohol industry, small grains like wheat, barley and rye are common raw materials, in the US corn is mainly used. Wheat, barley and rye contain, next to starch, high levels of non-starch polysaccharide polymers (NSP), like cellulose, beta-glucan and hemicellulose.

The ratio in which the different NSPs are represented differ for each feedstock. The table below shows the different amounts of NSPs in wheat, barley and rye compared to some other feedstocks.

TABLE 1

Non-starch Polysaccharides present in different feedstocks (g kg$^{-1}$ dry matter)

| | Corn | Wheat | Rye | Barley Hulled | Barley Hulless | Oats Hulled | Oats Hulless |
|---|---|---|---|---|---|---|---|
| Beta-Glucan | 1 | 8 | 16 | 42 | 42 | 28 | 41 |
| Cellulose | 22 | 17-20 | 15-16 | 43 | 10 | 82 | 14 |
| Soluble and Non-soluble NCP[1] | 75 | 89-99 | 116-136 | 144 | 114 | 150 | 113 |
| Total NSP | 97 | 107-119 | 132-152 | 186 | 124 | 232 | 116 |

[1]Non Cellulosic Polysaccharides: pentosans, (arabino)xylans and other hemicelluloses NSPs can give high viscosity to grain mashes. High viscosity has a negative impact on ethanol production since it will limit the solid concentration that can be used in mashing and it will reduce the energy efficiency of the process. In addition, residual hemicelluloses present throughout the process may contribute to fouling in heat exchangers and distillation equipment. The largest impact of a high viscosity is seen when a mash is cooled to fermentation temperature (32° C.). This explains that the viscosity needs to be reduced in the process anywhere before the cooling step.

In one embodiment of the present invention the method for degrading grain-based material comprises admixing the modified xylanase as disclosed herein as early as possible in the biofuel (e.g. bioethanol) production process, e.g. preferably during mixing of the grain-based material at the start of the process. One advantage of adding the modified xylanases as disclosed herein at an early stage in the process is that the enzymes breakdown initial viscosity.

In one embodiment of the present invention the method for degrading grain-based material comprises admixing the modified xylanase as disclosed herein prior to or during liquefaction, saccharification, fermentation, simultaneous saccharification and fermentation, post fermentation or a combination thereof.

Therefore in one embodiment the present invention relates to reducing viscosity when degrading grain-based materials, e.g. in biofuel (e.g. bioethanol) production processes.

The benefits of using the enzyme having xylanase activity, e.g. the OHIO xylanase enzyme (such as the modified GH10 xylanase enzyme) or a fragment thereof, of the present invention and taught herein to reduce viscosity when degrading grain-based materials, e.g. in biofuel (e.g. bioethanol) production processes are multiple:

Higher dry substance mash can be used in the process
Higher solids content of final syrup can be obtained
Better heat transfer, lower energy requirement
Reduced evaporator fouling leading to reduced cleaning costs
Increased final ethanol yields
Improved quality of DDGS (by-product)
Better separation between the solid and liquid part during stillage separation (after distillation). The lower viscosity increases separation efficiency.

A further significant advantage of the present invention is that use of the enzyme having xylanase activity, e.g. the GH10 xylanase enzyme (such as the modified GH10 xylanase enzyme) or a fragment thereof, of the present invention in biofuel production can also result in improved (by)products from that process such as wet-cake, Distillers Dried Grains (DDG) or Distillers Dried Grains with Solubles (DDGS). Therefore one advantage of the present invention is since the wet-cake, DDG and DDGS are (by) products of biofuel (e.g. bioethanol) production the use of the present invention can result is improved quality of these (by)products. For example the arabinoxylans in the (by) products can be already dissolved during the biofuel production process.

Cereal (e.g. Wheat) Gluten-Starch Separation

The enzyme having xylanase activity, e.g. the GH10 xylanase enzyme (such as the modified GH10 xylanase enzyme) or a fragment thereof, of the present invention (or composition comprising the enzyme) of the present invention or as disclosed herein may be used to breakdown (degrade) AXinsol and AXsol during wheat starch and gluten separation.

After initial separation of the wheat bran and germ from the endosperm, fractionation of wheat endosperm flour into starch and gluten fractions is industrially applied on large scale to obtain high quality A-starch and byproducts B-starch and vital gluten.

The product of the degradation of the cereal flour (e.g. wheat flour) in the present invention is starch (high quality A-starch).

In addition, by-products B-starch and vital gluten are also produced. Each individual product is then further processed to supplement or modify food product characteristics to the market needs.

There are several wheat separation processes used by industry described in literature. These industrial processes differ mainly in the forms of the flour-water mixtures presented to the fractionation equipment (centrifuge, hydrocyclone, or screen) or in the initial reaction conditions as temperature and applying of shear (Abdulvahit Sayaslan, Lebensm.-Wiss. U.—*Technol* 37 (2004) 499-515, *Wetmilling of wheat flour: industrial processes and small-sacale test methods*).

In the method for separating a cereal flour (e.g. wheat flour) into starch and gluten fractions the method comprises admixing a cereal flour (e.g. wheat flour), water and a modified xylanase. The cereal flour, water and modified xylanase may be mixed simultaneously or sequentially. In some embodiments the cereal flour (e.g. wheat flour) and water may be admixed before admixing with the modified xylanase.

In general, cereal flour (e.g. wheat flour) is either mixed to a dough or batter, varying between 35 to 63% Dry solids, at temperatures of ~20-45° C. The mixture is then further processed either by:

1) letting the mixture rest for some time (~30 minutes) and sequentially washing out the starch from the mixture using a screen, centrifuge or hydrocyclone to separate the starch milk from the gluten, or
2) applying shear to the mixture, optionally diluting the mixture further and then separating the wheat flour by a hydrocyclone, or a 2- or 3-phase decanter centrifuge.

The term "dry solids" as used herein means total solids (dissolved and undissolved) of a slurry (in %) on a dry weight basis.

In one embodiment of the present invention the method or use as claimed may include the steps of mixing wheat flour to form a dough or batter between 35-63% dry solids, at a temperature of about 20 to about 45° C. and separating the starch from the gluten.

The method of the present invention may further comprise:

a) resting the mixture for about 30 minutes and sequentially washing out the starch from the mixture using either a screen, a centrifuge or a hydrocyclone to separate the starch milk from the gluten; or
b) applying shear to the mixture and optionally diluting the mixture further, separating the starch from the gluten using a hydrocyclone or a 2- or 3-phase decanter centrifuge.

The present invention provides for improving the separation of the starch and the gluten by adding a enzyme having xylanase activity, e.g. the GH10 xylanase enzyme (such as the modified GH10 xylanase enzyme) or a fragment thereof, of the present invention suitably during the initial mixing step of flour and water in the various processes described above used for wheat starch separation. Separation is improved by adding a modified xylanase during the initial mixing step due to viscosity reduction and the hydrolysis of AXsol and/or AXinsol interfering with the gluten particles. By degrading these poly- and oligosaccharides, gluten agglomeration is enhanced, improving the gluten yield. (S. A. Frederix, C. M. Courtin, Delcour, *J. Cereal Sci.* 40 (2004) 41-49, Substrate selectivity and inhibitor sensitivity affect xylanase functionality in wheat flour gluten-starch separation).

One advantage of the present invention is that it results in higher A-starch yields and/or better quality gluten (e.g. better quality vital gluten).

One advantage of the present invention is that it improves wheat gluten-starch separation.

One of the ways to evaluate gluten quality is by monitoring gluten agglomeration. When a certain amount of friction through kneading of the dough or mixing of the batter is applied, gluten particles tend to agglomerate into larger particles that form a polymeric network, called "vital gluten". "Vital gluten" can be added to food products to improve properties of baked goods such as dough strength, shelf-life and bread volume (L. Day, M. A. Augustin, I. L. Batey and C. W. Wrigley; *Wheat-gluten uses and industry needs; Trends in Food Science & Technology* 17 (2006) 82-90).

In the bakery industry, the quality and quantity of the gluten in a wheat flour is determined by the ICC standard assay No. 155 (AACC 38-12) using a Glutomatic. In this device, a dough is formed from wheat flour (10.0 gr) mixed with a small amount of 2% NaCl solution (4.2-4.8 ml). After 20 seconds of mixing step, the dough is continuously kneaded while being washed for 5 minutes with a 2% NaCl solution at room temperature (~22° C.) pumped through the mixing cup at a flow rate of ~70 ml/minute. During this washing step, the wash water containing starch is collected and the gluten particles form a gluten ball within the Glutomatic sieve holder.

The quality of the gluten is measured by evaluating the gluten agglomeration. This is done by centrifuging the gluten ball in a special centrifuge containing a small sieve. The gluten particles that pass this sieve are weighed (small gluten) and the total amount of gluten is weighed. The gluten index is calculated by (total wet gluten−small wet gluten)/total wet gluten. The more gluten agglomeration is improved, the smaller the small gluten fraction will be and the higher the gluten index value is. A high gluten index, with a theoretical maximum of 100%, indicates a high quality gluten ball.

Another value to quantify the amount of gluten is the dried gluten yield (%). This value is calculated by dividing the grams of total dried gluten by the total amount of dry flour which was used in the experiment. The more dried gluten is recovered, the better the separation is. This industrial assay is currently under adaptation to simulate a dough separation process used in industry.

Dosages

Preferably, the enzyme having xylanase activity, e.g. the GH10 xylanase enzyme (such as the modified GH10 xylanase enzyme) or a fragment thereof, of the present invention is present in the xylan-containing material (e.g. feedstuff) in the range of about 500 XU/kg to about 16,000 XU/kg xylan-containing material (e.g. feed), more preferably about 750 XU/kg feed to about 8000 XU/kg xylan-containing material (e.g. feed), preferably about 1500 XU/kg feed to about 3000 XU/kg xylan-containing material (e.g. feed), preferably about 2000 XU/kg feed to about 2500 XU/kg xylan-containing material (e.g. feed), and even more preferably about 1000 XU/kg xylan-containing material (e.g. feed) to about 4000 XU/kg xylan-containing material (e.g. feed).

In one embodiment the enzyme having xylanase activity, e.g. the GH10 xylanase enzyme (such as the modified GH10 xylanase enzyme) or a fragment thereof, of the present invention is present in the xylan-containing material (e.g. feedstuff) at more than about 500 XU/kg xylan-containing material (e.g. feed), suitably more than about 600 XU/kg xylan-containing material (e.g. feed), suitably more than about 700 XU/kg xylan-containing material (e.g. feed), suitably more than about 800 XU/kg xylan-containing material (e.g. feed), suitably more than about 900 XU/kg xylan-containing material (e.g. feed), suitably more than about 1000 XU/kg xylan-containing material (e.g. feed), suitably more than about 2000 XU/kg, suitably more than about 2500 XU/kg, suitably more than about 3000 XU/kg xylan-containing material (e.g. feed), In one embodiment the enzyme having xylanase activity, e.g. the GH10 xylanase enzyme (such as the modified GH10 xylanase enzyme) or a fragment thereof, of the present invention is present in the xylan-containing material (e.g. feedstuff) at a concentration of between about 2000 XU/kg to about 2500 XU/kg.

In one embodiment the enzyme having xylanase activity, e.g. the GH10 xylanase enzyme (such as the modified GH10 xylanase enzyme) or a fragment thereof, of the present invention is present in the xylan-containing material (e.g. feedstuff) at less than about 16,000 XU/kg xylan-containing material (e.g. feed), suitably less than about 8000 XU/kg xylan-containing material (e.g. feed), suitably less than about 7000 XU/kg xylan-containing material (e.g. feed), suitably less than about 6000 XU/kg xylan-containing material (e.g. feed), suitably less than about 5000 XU/kg xylan-containing material (e.g. feed), suitably less than about 4000 XU/kg xylan-containing material (e.g. feed).

Preferably, the enzyme having xylanase activity, e.g. the GH10 xylanase enzyme (such as the modified GH10 xylanase enzyme) or a fragment thereof, of the present invention may be present in a feed additive composition in range of about 100 XU/g to about 320,000 XU/g composition, more preferably about 300 XU/g composition to about 160,000 XU/g composition, and even more preferably about 500 XU/g composition to about 50,000 XU/g composition, and even more preferably about 500 XU/g composition to about 40,000 XU/g composition.

In one embodiment the enzyme having xylanase activity, e.g. the GH10 xylanase enzyme (such as the modified GH10 xylanase enzyme) or a fragment thereof, of the present invention is present in the feed additive composition at more than about 100 XU/g composition, suitably more than about 200 XU/g composition, suitably more than about 300 XU/g composition, suitably more than about 400 XU/g composition, suitably more than about 500 XU/g composition.

In one embodiment the enzyme having xylanase activity, e.g. the GH10 xylanase enzyme (such as the modified GH10 xylanase enzyme) or a fragment thereof, of the present invention is present in the feed additive composition at less than about 320,000 XU/g composition, suitably less than about 160,000 XU/g composition, suitably less than about 50,000 XU/g composition, suitably less than about 40,000 XU/g composition, suitably less than about 30000 XU/g composition.

The xylanase activity can be expressed in xylanase units (XU) measured at pH 5.0 with AZCL-arabinoxylan (azurine-crosslinked wheat arabinoxylan, e.g. Xylazyme tablets, Megazyme) as substrate. Hydrolysis by endo-(1-4)-ß-D-xylanase (xylanase) produces water soluble dyed fragments, and the rate of release of these (increase in absorbance at 590 nm) can be related directly to enzyme activity. The xylanase units (XU) are determined relatively to an enzyme standard (Danisco Xylanase, available from Danisco Animal Nutrition) at standard reaction conditions, which are 40° C., 5 min reaction time in McIlvaine buffer, pH 5.0.

The xylanase activity of the standard enzyme is determined as amount of released reducing sugar end groups from an oat-spelt-xylan substrate per min at pH 5.3 and 50° C. The reducing sugar end groups react with 3, 5-Dinitrosalicylic acid and formation of the reaction product can be measured as increase in absorbance at 540 nm. The enzyme activity is quantified relative to a xylose standard curve (reducing sugar equivalents). One xylanase unit (XU) is the amount of standard enzyme that releases 0.5 µmol of reducing sugar equivalents per min at pH 5.3 and 50° C.

In one embodiment suitably the enzyme is classified using the E.C. classification above, and the E.C. classification designates an enzyme having that activity when tested in the assay taught herein for determining 1 XU.

Preferably, the enzyme having xylanase activity, e.g. the GH10 xylanase enzyme (such as the modified GH10 xylanase enzyme) or a fragment thereof, of the present invention is present in the mixing step of a wheat starch separation process in the dough or batter in the range of about 0.01 kg/MT DS dough or batter to about 0.60 kg/MT DS, more preferably about 0.05 kg/MT DS to about 0.45 kg/MT DS dough or batter, and even more preferably about 0.10 kg/MT DS to about 0.25 kg/MT DS dough or batter.

In some embodiments (particularly in the wheat starch separation embodiment) the enzyme having xylanase activity, e.g. the GH10 xylanase enzyme (such as the modified GH10 xylanase enzyme) or a fragment thereof, of the present invention may be dosed in the range of about 0.019 g protein/MT DS wheat flour (which is equivalent to 0.019 mg/kg DS) to about 119 g protein/MT DS wheat flour (which is equivalent to 119 mg/kg DS—where DS means dry solids content and MT means metric ton.

In some embodiments (particularly in the wheat starch separation embodiment) the enzyme having xylanase activity, e.g. the GH10 xylanase enzyme (such as the modified GH10 xylanase enzyme) or a fragment thereof, of the present invention may be dosed at about 1.19 g protein/MT DS wheat flour (which is equivalent to about 1.19 mg/kg DS)—where DS means dry solids content and MT means metric ton.

In some embodiments (particularly in the wheat starch separation embodiment) the enzyme having xylanase activity, e.g. the GH10 xylanase enzyme (such as the modified GH10 xylanase enzyme) or a fragment thereof, of the present invention may be dosed in the range of about 9 to about 120000 units/kg wheat flour, suitably between about 500-2400 units/kg wheat flour, suitably between about 900-1200 units/kg wheat flour (wherein 1 unit is defined as the amount of enzyme required to generate 1 micromole of xylose reducing sugar equivalents per minute under the conditions of the birch wood assay of Example 4).

In some embodiments (particularly in degrading grain-based material) the enzyme having xylanase activity, e.g. the GH10 xylanase enzyme (such as the modified GH10 xylanase enzyme) or a fragment thereof, of the present invention may be dosed in the range of about 0.29 g/protein/MT DS wheat (which is equivalent to 0.29 mg/kg DS) to about 0290 g/protein/MT DS wheat (which is equivalent to 290 mg/kg DS).

In some embodiments (particularly in degrading grain-based material) the xylanase may be dosed at 2.9 g/protein/MT DS wheat (which is equivalent to 2.9 mg/kg DS).

In some embodiments (particularly in degrading grain-based material) the xylanase may be dosed in the range of about 22 to about 285000 units/kg, suitably about 1100 to about 5700 units/kg, suitably about 2200 to about 2850 units/kg (wherein 1 unit is defined as the amount of enzyme required to generate 1 micromole of xylose reducing sugar equivalents per minute under the conditions of the birch wood assay of Example 4).

The enzyme having xylanase activity, e.g. the GH10 xylanase enzyme (such as the modified OHIO xylanase enzyme) or a fragment thereof, of the present invention and/or composition comprising the enzyme according to the present invention may be designed for one-time dosing or may be designed for use (e.g. feeding) on a daily basis.

The optimum amount of the enzyme having xylanase activity, e.g. the GH10 xylanase enzyme (such as the modified GH10 xylanase enzyme) or a fragment thereof, of the present invention and/or composition comprising the enzyme to be used in the present invention will depend on the product to be treated and/or the method of contacting the product with the composition and/or the intended use for the same.

The amount of enzyme having xylanase activity, e.g. the GH10 xylanase enzyme (such as the modified GH10 xylanase enzyme) or a fragment thereof, of the present invention used in the compositions should be a sufficient amount to be effective.

The amount of enzyme having xylanase activity, e.g. the GH10 xylanase enzyme (such as the modified GH10 xylanase enzyme) or a fragment thereof, of the present invention used in the compositions should be a sufficient amount to be effective and to remain sufficiently effective in for example improving the performance of an animal fed feed products containing said composition. This length of time for effectiveness should extend up to at least the time of utilisation of the product (e.g. feed additive composition or feed containing same).

Formulation

In one embodiment the enzyme having xylanase activity, e.g. the GH10 xylanase enzyme (such as the modified GH10 xylanase enzyme) or a fragment thereof, of the present invention may be formulated as a liquid, a dry powder or a granule.

The dry powder or granules may be prepared by means known to those skilled in the art, such as, in top-spray fluid bed coater, in a bottom spray Wurster or by drum granulation (e.g. High sheer granulation), extrusion, pan coating or in a microingredients mixer.

For some embodiments the enzyme having xylanase activity, e.g. the GH10 xylanase enzyme (such as the modified GH10 xylanase enzyme) or a fragment thereof, of the present invention may be coated, for example encapsulated.

In one embodiment the coating protects the modified enzyme from heat and may be considered a thermoprotectant.

In one embodiment the feed additive composition is formulated to a dry powder or granules as described in WO2007/044968 (referred to as TPT granules) or WO1997/016076 or WO1992/012645 (each of which is incorporated herein by reference).

In one embodiment the feed additive composition may be formulated to a granule for feed compositions comprising: a core; an active agent; and at least one coating, the active agent of the granule retaining at least 50% activity, at least 60% activity, at least 70% activity, at least 80% activity after conditions selected from one or more of a) a feed pelleting process, b) a steam-heated feed pretreatment process, c) storage, d) storage as an ingredient in an unpelleted mixture, and e) storage as an ingredient in a feed base mix or a feed premix comprising at least one compound selected from trace minerals, organic acids, reducing sugars, vitamins, choline chloride, and compounds which result in an acidic or a basic feed base mix or feed premix.

With regard to the granule at least one coating may comprise a moisture hydrating material that constitutes at least 55% w/w of the granule; and/or at least one coating may comprise two coatings. The two coatings may be a moisture hydrating coating and a moisture barrier coating. In some embodiments, the moisture hydrating coating may be between 25% and 60% w/w of the granule and the moisture barrier coating may be between 2% and 15% w/w of the granule. The moisture hydrating coating may be selected from inorganic salts, sucrose, starch, and maltodextrin and the moisture barrier coating may be selected from polymers, gums, whey and starch.

The granule may be produced using a feed pelleting process and the feed pretreatment process may be conducted between 70° C. and 95° C. for up to several minutes, such as between 85° C. and 95° C.

In one embodiment the feed additive composition may be formulated to a granule for animal feed comprising: a core; an active agent, the active agent of the granule retaining at least 80% activity after storage and after a steam-heated pelleting process where the granule is an ingredient; a moisture barrier coating; and a moisture hydrating coating that is at least 25% w/w of the granule, the granule having a water activity of less than 0.5 prior to the steam-heated pelleting process.

The granule may have a moisture barrier coating selected from polymers and gums and the moisture hydrating material may be an inorganic salt. The moisture hydrating coating may be between 25% and 45% w/w of the granule and the moisture barrier coating may be between 2% and 10% w/w of the granule.

The granule may be produced using a steam-heated pelleting process which may be conducted between 85° C. and 95° C. for up to several minutes.

In some embodiments the enzyme may be diluted using a diluent, such as starch powder, lime stone or the like.

In one embodiment, the enzyme having xylanase activity, e.g. the GH10 xylanase enzyme (such as the modified GH10 xylanase enzyme) or a fragment thereof, of the present invention or composition comprising the enzyme is in a liquid formulation suitable for consumption preferably such liquid consumption contains one or more of the following: a buffer, salt, sorbitol and/or glycerol.

In another embodiment the enzyme having xylanase activity, e.g. the GH10 xylanase enzyme (such as the modified GH10 xylanase enzyme) or a fragment thereof, of the present invention or composition comprising the enzyme may be formulated by applying, e.g. spraying, the enzyme(s) onto a carrier substrate, such as ground wheat for example.

In one embodiment the enzyme having xylanase activity, e.g. the GH10 xylanase enzyme (such as the modified GH10 xylanase enzyme) or a fragment thereof, of the present invention or composition comprising the enzyme according to the present invention may be formulated as a premix. By way of example only the premix may comprise one or more feed components, such as one or more minerals and/or one or more vitamins.

In one embodiment the enzyme having xylanase activity, e.g. the GH10 xylanase enzyme (such as the modified GH10 xylanase enzyme) or a fragment thereof, for use in the present invention are formulated with at least one physiologically acceptable carrier selected from at least one of maltodextrin, limestone (calcium carbonate), cyclodextrin, wheat or a wheat component, sucrose, starch, $Na_2SO_4$, Talc, PVA, sorbitol, benzoate, sorbiate, glycerol, sucrose, propylene glycol, 1,3-propane diol, glucose, parabens, sodium chloride, citrate, acetate, phosphate, calcium, metabisulfite, formate and mixtures thereof.

Packaging

In one embodiment the enzyme having xylanase activity, e.g. the GH10 xylanase enzyme (such as the modified GH10 xylanase enzyme) or a fragment thereof, of the present invention and/or composition comprising same (e.g. feed additive composition) and/or premix and/or feed or feedstuff according to the present invention is packaged.

In one preferred embodiment the feed additive composition and/or premix and/or feed or feedstuff is packaged in a bag, such as a paper bag.

In an alternative embodiment the feed additive composition and/or premix and/or feed or feedstuff may be sealed in a container. Any suitable container may be used.

Forms

The enzyme having xylanase activity, e.g. the GH10 xylanase enzyme (such as the modified GH10 xylanase enzyme) or a fragment thereof, of the present invention or composition comprising the enzyme (e.g. the feed additive composition) of the present invention and other components and/or the feedstuff comprising same may be used in any suitable form.

The enzyme having xylanase activity, e.g. the GH10 xylanase enzyme (such as the modified GH10 xylanase enzyme) or a fragment thereof, of the present invention or composition comprising same (e.g. feed additive composition) of the present invention may be used in the form of solid or liquid preparations or alternatives thereof. Examples of solid preparations include powders, pastes, boluses, capsules, pellets, tablets, pills, capsules, ovules, solutions or suspensions, dusts, and granules which may be wettable, spray-dried or freeze-dried. Examples of liquid preparations include, but are not limited to, aqueous, organic or aqueous-organic solutions, suspensions and emulsions.

The composition comprising the enzyme having xylanase activity, e.g. the GH10 xylanase enzyme (such as the modified GH10 xylanase enzyme) or a fragment thereof, of the present invention may contain flavouring or colouring agents, for immediate-, delayed-, modified-, sustained-, pulsed- or controlled-release applications.

By way of example, if the composition of the present invention is used in a solid, e.g. pelleted form, it may also contain one or more of: excipients such as microcrystalline cellulose, lactose, sodium citrate, calcium carbonate, dibasic calcium phosphate and glycine; disintegrants such as starch (preferably corn, potato or tapioca starch), sodium starch glycollate, croscarmellose sodium and certain complex silicates; granulation binders such as polyvinylpyrrolidone, hydroxypropylmethylcellulose (HPMC), hydroxypropylcellulose (HPC), sucrose, gelatin and acacia; lubricating agents such as magnesium stearate, stearic acid, glyceryl behenate and talc may be included.

Examples of nutritionally acceptable carriers for use in preparing the forms include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

Preferred excipients for the forms include lactose, starch, a cellulose, milk sugar or high molecular weight polyethylene glycols.

For aqueous suspensions and/or elixirs, the composition of the present invention may be combined with various sweetening or flavouring agents, colouring matter or dyes, with emulsifying and/or suspending agents and with diluents such as water, propylene glycol and glycerin, and combinations thereof.

Subject

The term "subject", as used herein, means an animal that is to be or has been administered with a modified xylanase according to the present invention or a feed additive composition according to the present invention or a feedstuff comprising said feed additive composition according to the present invention.

The term "subject", as used herein, means an animal.

In one embodiment, the subject is a mammal, bird, fish or crustacean including for example livestock or a domesticated animal (e.g. a pet).

In one embodiment the "subject" is livestock.

The term "livestock", as used herein refers to any farmed animal. Preferably, livestock is one or more of ruminants such as cattle (e.g. cows or bulls (including calves)), monogastric animals such as poultry (including broilers, chickens and turkeys), pigs (including piglets), birds, aquatic animals such as fish, agastric fish, gastric fish, freshwater fish such as salmon, cod, trout and carp, e.g. koi carp, marine fish such as sea bass, and crustaceans such as shrimps, mussels and scallops), horses (including race horses), sheep (including lambs).

In another embodiment the "subject" is a domesticated animal or pet or an animal maintained in a zoological environment.

The term "domesticated animal or pet or animal maintained in a zoological environment" as used herein refers to any relevant animal including canines (e.g. dogs), felines (e.g. cats), rodents (e.g. guinea pigs, rats, mice), birds, fish (including freshwater fish and marine fish), and horses.

Performance

As used herein, "animal performance" may be determined by the feed efficiency and/or weight gain of the animal and/or by the feed conversion ratio and/or by the digestibility of a nutrient in a feed (e.g. amino acid digestibility) and/or digestible energy or metabolizable energy in a feed and/or by nitrogen retention and/or by animals ability to avoid the negative effects of necrotic enteritis and/or by the immune response of the subject.

Preferably "animal performance" is determined by feed efficiency and/or weight gain of the animal and/or by the feed conversion ratio.

By "improved animal performance" it is meant that there is increased feed efficiency, and/or increased weight gain and/or reduced feed conversion ratio and/or improved digestibility of nutrients or energy in a feed and/or by improved nitrogen retention and/or by an improved immune response in the subject resulting from the use of feed additive composition of the present invention in feed in comparison to feed which does not comprise said feed additive composition.

Preferably, by "improved animal performance" it is meant that there is increased feed efficiency and/or increased weight gain and/or reduced feed conversion ratio.

As used herein, the term "feed efficiency" refers to the amount of weight gain per unit of feed when the animal is fed ad-libitum or a specified amount of feed during a period of time.

By "increased feed efficiency" it is meant that the use of a feed additive composition according the present invention in feed results in an increased weight gain per unit of feed intake compared with an animal fed without said feed additive composition being present.

Feed Conversion Ratio (FCR)

As used herein, the term "feed conversion ratio" refers to the amount of feed fed to an animal to increase the weight of the animal by a specified amount.

An improved feed conversion ratio means a lower feed conversion ratio.

By "lower feed conversion ratio" or "improved feed conversion ratio" it is meant that the use of a feed additive composition in feed results in a lower amount of feed being required to be fed to an animal to increase the weight of the animal by a specified amount compared to the amount of feed required to increase the weight of the animal by the same amount when the feed does not comprise said feed additive composition.

Nutrient Digestibility

Nutrient digestibility as used herein means the fraction of a nutrient that disappears from the gastro-intestinal tract or a specified segment of the gastro-intestinal tract, e.g. the small intestine. Nutrient digestibility may be measured as the difference between what is administered to the subject and what comes out in the faeces of the subject, or between what is administered to the subject and what remains in the digesta on a specified segment of the gastro intestinal tract, e.g. the ileum.

Nutrient digestibility as used herein may be measured by the difference between the intake of a nutrient and the excreted nutrient by means of the total collection of excreta during a period of time; or with the use of an inert marker that is not absorbed by the animal, and allows the researcher calculating the amount of nutrient that disappeared in the entire gastro-intestinal tract or a segment of the gastro-intestinal tract. Such an inert marker may be titanium dioxide, chromic oxide or acid insoluble ash. Digestibility may be expressed as a percentage of the nutrient in the feed, or as mass units of digestible nutrient per mass units of nutrient in the feed.

Nutrient digestibility as used herein encompasses starch digestibility, fat digestibility, protein digestibility, and amino acid digestibility.

Energy digestibility as used herein means the gross energy of the feed consumed minus the gross energy of the faeces or the gross energy of the feed consumed minus the gross energy of the remaining digesta on a specified segment of the gastro-intestinal tract of the animal, e.g. the ileum. Metabolizable energy as used herein refers to apparent metabolizable energy and means the gross energy of the feed consumed minus the gross energy contained in the faeces, urine, and gaseous products of digestion. Energy digestibility and metabolizable energy may be measured as the difference between the intake of gross energy and the gross energy excreted in the faeces or the digesta present in specified segment of the gastro-intestinal tract using the same methods to measure the digestibility of nutrients, with appropriate corrections for nitrogen excretion to calculate metabolizable energy of feed.

Combination with Other Components

The enzyme having xylanase activity, e.g. the GH10 xylanase enzyme (such as the modified GH10 xylanase enzyme) or a fragment thereof, of the present invention may be used in combination with other components.

In one embodiment the enzyme having xylanase activity, e.g. the GH10 xylanase enzyme (such as the modified GH10 xylanase enzyme) or a fragment thereof, of the present invention may be used in combination with a probiotic or a direct fed microbial (DFM), e.g. a direct fed bacteria.

The combination of the present invention comprises the enzyme having xylanase activity, e.g. the GH10 xylanase enzyme (such as the modified GH10 xylanase enzyme) or a fragment thereof, of the present invention or a composition comprising the xylanase, e.g. a feed additive composition, and another component which is suitable for human or animal consumption and is capable of providing a medical or physiological benefit to the consumer.

In one embodiment the "another component" may be one or more further enzymes (e.g. further feed enzymes or brewing or malting enzymes, or grain processing enzymes or wheat gluten-starch separation enzymes).

Suitable additional enzymes for use in the present invention may be one or more of the enzymes selected from the group consisting of: endoglucanases (E.C. 3.2.1.4); cellobiohydrolases (E.C. 3.2.1.91), β-glucosidases (E.C. 3.2.1.21), cellulases (E.C. 3.2.1.74), lichenases (E.C. 3.1.1.73), lipases (E.C. 3.1.1.3), lipid acyltransferases (generally classified as E.C. 2.3.1.x), phospholipases (E.C. 3.1.1.4, E.C. 3.1.1.32 or E.C. 3.1.1.5), phytases (e.g. 6-phytase (E.C. 3.1.3.26) or a 3-phytase (E.C. 3.1.3.8), amylases, alpha-amylases (E.C. 3.2.1.1), other xylanases (E.C. 3.2.1.8, E.C. 3.2.1.32, E.C. 3.2.1.37, E.C. 3.1.1.72, E.C. 3.1.1.73), glucoamylases (E.C. 3.2.1.3), hemicellulases, proteases (e.g. subtilisin (E.C. 3.4.21.62) or a bacillolysin (E.C. 3.4.24.28) or an alkaline serine protease (E.C. 3.4.21.x) or a keratinase (E.C. 3.4.x.x)), debranching enzymes, cutinases, esterases and/or mannanases (e.g. a β-mannanase (E.C. 3.2.1.78)).

In one embodiment (particularly for feed applications) the other component may be one or more of the enzymes selected from the group consisting of an amylase (including α-amylases (E.C. 3.2.1.1), G4-forming amylases (E.C. 3.2.1.60), β-amylases (E.C. 3.2.1.2) and γ-amylases (E.C. 3.2.1.3)); and/or a protease (e.g. subtilisin (E.C. 3.4.21.62) or a bacillolysin (E.C. 3.4.24.28) or an alkaline serine protease (E.C. 3.4.21.x) or a keratinase (E.C. 3.4.x.x)) and/or a phytase (e.g. a 6-phytase (E.C. 3.1.3.26) or a 3-phytase (E.C. 3.1.38)).

In one embodiment (particularly for feed applications) the other component may be a combination of an amylase (e.g. α-amylases (E.C. 3.2.1.1)) and a protease (e.g. subtilisin (E.C. 3.4.21.62)).

In one embodiment (particularly for feed applications) the other component may be a β-glucanase, e.g. an endo-1,3 (4)-β-glucanases (E.C. 3.2.1.6).

In one embodiment (particularly for feed applications) the other component may be a phytase (e.g. a 6-phytase (E.C. 3.1.3.26) or a 3-phytase (E.C. 3.1.38).

In one embodiment (particularly for feed applications) the other component may be a mannanases (e.g. a β-mannanase (E.C. 3.2.1.78)).

In one embodiment (particularly for feed applications) the other component may be a lipase lipase (E.C. 3.1.1.3), a lipid acyltransferase (generally classified as E.C. 2.3.1.x), or a phospholipase (E.C. 3.1.1.4, E.C. 3.1.1.32 or E.C. 3.1.1.5), suitably a lipase (E.C. 3.1.1.3).

In one embodiment (particularly for feed applications) the other component may be a protease (e.g. subtilisin (E.C. 3.4.21.62) or a bacillolysin (E.C. 3.4.24.28) or an alkaline serine protease (E.C. 3.4.21.x) or a keratinase (E.C. 3.4.x.x)).

In one embodiment the additional component may be a stabiliser or an emulsifier or a binder or carrier or an excipient or a diluent or a disintegrant.

The term "stabiliser" as used here is defined as an ingredient or combination of ingredients that keeps a product (e.g. a feed product) from changing over time.

The term "emulsifier" as used herein refers to an ingredient (e.g. a feed ingredient) that prevents the separation of emulsions. Emulsions are two immiscible substances, one present in droplet form, contained within the other. Emulsions can consist of oil-in-water, where the droplet or dispersed phase is oil and the continuous phase is water; or water-in-oil, where the water becomes the dispersed phase and the continuous phase is oil. Foams, which are gas-in-liquid, and suspensions, which are solid-in-liquid, can also be stabilised through the use of emulsifiers.

As used herein the term "binder" refers to an ingredient (e.g. a feed ingredient) that binds the product together through a physical or chemical reaction. During "gelation" for instance, water is absorbed, providing a binding effect. However, binders can absorb other liquids, such as oils, holding them within the product. In the context of the present invention binders would typically be used in solid or low-moisture products for instance baking products: pastries, doughnuts, bread and others. Examples of granulation binders include one or more of: polyvinylpyrrolidone, hydroxypropylmethylcellulose (HPMC), hydroxypropylcellulose (HPC), sucrose, maltose, gelatin and acacia.

"Carriers" mean materials suitable for administration of the enzyme and include any such material known in the art such as, for example, any liquid, gel, solvent, liquid diluent, solubilizer, or the like, which is non-toxic and which does not interact with any components of the composition in a deleterious manner.

The present invention provides a method for preparing a composition (e.g. a feed additive composition) comprising admixing an enzyme of the present invention with at least one physiologically acceptable carrier selected from at least one of maltodextrin, limestone (calcium carbonate), cyclodextrin, wheat or a wheat component, sucrose, starch, $Na_2SO_4$, Talc, PVA, sorbitol, benzoate, sorbiate, glycerol, sucrose, propylene glycol, 1,3-propane diol, glucose, parabens, sodium chloride, citrate, acetate, phosphate, calcium, metabisulfite, formate and mixtures thereof.

Examples of "excipients" include one or more of: microcrystalline cellulose and other celluloses, lactose, sodium citrate, calcium carbonate, dibasic calcium phosphate, glycine, starch, milk sugar and high molecular weight polyethylene glycols.

Examples of "disintegrants" include one or more of: starch (preferably corn, potato or tapioca starch), sodium starch glycollate, croscarmellose sodium and certain complex silicates.

Examples of "diluents" include one or more of: water, ethanol, propylene glycol and glycerin, and combinations thereof.

The other components may be used simultaneously (e.g. when they are in admixture together or even when they are delivered by different routes) or sequentially (e.g. they may be delivered by different routes) to the xylanase of the present invention.

Preferably, when the feed additive composition of the present invention is admixed with another component(s), the DFM remains viable.

In one embodiment preferably the feed additive composition according to the present invention does not comprise chromium or organic chromium In one embodiment preferably the feed additive according to the present invention does not contain glucanase.

In one embodiment preferably the feed additive according to the present invention does not contain sorbic acid.

Isolated

In one aspect, preferably the amino acid sequence, or nucleic acid, or enzyme according to the present invention is in an isolated form. The term "isolated" means that the sequence or enzyme or nucleic acid is at least substantially free from at least one other component with which the sequence, enzyme or nucleic acid is naturally associated in nature and as found in nature. The sequence, enzyme or nucleic acid of the present invention may be provided in a form that is substantially free of one or more contaminants with which the substance might otherwise be associated. Thus, for example it may be substantially free of one or more potentially contaminating polypeptides and/or nucleic acid molecules.

Purified

In one aspect, preferably the sequence, enzyme or nucleic acid according to the present invention is in a purified form. The term "purified" means that the given component is present at a high level. The component is desirably the predominant component present in a composition. Preferably, it is present at a level of at least about 90%, or at least about 95% or at least about 98%, said level being determined on a dry weight/dry weight basis with respect to the total composition under consideration.

Nucleotide Sequence

The scope of the present invention encompasses nucleotide sequences encoding proteins having the specific properties as defined herein.

The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or anti-sense strand.

The term "nucleotide sequence" in relation to the present invention includes genomic DNA, cDNA, synthetic DNA, and RNA. Preferably it means DNA, more preferably cDNA sequence coding for the present invention.

In one embodiment the term "nucleotide sequence" means cDNA.

In a preferred embodiment, the nucleotide sequence when relating to and when encompassed by the per se scope of the present invention does not include the native nucleotide sequence according to the present invention when in its natural environment and when it is linked to its naturally associated sequence(s) that is/are also in its/their natural environment. For ease of reference, we shall call this preferred embodiment the "non-native nucleotide sequence". In this regard, the term "native nucleotide sequence" means an entire nucleotide sequence that is in its native environment and when operatively linked to an entire promoter with which it is naturally associated, which promoter is also in its native environment. However, the amino acid sequence encompassed by scope the present invention can be isolated and/or purified post expression of a nucleotide sequence in its native organism. Preferably, however, the amino acid sequence encompassed by scope of the present invention may be expressed by a nucleotide sequence in its native organism but wherein the nucleotide sequence is not under the control of the promoter with which it is naturally associated within that organism.

Typically, the nucleotide sequence encompassed by the scope of the present invention is prepared using recombinant DNA techniques (i.e. recombinant DNA). However, in an alternative embodiment of the invention, the nucleotide sequence could be synthesised, in whole or in part, using chemical methods well known in the art (see Caruthers M H et al., (1980) *Nuc Acids Res Symp Ser* 215-23 and Horn T et al., (1980) *Nuc Acids Res Symp Ser* 225-232).

Preparation of the Nucleotide Sequence

A nucleotide sequence encoding either a protein which has the specific properties as defined herein or a protein which is suitable for modification may be identified and/or isolated and/or purified from any cell or organism producing said protein. Various methods are well known within the art for the identification and/or isolation and/or purification of nucleotide sequences. By way of example, PCR amplification techniques to prepare more of a sequence may be used once a suitable sequence has been identified and/or isolated and/or purified.

By way of further example, a genomic DNA and/or cDNA library may be constructed using chromosomal DNA or messenger RNA from the organism producing the enzyme. If the amino acid sequence of the enzyme is known, labelled oligonucleotide probes may be synthesised and used to identify enzyme-encoding clones from the genomic library prepared from the organism. Alternatively, a labelled oligonucleotide probe containing sequences homologous to another known enzyme gene could be used to identify enzyme-encoding clones. In the latter case, hybridisation and washing conditions of lower stringency are used.

Alternatively, enzyme-encoding clones could be identified by inserting fragments of genomic DNA into an expression vector, such as a plasmid, transforming enzyme-negative bacteria with the resulting genomic DNA library, and then plating the transformed bacteria onto agar plates containing a substrate for enzyme (i.e. arabinoxylan), thereby allowing clones expressing the enzyme to be identified.

In a yet further alternative, the nucleotide sequence encoding the enzyme may be prepared synthetically by established standard methods, e.g. the phosphoroamidite method described by Beucage S. L. et al., (1981) *Tetrahedron Letters* 22, p 1859-1869, or the method described by Matthes et al., (1984) *EMBO J.* 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al., (*Science* (1988) 239, pp 487-491).

Amino Acid Sequences

The scope of the present invention also encompasses amino acid sequences of enzymes having the specific properties as defined herein.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The amino acid sequence may be prepared/isolated from a suitable source, or it may be made synthetically or it may be prepared by use of recombinant DNA techniques.

Preferably the amino acid sequence when relating to and when encompassed by the per se scope of the present invention is not a native enzyme. In this regard, the term "native enzyme" means an entire enzyme that is in its native environment and when it has been expressed by its native nucleotide sequence.

Sequence Identity or Sequence Homology

The present invention also encompasses the use of sequences having a degree of sequence identity or sequence homology with amino acid sequence(s) of a polypeptide having the specific properties defined herein or of any nucleotide sequence encoding such a polypeptide (hereinafter referred to as a "homologous sequence(s)"). Here, the term "homologue" means an entity having a certain homology with the subject amino acid sequences and the subject nucleotide sequences. Here, the term "homology" can be equated with "identity".

The homologous amino acid sequence and/or nucleotide sequence should provide and/or encode a polypeptide which retains the functional activity and/or enhances the activity of the enzyme.

In the present context, in some embodiments a homologous sequence is taken to include an amino acid or a nucleotide sequence which may be at least 97.7% identical, preferably at least 98 or 99% identical to the subject sequence.

In some embodiments a homologous sequence is taken to include an amino acid or a nucleotide sequence which may be at least 85% identical, preferably at least 90 or 95% identical to the subject sequence.

Typically, the homologues will comprise the same active sites etc. as the subject amino acid sequence for instance. Although homology can also be considered in terms of similarity (i.e. amino acid residues having similar chemical properties/functions), in the context of the present invention it is preferred to express homology in terms of sequence identity.

In one embodiment, a homologous sequence is taken to include an amino acid sequence or nucleotide sequence which has one or several additions, deletions and/or substitutions compared with the subject sequence.

In the present context, "the subject sequence" relates to the nucleotide sequence or polypeptide/amino acid sequence according to the invention.

Preferably, the % sequence identity with regard to a polypeptide sequence is determined using SEQ ID No. 1 as the subject sequence in a sequence alignment. In one embodiment, the polypeptide subject sequence is selected from the group consisting of SEQ ID No. 1, SEQ ID No. 26, SEQ ID No. 27, SEQ ID No. 3, SEQ ID No 28, SEQ ID No. 29, or SEQ ID No. 5.

Preferably, the % sequence identity with regard to a nucleotide sequence is determined using SEQ ID No. 2 as the subject sequence in the sequence alignment. In one embodiment, the subject sequence for nucleotide sequences may be selected from the group consisting of SEQ ID No. 2, SEQ ID No. 24, SEQ ID No. 25, SEQ ID No. 4, SEQ ID No. 30, SEQ ID No. 31, SEQ ID No. 6, SEQ ID No 32 or SEQ ID No. 33.

A "parent nucleic acid" or "parent amino acid" means a nucleic acid sequence or amino acid sequence, encoding or coding for the parent polypeptide, respectively.

In one embodiment the present invention relates to a protein whose amino acid sequence is represented herein or a protein derived from this (parent) protein by substitution, deletion or addition of one or several amino acids, such as 2, 3, 4, 5, 6, 7, 8, 9 amino acids, or more amino acids, such as 10 or more than 10 amino acids in the amino acid sequence of the parent protein and having the activity of the parent protein.

Suitably, the degree of identity with regard to an amino acid sequence is determined over at least 20 contiguous amino acids, preferably over at least 30 contiguous amino acids, preferably over at least 40 contiguous amino acids, preferably over at least 50 contiguous amino acids, preferably over at least 60 contiguous amino acids, preferably over at least 100 contiguous amino acids, preferably over at least 200 contiguous amino acids.

In one embodiment the present invention relates to a nucleic acid sequence (or gene) encoding a protein whose amino acid sequence is represented herein or encoding a protein derived from this (parent) protein by substitution, deletion or addition of one or several amino acids, such as 2, 3, 4, 5, 6, 7, 8, 9 amino acids, or more amino acids, such as 10 or more than 10 amino acids in the amino acid sequence of the parent protein and having the activity of the parent protein.

In the present context, in one embodiment a homologous sequence or foreign sequence is taken to include a nucleotide sequence which may be at least 97.7% identical, preferably at least 98 or 99% identical to a nucleotide sequence encoding a polypeptide of the present invention (the subject sequence).

In another embodiment, a homologous sequence is taken to include a nucleotide sequence which may be at least 85% identical, preferably at least 90 or 95% identical to a nucleotide sequence encoding a polypeptide of the present invention (the subject sequence).

Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology or % identity between two or more sequences.

% homology or % identity may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology or % identity when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons.

Calculation of maximum % homology or % identity therefore firstly requires the production of an optimal alignment, taking into consideration gap penalties. A suitable computer program for carrying out such an alignment is the Vector NTI (Invitrogen Corp.). Examples of software that can perform sequence comparisons include, but are not limited to, the BLAST package (see Ausubel et al 1999 Short Protocols in Molecular Biology, 4th Ed—Chapter 18), BLAST 2 (see FEMS Microbiol Lett 1999 174(2): 247-50; FEMS Microbiol Lett 1999 177(1): 187-8 and tatiana@ncbi.nlm.nih.gov), FASTA (Altschul et al 1990 J. Mol. Biol. 403-410) and AlignX for example. At least BLAST, BLAST 2 and FASTA are available for offline and online searching (see Ausubel et al 1999, pages 7-58 to 7-60), such as for example in the GenomeQuest search tool (www.genomequest.com).

Although the final % homology or % identity can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI package.

Alternatively, percentage homologies may be calculated using the multiple alignment feature in Vector NTI (Invitrogen Corp.), based on an algorithm, analogous to CLUSTAL (Higgins D G & Sharp P M (1988), Gene 73(1), 237-244).

Once the software has produced an optimal alignment, it is possible to calculate % homology, preferably % sequence identity. The software typically does this as part of the sequence comparison and generates a numerical result.

Should Gap Penalties be used when determining sequence identity, then preferably the following parameters are used for pairwise alignment:

| FOR BLAST | |
|---|---|
| GAP OPEN | 9 |
| GAP EXTENSION | 2 |

| FOR CLUSTAL | DNA | PROTEIN |
|---|---|---|
| Weight Matrix | IUB | Gonnet 250 |
| GAP OPENING | 15 | 10 |
| GAP EXTEND | 6.66 | 0.1 |

In one embodiment, CLUSTAL may be used with the gap penalty and gap extension set as defined above.

Suitably, the degree of identity with regard to a nucleotide sequence or protein sequence is determined over at least 20 contiguous nucleotides/amino acids, preferably over at least 30 contiguous nucleotides/amino acids, preferably over at least 40 contiguous nucleotides/amino acids, preferably over at least 50 contiguous nucleotides/amino acids, preferably over at least 60 contiguous nucleotides/amino acids, preferably over at least 100 contiguous nucleotides/amino acids.

Suitably, the degree of identity with regard to a nucleotide sequence is determined over at least 100 contiguous nucleotides, preferably over at least 200 contiguous nucleotides, preferably over at least 300 contiguous nucleotides, preferably over at least 400 contiguous nucleotides, preferably over at least 500 contiguous nucleotides, preferably over at least 600 contiguous nucleotides, preferably over at least 700 contiguous nucleotides, preferably over at least 800 contiguous nucleotides.

Suitably, the degree of identity with regard to a nucleotide sequence may be determined over the whole sequence taught herein.

Suitably, the degree of identity with regard to a nucleotide sequence may be determined over the whole sequence taught herein as the mature sequence, e.g. SEQ ID No. 2 or SEQ ID No. 24 or SEQ ID No. 25 or SEQ ID No. 4, SEQ ID No. 30, SEQ ID No. 31, SEQ ID No. 6, SEQ ID No 32 or SEQ ID No. 33. Suitably, the degree of identity with regard to a nucleotide sequence may be determined over the whole sequence as taught herein as SEQ ID No. 2.

Suitably, the degree of identity with regard to a protein (amino acid) sequence is determined over at least 100 contiguous amino acids, preferably over at least 200 contiguous amino acids, preferably over at least 300 contiguous amino acids.

Suitably, the degree of identity with regard to an amino acid or protein sequence may be determined over the whole sequence taught herein.

Suitably, the degree of identity with regard to an amino acid or protein sequence may be determined over the whole sequence taught herein as the mature sequence, e.g. SEQ ID No. 1, SEQ ID No. 26, SEQ ID No. 27, SEQ ID No. 3, SEQ ID No. 28, SEQ ID No. 29, or SEQ ID No. 5. Suitably, the degree of identity with regard to an amino acid or protein sequence may be determined over the whole sequence taught herein as SEQ ID No. 1.

In the present context, the term "query sequence" means a homologous sequence or a foreign sequence, which is aligned with a subject sequence in order to see if it falls within the scope of the present invention. Accordingly, such query sequence can for example be a prior art sequence or a third party sequence.

In one preferred embodiment, the sequences are aligned by a global alignment program and the sequence identity is calculated by identifying the number of exact matches identified by the program divided by the length of the subject sequence.

In one embodiment, the degree of sequence identity between a query sequence and a subject sequence is determined by 1) aligning the two sequences by any suitable alignment program using the default scoring matrix and default gap penalty, 2) identifying the number of exact matches, where an exact match is where the alignment program has identified an identical amino acid or nucleotide in the two aligned sequences on a given position in the alignment and 3) dividing the number of exact matches with the length of the subject sequence.

In yet a further preferred embodiment, the global alignment program is selected from the group consisting of CLUSTAL and BLAST (preferably BLAST) and the sequence identity is calculated by identifying the number of exact matches identified by the program divided by the length of the subject sequence.

The sequences may also have deletions, insertions or substitutions of amino acid residues result in a functionally equivalent substance. Deliberate amino acid substitutions may be made on the basis of similarity in polarity, charge, solubility, hydrophobicity, hydrophilicity, and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| | | |
|---|---|---|
| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ε-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid # and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

In one embodiment the xylanase for use in the present invention may comprise a polypeptide sequence shown as SEQ ID No. 17, SEQ ID No. 18, SEQ ID No. 19, SEQ ID No. 20, or SEQ ID No. 21 with a conservative substitution of at least one of the amino acids.

Suitably there may be at least 2 conservative substitutions, such as at least 3 or at least 4 or at least 5.

Suitably there may be less than 15 conservative substitutions, such as less than 12, less than 10, or less than 8 or less than 5 conservative substitutions.

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences of the present invention.

The present invention also encompasses the use of nucleotide sequences that are complementary to the sequences presented herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other homologues may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. The primers may be designed to contain suitable restriction enzyme recognition sites so that the amplified DNA can be cloned into a suitable cloning vector.

Amino Acid Numbering

In the present invention, a specific numbering of amino acid residue positions in the xylanases used in the present invention may be employed. By alignment of the amino acid sequence of a sample xylanases with the xylanase of the present invention (particularly SEQ ID No. 1) it is possible to allot a number to an amino acid residue position in said sample xylanase which corresponds with the amino acid residue position or numbering of the amino acid sequence shown in SEQ ID No. 1 of the present invention.

Hybridisation

The present invention also encompasses sequences that are complementary to the nucleic acid sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridising to the sequences that are complementary to the sequences presented herein, or any fragment or derivative thereof.

The term "variant" also encompasses sequences that are complementary to sequences that are capable of hybridising to the nucleotide sequences presented herein.

Preferably, the term "variant" encompasses sequences that are complementary to sequences that are capable of hybridising under stringent conditions (e.g. 50° C. and 0.2×SSC {1×SSC=0.15 M NaCl, 0.015 M Na$_3$citrate pH 7.0}) to the nucleotide sequences presented herein.

More preferably, the term "variant" encompasses sequences that are complementary to sequences that are capable of hybridising under high stringency conditions (e.g. 65° C. and 0.1×SSC {1×SSC=0.15 M NaCl, 0.015 M Na$_3$citrate pH 7.0}) to the nucleotide sequences presented herein.

The present invention also relates to nucleotide sequences that can hybridise to the nucleotide sequences of the present invention (including complementary sequences of those presented herein).

The present invention also relates to nucleotide sequences that are complementary to sequences that can hybridise to the nucleotide sequences of the present invention (including complementary sequences of those presented herein).

Preferably hybridisation is analysed over the whole of the sequences taught herein.

Expression of Enzymes

The nucleotide sequence for use in the present invention may be incorporated into a recombinant replicable vector. The vector may be used to replicate and express the nucleotide sequence, in protein/enzyme form, in and/or from a compatible host cell.

Expression may be controlled using control sequences e.g. regulatory sequences.

The protein produced by a host recombinant cell by expression of the nucleotide sequence may be secreted or may be contained intracellularly depending on the sequence and/or the vector used. The coding sequences may be designed with signal sequences which direct secretion of the substance coding sequences through a particular prokaryotic or eukaryotic cell membrane.

Expression Vector

The term "expression vector" means a construct capable of in vivo or in vitro expression.

Preferably, the expression vector is incorporated into the genome of a suitable host organism. The term "incorporated" preferably covers stable incorporation into the genome.

The nucleotide sequence of the present invention may be present in a vector in which the nucleotide sequence is operably linked to regulatory sequences capable of providing for the expression of the nucleotide sequence by a suitable host organism.

The vectors for use in the present invention may be transformed into a suitable host cell as described below to provide for expression of a polypeptide of the present invention.

The choice of vector e.g. a plasmid, cosmid, or phage vector will often depend on the host cell into which it is to be introduced.

The vectors for use in the present invention may contain one or more selectable marker genes—such as a gene, which confers antibiotic resistance e.g. ampicillin, kanamycin, chloramphenicol or tetracyclin resistance. Alternatively, the selection may be accomplished by co-transformation (as described in WO91/17243).

Vectors may be used in vitro, for example for the production of RNA or used to transfect, transform, transduce or infect a host cell.

Thus, in a further embodiment, the invention provides a method of making nucleotide sequences of the present invention by introducing a nucleotide sequence of the present invention into a replicable vector, introducing the vector into a compatible host cell, and growing the host cell under conditions which bring about replication of the vector.

The vector may further comprise a nucleotide sequence enabling the vector to replicate in the host cell in question. Examples of such sequences are the origins of replication of plasmids pUC19, pACYC177, pUB110, pE194, pAMB1 and pIJ702.

Regulatory Sequences

In some applications, the nucleotide sequence for use in the present invention is operably linked to a regulatory sequence which is capable of providing for the expression of the nucleotide sequence, such as by the chosen host cell. By way of example, the present invention covers a vector comprising the nucleotide sequence of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding the enzyme of the present invention may also be achieved by the selection of heterologous regulatory regions, e.g. promoter, secretion leader and terminator regions.

Preferably, the nucleotide sequence according to the present invention is operably linked to at least a promoter.

Other promoters may even be used to direct expression of the polypeptide of the present invention.

Examples of suitable promoters for directing the transcription of the nucleotide sequence in a bacterial, fungal or yeast host are well known in the art.

The promoter can additionally include features to ensure or to increase expression in a suitable host. For example, the features can be conserved regions such as a Pribnow Box or a TATA box.

Constructs

The term "construct"—which is synonymous with terms such as "conjugate", "cassette" and "hybrid"—includes a nucleotide sequence for use according to the present invention directly or indirectly attached to a promoter.

An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker, which allows for the selection of the genetic construct.

For some applications, preferably the construct of the present invention comprises at least the nucleotide sequence of the present invention operably linked to a promoter.

Host Cells

The term "host cell"—in relation to the present invention includes any cell that comprises either the nucleotide sequence or an expression vector as described above and which is used in the recombinant production of a protein having the specific properties as defined herein.

In one embodiment the organism is an expression host.

Thus, a further embodiment of the present invention provides host cells transformed or transfected with a nucleotide sequence that expresses the protein of the present invention. The cells will be chosen to be compatible with the said vector and may for example be prokaryotic (for example bacterial), fungal or yeast cells.

Examples of suitable bacterial host organisms are gram positive or gram negative bacterial species.

In one embodiment the xylanases taught herein are expressed in the expression host *Trichoderma reesei*.

In some embodiments the expression host for the xylanases taught herein may be one or more of the following fungal expression hosts: *Fusarium* spp. (such as *Fusarium oxysporum*); *Aspergillus* spp. (such as *Aspergillus niger, A. oryzae, A. nidulans*, or *A. awamori*) or *Trichoderma* spp. (such as *T. reesei*).

In some embodiments the expression host may be one or more of the following bacterial expression hosts: *Streptomyces* spp. or *Bacillus* spp. (e.g. *Bacillus subtilis* or *B. licheniformis*). The use of suitable host cells—such as yeast and fungal host cells—may provide for post-translational modifications (e.g. myristoylation, glycosylation, truncation, lipidation and tyrosine, serine or threonine phosphorylation) as may be needed to confer optimal biological activity on recombinant expression products of the present invention.

Organism

The term "organism" in relation to the present invention includes any organism that could comprise the nucleotide sequence coding for the polypeptide according to the present invention and/or products obtained therefrom, and/or wherein a promoter can allow expression of the nucleotide sequence according to the present invention when present in the organism.

In one embodiment the organism is an expression host.

Suitable organisms may include a prokaryote, fungus, yeast or a plant.

The term "transgenic organism" in relation to the present invention includes any organism that comprises the nucleotide sequence coding for the polypeptide according to the present invention and/or the products obtained therefrom, and/or wherein a promoter can allow expression of the nucleotide sequence according to the present invention within the organism. Preferably the nucleotide sequence is incorporated in the genome of the organism.

The term "transgenic organism" does not cover native nucleotide coding sequences in their natural environment when they are under the control of their native promoter which is also in its natural environment.

Therefore, the transgenic organism of the present invention includes an organism comprising any one of, or combinations of, the nucleotide sequence coding for the polypeptide according to the present invention, constructs according to the present invention, vectors according to the present invention, plasmids according to the present invention, cells according to the present invention, tissues according to the present invention, or the products thereof.

For example the transgenic organism may also comprise the nucleotide sequence coding for the polypeptide of the present invention under the control of a heterologous promoter.

Transformation of Host Cells/Organism

As indicated earlier, the host organism can be a prokaryotic or a eukaryotic organism. Examples of suitable prokaryotic hosts include *E. coli, Streptomyces* spp. and *Bacillus* spp., e.g. *Bacillus subtilis*.

Teachings on the transformation of prokaryotic hosts is well documented in the art, for example see Sambrook et al (Molecular Cloning: A Laboratory Manual, 2nd edition, 1989, Cold Spring Harbor Laboratory Press). If a prokaryotic host is used then the nucleotide sequence may need to be suitably modified before transformation—such as by removal of introns.

Filamentous fungi cells may be transformed using various methods known in the art—such as a process involving protoplast formation and transformation of the protoplasts followed by regeneration of the cell wall in a manner known. The use of *Aspergillus* as a host microorganism is described in EP 0 238 023.

Transformation of prokaryotes, fungi and yeasts are generally well known to one skilled in the art.

A host organism may be a fungus—such as a mould. Examples of suitable such hosts include any member belonging to the genera *Trichoderma* (e.g. *T. reesei*), *Thermomyces, Acremonium, Fusarium, Aspergillus, Penicillium, Mucor, Neurospora* and the like.

In one embodiment, the host organism may be a fungus. In one preferred embodiment the host organism belongs to the genus *Trichoderma*, e.g. *T. reesei*).

Culturing and Production

Host cells transformed with the nucleotide sequence of the present invention may be cultured under conditions conducive to the production of the encoded polypeptide and which facilitate recovery of the polypeptide from the cells and/or culture medium.

The medium used to cultivate the cells may be any conventional medium suitable for growing the host cell in questions and obtaining expression of the polypeptide.

The protein produced by a recombinant cell may be displayed on the surface of the cell.

The protein may be secreted from the host cells and may conveniently be recovered from the culture medium using well-known procedures.

Secretion

Often, it is desirable for the protein to be secreted from the expression host into the culture medium from where the protein may be more easily recovered. According to the present invention, the secretion leader sequence may be selected on the basis of the desired expression host. Hybrid signal sequences may also be used with the context of the present invention.

Large Scale Application

In one preferred embodiment of the present invention, the amino acid sequence is used for large scale applications.

Preferably the amino acid sequence is produced in a quantity of from 1 g per liter to about 100 g per liter of the total cell culture volume after cultivation of the host organism.

Suitably the amino acid sequence may be produced in a quantity of from 30 g per liter to about 90 g per liter of the total cell culture volume after cultivation of the host organism.

General Recombinant DNA Methodology Techniques

The present invention employs, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA* Methods in Enzymology, Academic Press. Each of these general texts is herein incorporated by reference.

The invention will now be described, by way of example only, with reference to the following Figures and Examples.

EXAMPLES

Example 1

Materials and Methods
Plasmid and Library Construction

Figure 20:
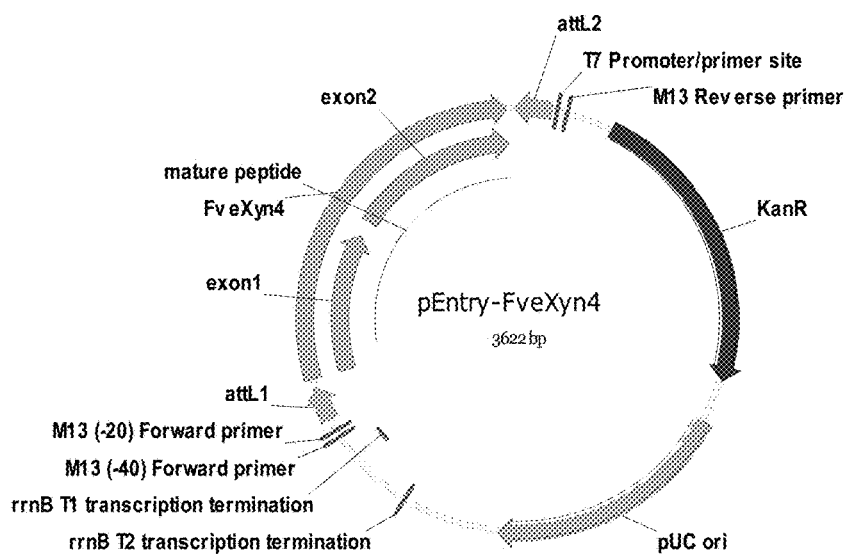
FIG. 20 shows the schematic map of pEntry-FveXyn4.

A DNA sequence containing the coding region for xylanase 4 (the family GH10) from the filamentous fungus *Fusarium verticilloides*, FveXyn4, was amplified from the genomic DNA with the gene specific primers extended with the attB1 and attB2 sites to allow for the Gateway® BP recombination cloning into the pDonor221 vector (Invitrogen, USA). The pEntry-FveXyn4 plasmid, as shown in FIG. 20 was used by the vendors BaseClear (Netherlands) and Geneart GmH (Germany) as template for construction of combinatorial libraries.

Variants of FveXyn4 was generated either as combinatorial libraries or by introduction of specific mutations and were designed to included different numbers and combinations of the mutations presented in Table 1. Variant A, B, C, D, and E and variants of Example 12 were all included in these variants.

Figure 21:
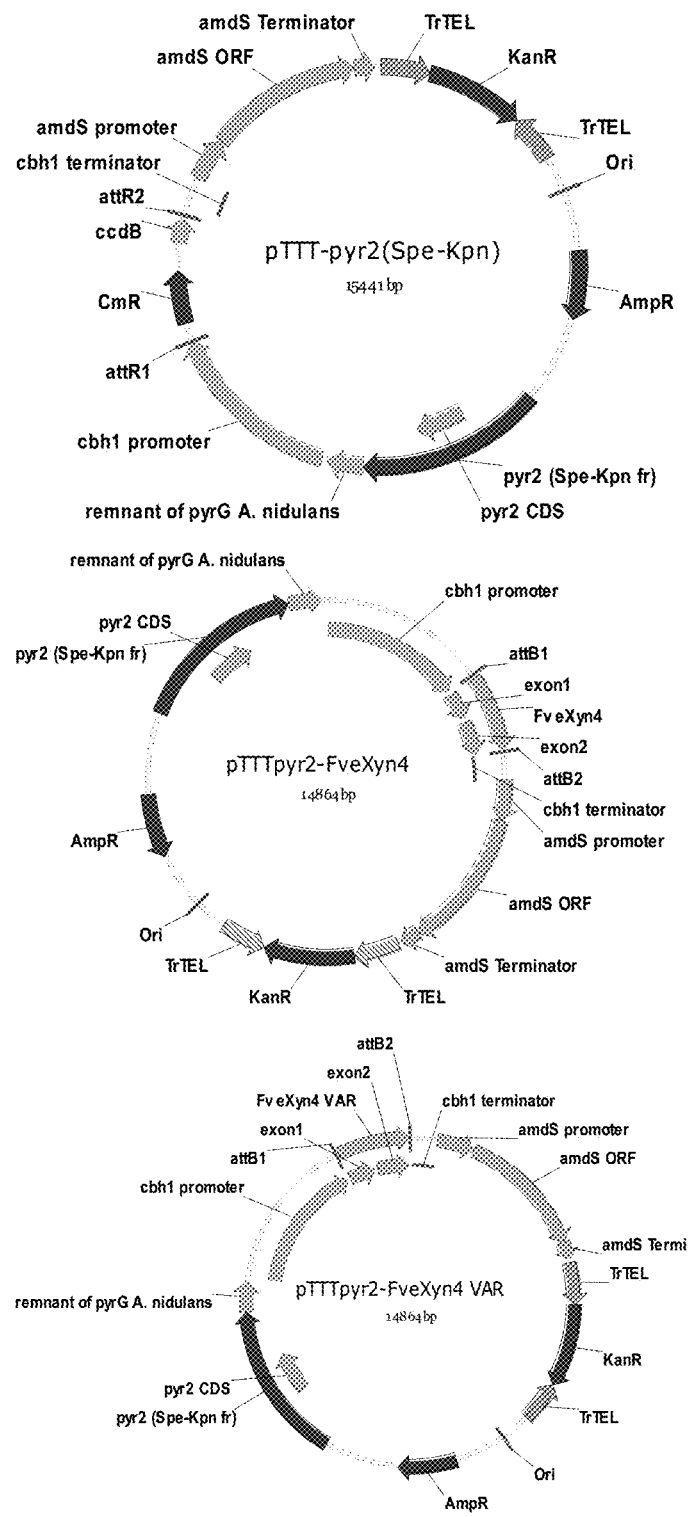
FIG. 21 shows schematic maps of the destination pTTTpyr2 vector and expression vectors for the FveXyn4 (pTTTpyr2-FveXyn4) and FveXyn4 variants (pTTTpyr2-FveXyn4_VAR).

Combinatorial variants were generated via the Gateway® recombination technique (Invitrogen, USA) with the destination vector pTTTpyr2 (FIG. 21). The resulting expression plasmids pTTTpyr2-FveXyn4_VAR expressing Xyn4 with different mutations were amplified in the *Escherichia coli* DH5a strain, purified, sequenced, arrayed individually in 96 MTPs and used for fungal transformation as described further. The expression vector contains the *T. reesei* cbhI promoter and terminator regions allowing for a strong inducible expression of a gene of interest, the *Aspergillus nidulans* amdS and *T. reesei* pyr2 selective markers conferring growth of transformants on minimal medium with acetamide in the absence of uridine. The plasmids are maintained autonomously in the fungal cell due to *T. reesei* derived telomere regions. Usage of replicative plasmids results in increased frequencies of transformation and circumvents problems of locus-dependent expression observed with integrative fungal transformation.

Specific mutations were introduced into the genomic sequence of the *Fusarium verticilloides* xylanase Xyn4 via a de novo gene synthesis (GeneArt GmbH, Germany). Synthetic variants were then cloned by the vendor into the destination vector pTTT-pyr2 via a Gateway recombination technique (Invitrogen, Carlsbad, Calif., USA).

Fungal Strains, Growth Media and Transformation

Expression plasmids (5-10 ul) were transformed using a PEG-protoplast method into a *T. reesei* strain deleted for major cellulases and xylanase 2 (Δcbh1 Δcbh2 Δegl1 Δegl2 Δegl3 Δegl4 Δegl5 Δegl6 Δbgl1 Δman1 Δxyn2 Prdiv: iRNAxyn1 xyn3: amdS pyr2-). Additional downregulation of the endogenous xylanase 1 and 3 background was further achieved via introducing into the host strain genome an iRNA interference cassette targeting to shut down the xyn1 and xyn3 expression simultaneously. All high throughput transformations were performed robotically in a 24 well MTP format using Biomek robots (Beckman Coulter, USA). Plasmids with variants were received from the vendors in 96 well MTPs arrayed according to a predetermined layout. Transformation mixtures containing approximately 1 μg of DNA and $5\times10^6$ protoplasts in a total volume of 50 μl were treated with 200 ul of 25% PEG solution, diluted with 1 volumes of 1.2M sorbitol/10 mM Tris, pH7.5/10 mM $CaCl_2$ solution, rearranged robotically into 24 well MTPs and mixed with 1 ml of 3% agarose Minimal Medium containing 1M sorbitol and 10 mM NH4Cl. After growth of transformants, spores from each well were pooled and repatched on fresh 24 well MTPs with MM containing acetamide for additional selective pressure. Once sporulated, spores were harvested and used for inoculation of liquid cultures either in a 24-well MTP format or shake flasks in the following production medium: 37 g/L glucose, 1 g/L sophorose, 9 g/L casmino acids, 10 g/L $(NH_4)_2SO_4$, 5 g/L $KH_2PO_4$, 1 g/L $CaCl_2\times2H_2O$, 1 g/L $MgSO_4\times7H_2O$, 33 g/L 1,4-Piperazinebis(propanesulfonic acid), pH 5.5, 2.5 ml/L of 400× *T. reesei* trace elements (175 g/L citric acid, 200 g/L FeSO4×$7H_2O$, 16 g/L ZnSO4×$7H_2O$, 3.2 g/L CuSO4×$5H_2O$, 1.4 g/L MnSO4×$H_2O$, 0.8 g/L boric acid). 1 ml of production medium was added to produce variants in 24 well MTPs. For shake flasks, volumes were scaled up.

Plates were grown for 6 days at 28° C. and 80% humidity with shaking at 200 rpm. Culture supernatants were harvested by vacuum filtration and used to assay their performance as well as expression level.

For larger scale production fermentation in a 6 Liter autoclaveable Continuers Stirred Reactor was conducted. Shake flasks were inoculated with spores and incubated with shaking for 3 days at 28° C. in the following shake flask medium: 5 g/L $(NH_4)_2SO_4$, 4.5 g/L $KH_2PO_4$, 1 g/L $MgSO_4\times7H_2O$, 14.4 g/L citric acid×$1H_2O$, 1 g/L $CaCl_2\times2H_2O$, 27.5 g/L glucose, 1 drop antifoam agent (EROL DF 6000K). The pH was adjusted with NaOH (2M) to 5.5 and media was autoclaved 20 minutes at 122° C. After cooling 2.5 ml/L of 400× *T. reesei* trace elements (175 g/L citric acid, 200 g/L FeSO4×$7H_2O$, 16 g/L ZnSO4×$7H_2O$, 3.2 g/L CuSO4×$5H_2O$, 1.4 g/L MnSO4×$H_2O$, 0.8 g/L boric acid) was added. Cells from the shake flask was used to inoculate the bioreactor containing the following Bioreactor medium: 4.7 g/L $KH_2PO_4$, 1 g/L $MgSO_4\times7H_2O$, 4.3 g/L $(NH_4)_2SO_4$, 45 g/L glucose, 0.7 g/L $CaCl_2\times2H_2O$, 0.3 g/L antifoam agent (EROL DF 6000K), 2.5 ml/L of 400× *T. reesei* trace elements (175 g/L citric acid, 200 g/L FeSO4×$7H_2O$, 16 g/L ZnSO4×$7H_2O$, 3.2 g/L CuSO4×$5H_2O$, 1.4 g/L MnSO4×$H_2O$, 0.8 g/L boric acid). Temperature was controlled at 34° C.; pH was continuously controlled by adding 20% ammoniumhydroxide. Dissolved oxygen was controlled to minimum 40% saturation by varying the stirring rate. Off gas carbon dioxide and oxygen content were measured. When the initial glucose was depleted a constant feeding of a glucose/sophorose was started. At the same time temperature was reduced to and controlled at 28° C., pH was increased to and controlled at 4.5. The fermentation was terminated after 140 hours. Broth was removed from the tank, and cells were removed by filtration. After cell separation the filtrate was concentrated by ultrafiltration. Finally, the concentrate was sterile filtered and used for pelleting stability studies.

Enzyme Samples

Xylanase activity of culture supernatants from MTP were measured using the method for measurement of xylanase activity as described below. Culture supernatants were diluted 20 and 130 times in 25 mM sodium acetate, 250 mM NaCl, pH 4.0. 25 μL diluted enzyme sample was mixed with 150 μL 0.5% WE-AX substrate, pH 5.0 and incubated at 30° C. for 15 min with shaking. After incubation, 45.4 μL reaction sample was mixed with 135 μL PAHBAH working solution and incubated at 95° C. for 5 min before cooled to 20° C. for 10 sec. 100 μL sample was transferred to a microtiter plate well and the plate was read at 410 nm.

The activity was calculated as the mean of three replicates subtracted a blank including 25 mM sodium acetate, 250 mM NaCl, pH 4.0 instead of enzyme. Protein concentration of the samples were calculated based on a standard curve of purified FveXyn4 (SEQ ID No. 1). All samples were diluted to 50 ppm in 25 mM sodium acetate, 250 mM NaCl, pH 4.0. These normalised samples were used as enzyme stock solution in assays described below.

Protein concentration in the enzyme stock solution was measured by HPLC as described below.

Xylanase activity of sterile filtered concentrates from large scale production was measured by the following activity assay. 0.5 g of each concentrate was weighed in 100 ml volumetric flasks followed by filling to volume with McIlvaine buffer, pH 5.0. Samples were diluted to app. 6 XU/ml using McIlvaine buffer, pH 5.0. 100 µl of diluted sample was added to 1 ml of McIlvaine buffer, pH 5.0 in test tubes and equilibrated at 40° C. for 2 min. A Xylazyme tablet (100 mg) was added to initiate the reaction and samples were incubated at 40° C. for 10 min before the reaction was stopped by adding 10 ml of 2% Tris, pH 12.0. The solution was mixed using vortex, left to stand for 5 min and mixed again before centrifuged at 3500 rpm for 10 min. Absorbance of the supernatant was measured at 590 nm. Each sample was measured in duplicate. Xylanase activity was quantified relatively to an enzyme standard (Danisco Xylanase, available from Danisco Animal Nutrition).

The benchmark enzyme Econase® XT is a commercially available and was extracted from commercial dry formulated samples. The xylanase component from Econase® XT commercial dry formulated samples was extracted in a 33% (w/w) slurry using McIlvain buffer, pH 5.0. The extract was cleared using centrifugation (3000 RCF for 10 min) and filtered using a PALL Acrodisc PF syringe filter (0.8/0.2 µm Supor membrane) and subsequently heated 20 min at 70° C. After removable of precipitation by centrifugation (38 724 RCF for 15 min) the buffer was replaced by passage through a Sephadex G25 column (PD10 from Pharmacia) equilibrated with 20 mM Na Citrate, 20 mM NaCl, pH 3.4. Purification of the xylanase component was performed using Source 15S resin, followed by elution with a linear increasing salt gradient (NaCl in 20 mM Na Citrate buffer pH 3.4).

Econase XT® is an endo-1,4-β-xylanase (EC 3.2.1.8) produced by the strain Trichoderma reesei RF5427 (CBS 114044), available from ABVista.

Protein concentration was determined by measuring absorption at 280 nm. The extinction coefficients were estimates from the amino acid sequences. For Econase XT the absorption at 280 nm of 1 mg/ml was calculated to be 2.84 AU.

Protein Determination by HPLC

A MTP (Agilent Part no. 5042-1385) containing 100 µL enzyme stock solution with an approximate concentration of 50 ppm per well was used for the High Performance Liquid Chromatography (HPLC) protein determination method. An Agilent 1260 or 1290 (Hewlett Packard) HPLC equipped with an Acuity UPLC BEH 125 SEC (Waters) column was used to separate remaining contaminants. Sample was eluted from the column using 25 mM sodium phosphate buffer pH 6.8 containing 250 mM sodium chloride. Absorbance was measured at 220 nm, integrated using ChemStation software (Agilent Technologies) and the protein concentration of samples was determined based on a standard curve of purified FveXyn4 protein/enzyme having the amino acid sequence of SEQ ID No. 1.

Measurement of Xylanase Activity

The xylanase activity of enzyme samples was determined by measuring amount of reducing sugars released from hydrolysed wheat WE-AX (water extractable arabinoxylan). The amount of reducing sugars was measured by PAHBAH-method. Briefly, by heat and alkaline conditions the reducing end groups react with the colorless PAHBAH (4-Para-Hydroxybenzoic Acid Hydrazide), whereby PAHBAH is oxidized and absorbance is measured at 410 nm (Lever, 1972).

0.5% WE-AX substrate, pH 5.0 was prepared by moisturizing 0.25 g soluble wheat arabinoxylan (e.g. Megazyme, high viscosity ~43 cSt, P-WAXYH) with 2.5 ml 96% Ethanol, before adding 50 ml 0.1 M sodium acetate, pH 5.0. Standard activity determination was carried out at pH 5.0. For measurement at other pH values, the 50 ml 0.1 M sodium acetate, pH 5.0 was substituted with the indicated buffer. The solution was heated under stirring to boiling, and cooled under stirring to RT.

PAHBAH working solution was prepared by mixing 5% PAHBAH (4-Hydroxybenzhydrazide, e.g. Sigma-Aldrich H9882) stock solution in 0.5 M HCl with 0.5 M NaOH at a 1:4 (v/v) ratio. The solution was prepared on the day of analysis and protected from light.

Enzyme samples were diluted in the indicated buffer to a concentration of 1 ug/ml prior to analysis. 25 µL diluted enzyme sample was mixed with 150 µL 0.5% WE-AX substrate, pH 5.0 and incubated at 30° C. for 15 min with shaking. After incubation, 45.4 µL reaction sample was mixed with 135 µL PAHBAH working solution and incubated at 95° C. for 5 min before cooled to 20° C. for 10 sec. 100 µL sample was transferred to a microtiter plate well and the plate was read at 410 nm.

The activity was calculated as the mean of three replicates subtracted a blank including appropriate dilution buffer instead of enzyme.

Assay for Measurement of Thermostability

The thermal denaturation profiles of the FveXyn4 variants was measured by diluting and pre-incubating the enzyme samples in 25 mM MES buffer (0.00125% Tween 80-25 mM MES buffer, pH 6.0, 0.00125% (V:V) Tween 80), pH 6.0 for 10 min at varying temperatures (66, 66.7, 68.2, 70.6, 73.5, 76.8, 79.7, 81.9, 83.5, 84.6, and 85° C., respectively) and subsequently measuring the residual activity by the xylanase activity method described above. Activity measured without pre-incubation was set to 100% and the residual activity of each variant at each temperature was calculated as relative to this. Tm value is calculated from the thermal denaturation profiles as the temperature at which 50% residual activity is obtained.

pH Profile

The pH profile of the FveXyn4 variants was studied by measuring activity at pH 4.0, 5.0 and 6.0. Activity was measured essentially as described in the xylanase activity method described above. Enzyme samples were diluted in 0.1 M Na-Acetate, pH 4.0, 0.1 M Na-Acetate, pH 5.0, 0.1% BSA (e.g. Sigma A7906), or McIlvaine buffer, pH 6.0, for activity at pH 4.0, 5.0 or 6.0, respectively prior to analysis. 0.5% WE-AX substrate at pH 4.0 and 6.0 was prepared as described for 0.5% WE-AX substrate, pH 5.0, though 0.1 M sodium acetate, pH 5.0 was substituted with 0.1 M Na-Acetate, pH 4.0 or McIlvaine buffer, pH 6.0, respectively. All data are calculated as relative to FveXyn4 at pH 5.0.

Pentosan Solubilisation (AXinsol Solubilisation)

The substrate used for measuring pentosan solubilisation by FveXyn4 variants was corn DDGS and wheat bran. 100 mg cDDGS or wheat bran with particle size <212 µm was transferred to a 2 ml Eppendorf tube and the precise weight was recorded. 750 µl incubation buffer (200 mM HEPES, 100 mM NaCl, 2 mM $CaCl_2$, pH 6.0) and 900 µl chloramphenicol (40 µg/ml in incubation buffer) was added. Increasing enzyme dosages was added to make a total volume of 1.8 ml.

Each sample was assayed in doublets in parallel with a control sample (without enzyme). The samples were incubated at 40° C. with shaking. After 18 hours of incubation the supernatant was filtered using 96 wells filterplates (Pall Corporation, AcroPrep 96 Filter Plate, 1.0 µm Glass, NTRL, 1 mL well). After filtration the samples were stored at 4° C. until analysis for total amount of C5 sugars, arabinose and xylose.

Quantification of C5 Sugars (Pentosans)

The total amount of pentoses brought into solution was measured using the method of Rouau and Surget (1994) with a continuous flow injection apparatus. The supernatants were treated with acid to hydrolyse polysaccharides to monosugars. Phloroglucinol (1, 3, 5-trihydroxybenzen) was added for reaction with monopentoses and monohexoses, which forms a coloured complex.

By measuring the difference in absorbance at 550 nm compared to 510 nm, the amount of pentoses in the solution was calculated using a standard curve. Unlike the pentose-phloroglucinol complex, the absorbance of the hexose-phloroglucinol complex is constant at these wavelengths. Glucose was added to the phloroglucinol solution to create a constant glucose signal and further ensure no interference from hexose sugars. The pentose concentration in the samples was determined using a xylose standard curve.

Viscosity Reduction in In Vitro Animal Model Assay

Viscosity reduction on wheat was determined using a modified version of the procedure described by Bedford & Classen (1993 Poultry Sci., 72, 137-143). 3.6 mL of pepsin solution (2000 U/mL in 0.1 N HCl) was mixed with 2.4 g wheat prior to addition of the indicated amount of xylanase (FveXyn4 variants) followed by 45 min incubation at 40° C. 1.2 ml pancreatin solution (8 mg/mL in 1 M MES, pH 6.8) was then mixed into the slurry resulting in a final pH of 6.0. The sample was allowed to incubate for 60 min at 40° C. with mixing after 30 and 60 min. The sample was then placed on ice for 5 min to stop the reaction and centrifuged 10 min at 3320 RCF followed by filtration through a 0.45 µm filter to obtain a clear supernatant. Sample viscosity was then measured at 20° C. using a Brookfield digital viscometer (model DV-I+, Brookfield Engineering Laboratories, Stoughton, Mass. 02172, USA) fitted with a CPE-40 cone and plate. Each data point is the average of three repetitions.

Pelleting Stability

Pelleting trials were performed in full scale at Technological Institute, Kolding, Denmark. Each sterile filtered xylanase concentrate was formulated on wheat and mixed into a corn/soy feed mix (61.1% Corn, 31.52% Hipro Soya 48, 4.00% Soya Oil, 0.40% Sodium Bicarbonate, 0.25% Vitamins/Minerals Leghennen, 0.20% DL-methionine, 1.46% Dicalcium Phosphate, 1.16% Limestone). A premix was prepared by mixing the xylanase variants formulated on wheat into 10 kg corn/soy feed mix and mixed for 10 min. The premix was then added to 120 kg feed and mixed for 10 min before conditioning. Feed was conditioned for 30 sec at 90 and 95° C. before pelleting. The mash and resulting feed pellets were grinded using a Perten laboratory mill (it is important that all samples are ground the same), before xylanase activity in the samples were analyzed according to either the extract or slurry method described below using azurine cross linked arabinoxylan from wheat (e.g. Xylazyme tablets, Megazyme, Ireland) as substrate.

Extract method: 5.0 g of ground sample was mixed with 50 ml McIlvaine buffer, pH 5.0 and stirred on a magnetic stirrer for 10 min. The extract was filtered through a glass fiber filter and diluted 3-6 times in 50 ml McIlvaine buffer, pH 5.0. 100 µl diluted extract was mixed with 400 µL McIlvaine buffer, pH 5.0 and equilibrated at 50° C. for 2 min. A Xylazyme tablet (60 mg) was added to initiate the reaction and samples were incubated at 50° C. for 60 min before the reaction was stopped by adding 5 ml of 2% Tris, pH 12.0. The solution was mixed using vortex, left to stand for 5 min and mixed again before centrifuged at 3500 rpm for 10 min. Absorbance of the supernatant was measured at 590 nm. Each sample was measured in duplicate.

Xylanase activity was quantified using a xylanase standard curve prepared by using each of the xylanase variant on blank (no enzyme) mash and 90° C. feed. The respective wheat formulated xylanase was extracted for 10 min in Mc Ilvaine buffer, pH 5.0 to obtain a concentration of 160 XU/mL. The extract was filtered through a glass fiber filter and hereafter 0, 200, 400, 600, 800, and 1000 µL extract was added to 5.0 g samples of ground blank mash and 90° C. feed. Xylanase activity in these standard samples was measured as described in the extract method above. Each standard curve was prepared once.

Slurry method: 1.0 g of ground sample was mixed with 50 ml McIlvaine buffer, pH 5.0 and stirred on a magnetic stirrer in a water bath at 50° C. for 2 min. A Xylazyme tablet (100 mg) was added to initiate the reaction and samples were incubated with stirring at 50° C. for 20 min (30 min for Variant B). After incubation the samples were filtered through a glass fiber filter and absorbance of the supernatant was measured at 590 nm. Each sample was measured in duplicate.

Xylanase activity was quantified using a xylanase standard curve prepared for each of the xylanase variants on blank mash feed (no enzyme). The respective wheat formulated xylanase was extracted for 10 min in Mc Ilvaine buffer pH 5.0 to obtain a concentration of 30 XU/mL. The extract was filtered through a glass fiber filter and hereafter 0, 200, 400, 600, 800, and 1000 µL was added to 1.0 g samples of ground blank mash feed. Xylanase activity in these standard samples was measured as described in the slurry method above. The standard curve was prepared once.

Recovery measured in mash feed was set to 100% and the residual activity of 90 and 95° C. feed was calculated as relative to this.

Results and Discussion

Following a significant undertaking five variants of the backbone xylanase FveXyn4 were identified.

Figure 11:
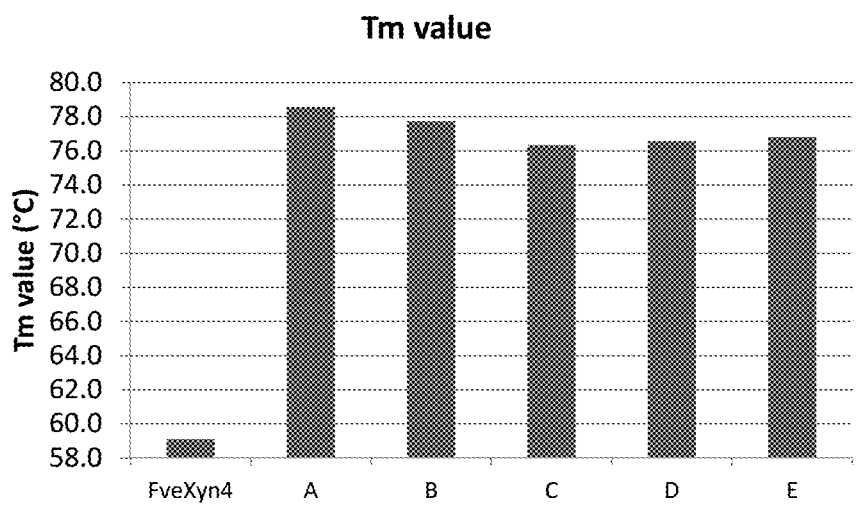
FIG. 11 shows the Tm value of the 5 variants A, B, C, D, and E compared to FveXyn4. Tm value is measured as the temperature at which 50% residual activity is obtained after 10 min incubation.

The five variants are all extremely more thermostable than the benchmark/parental molecule, FveXyn4, as shown in FIG. 11.

Further characterization of the variant on biochemical and performance properties important for a xylanase to be used in for example feed applications identified these variants as being ones which were both thermostable and had good performance/biochemical activity.

TABLE 1

Overview of mutations in the five variants of FveXyn4

Variants Mutations

A     N7D_N25P_T33V_S57Q_N62T_K79Y_S89G_T103M_V115L_N147Q_G181Q_S193Y_A217Q_G219P_T298Y
B     N7D_N25P_T33V_S57Q_N62T_G64T_K79Y_T103M_V115L_N147Q_G181Q_S193Y_A217Q_G219P_T298Y
C     N7D_N25P_T33V_K79Y_S89G_A217Q_T298Y
D     N7D_T33V_S57Q_N62T_G64T_K79Y_S89G_A217Q_T298Y
E     N7D_N25P_T33V_G64T_K79Y_S89G_A217Q_T298Y

Numbering is based on the mature sequence of FveXyn4. SEQ ID No. 1.

FIG. 11 shows the Tm value of the 5 variants A, B, C, D, and E compared to FveXyn4. Tm value is measured as the temperature at which 50% residual activity is obtained after 10 min incubation.

Figure 12:
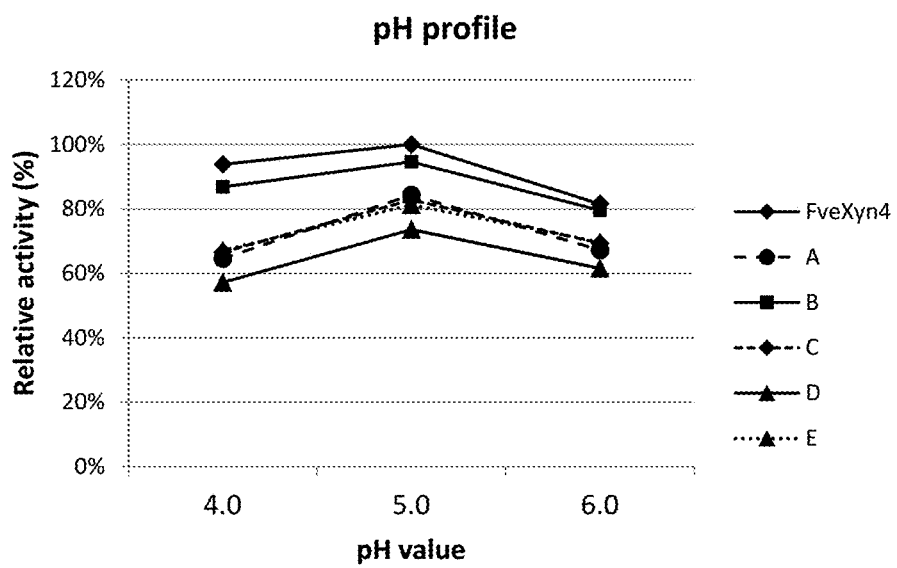
FIG. 12 shows pH profile of the five variants measured at pH 4.0, 5.0 and 6.0 and all data are relative to FveXyn4 at pH 5.0.

FIG. 12 shows pH profile of the five variants measured at pH 4.0, 5.0 and 6.0 and all data are relative to wild type at pH 5.0. All five variants have a pH profile that is ideal for use in, for example, feed applications.

Figure 13A:
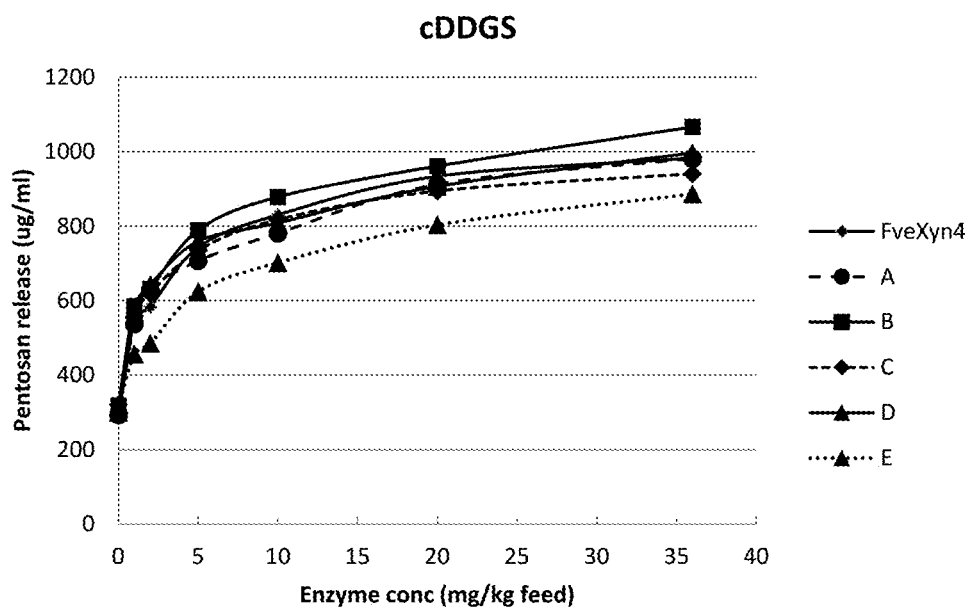
FIGS. 13*a* and *b* show solubilisation of pentosan from cDDGS (top—FIG. 13*a*) and wheat bran (bottom FIG. 13*b*) as function of xylanase dosage.
Figure 13B:
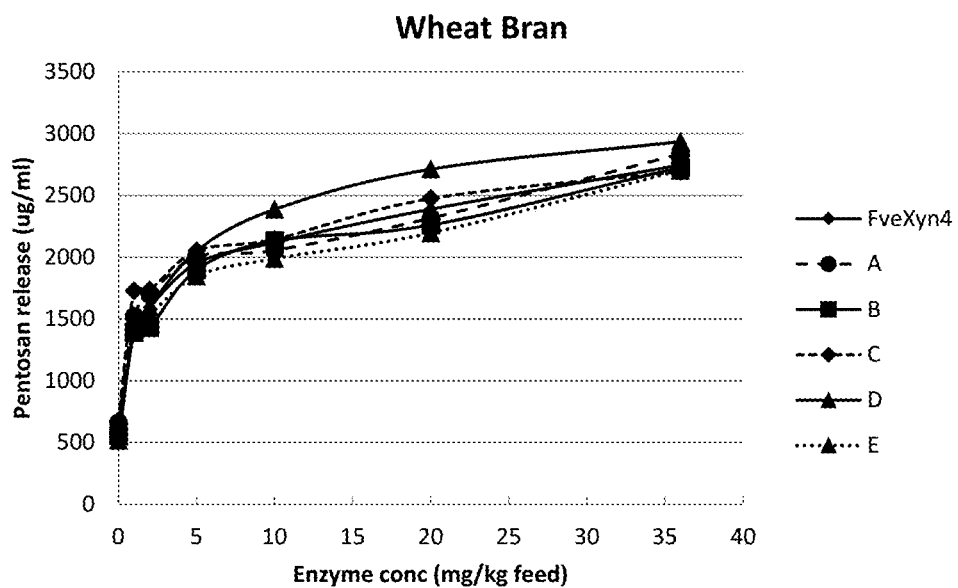

FIGS. 13a and 13b show dose response curves on pentosan solubilisation from corn DDGS and wheat bran, respectively by the five variants. All five variants show a high ability to solubilize arabinoxylan (pentosan) from both DDGS and wheat bran and all on the same level as the wt molecule. All five variants are very suitable for use in for example animal feed.

Figure 14:
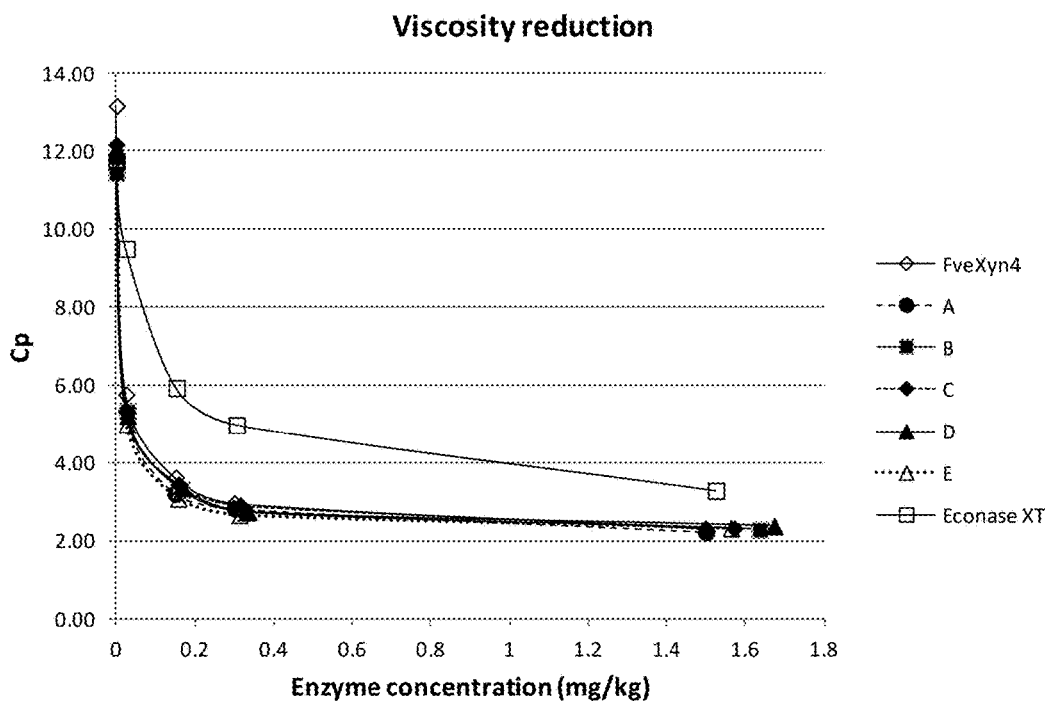
FIG. 14 shows viscosity reduction in the Viscosity reduction in in vitro animal model assay taught in Example 1 by the variants of the present invention and compared to FveXyn4 and the benchmark Econase XT. The viscosity reduction is measured on high viscosity wheat.
Figure 15:
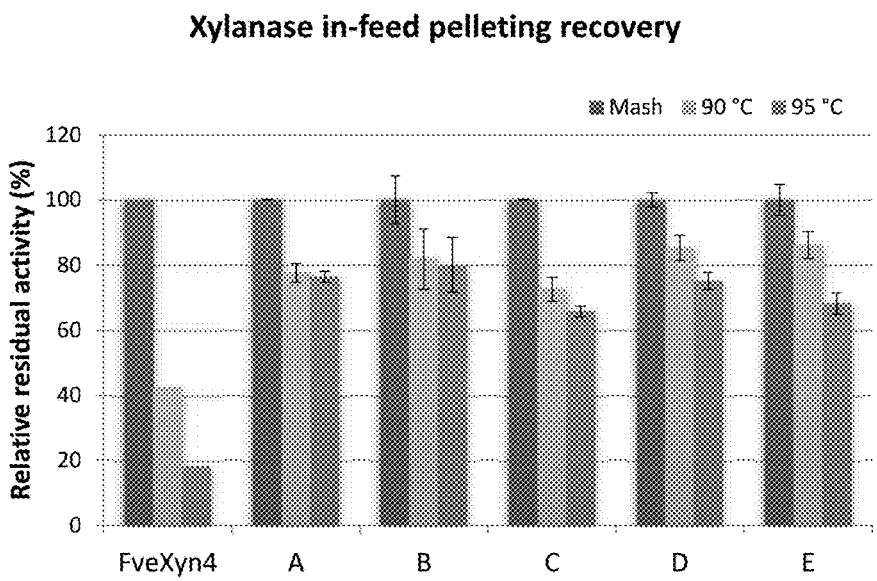
FIG. 15 shows xylanase recovery after in-feed pelleting at 90 and 95° C. Activity is shown as relative to mash sample. Samples containing FveXyn4 was analyzed using the extract method, whereas samples containing variant A-E was analyzed using the slurry method, both methods described in materials and methods of Example 1.
Figure 16:
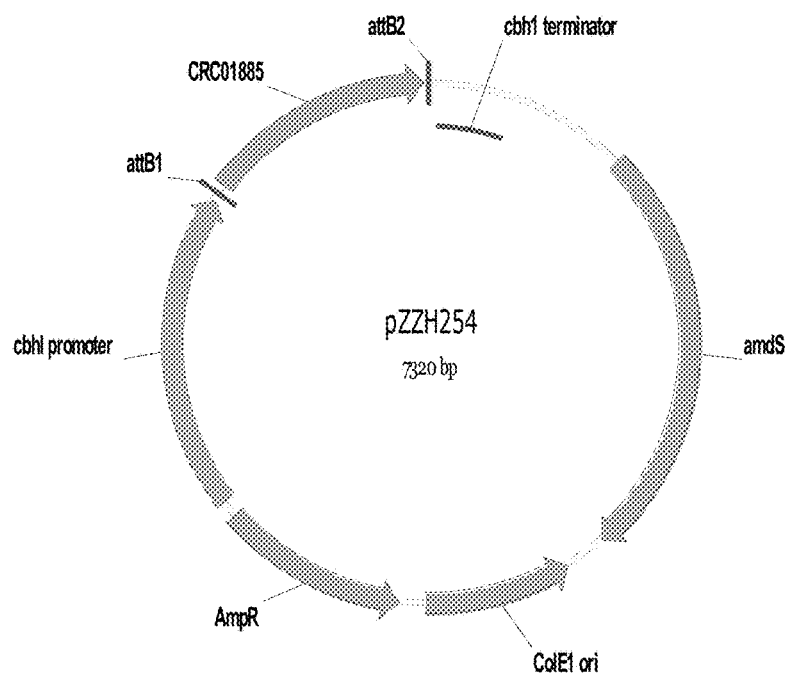
FIG. 16 shows a plasmid map of pZZH254.

FIG. 14 shows viscosity reduction in the "Viscosity reduction in in vitro animal model assay" taught in Example 1. All five variants show a high ability to reduce viscosity and all on the same level as the wt molecule and were much better than the benchmark Econase XT FIG. 15 shows in-feed xylanase recovery after pelleting at 90 and 95° C. All five variants show high recovery of xylanase after pelleting and significantly higher than wild type.

Example 2

Cloning of *Fusarium verticillioides* Backbone (Parent) Xylanase (FveXyn4)

Genomic DNA isolated from a strain of *Fusarium verticillioides* was used for amplifying a xylanase gene. The sequence of the cloned gene, called the FveXyn4 gene, is depicted in SEQ ID No. 2. The mature protein encoded by the FveXyn4 gene is depicted in SEQ ID No. 1. The protein product of gene FveXyn4 belongs to glycosyl hydrolase family 10 (GH10) based on the PFAM search (http://pfam.sanger.ac.uk/).

Example 3

Expression of FveXyn4 Backbone (Parent) Protein

The FveXyn4 gene was amplified from genomic DNA of *Fusarium verticillioides* using the following primers: Primer 1 5'-caccATGAAGCTGTCTTCTTTCCTCTA-3' (SEQ ID No. 22), and Primer 2 5'-TTTTTAGCGGAGAGCGTTGACAACAGC-3' (SEQ ID No. 23). The PCR product was cloned into pENTR/D-TOPO vector (Invitrogen K2400) to generate the FveXyn4 pEntry plasmid. The expression plasmid pZZH254 was obtained by Gateway cloning reaction between the FveXyn4 pEntry plasmid and pTrex3gM expression vector (described in US 2011/0136197 A1) using Gateway® LR Clonase® II enzyme kit (Invitrogen 11791). A map of plasmid pZZH254 is provided as FIG. 16. The sequence of the FveXyn4 gene was confirmed by DNA sequencing (SEQ ID No. 2). The plasmid pZZH254 was transformed into a quad deleted *Trichoderma reesei* strain (described in WO 05/001036) using biolistic method (Te'o V S et al., J Microbiol Methods, 51:393-9, 2002).

Following sequence confirmation, protoplasts of a quad deleted *T. reesei* strain (described in WO 05/001036) were transformed with the expression plasmid pZZH254 using the PEG protoplast method (Penttila et al, *Gene,* 61:155-164, 1987). For protoplast preparation, spores were grown for about 10 hours at 24° C. in *Trichoderma* Minimal Medium MM (20 g/L glucose, 15 g/L $KH_2PO_4$, pH 4.5, 5 g/L $(NH_4)2SO_4$, 0.6 g/L $MgSO_4{\times}7H_2O$, 0.6 g/L $CaCl_2{\times}2H_2O$, 1 ml of 1000× *T. reesei* Trace elements solution (175 g/L Citric Acid anhydrous, 200 g/L $FeSO_4{\times}7H_2O$, 16 g/L $ZnSO_4{\times}7H_2O$, 3.2 g/L $CuSO_4$, 1.4 g/L $MnSO_4$×H2O, and 0.8 g/L Boric Acid). Germinating spores were harvested by centrifugation and treated with 30 mg/mL Vinoflow FCE (Novozymes, AG Switzerland) solution for from 7 hours to overnight at 30° C. at 100 rpm to lyse the fungal cell walls. Protoplasts were washed in 0.1 M Tris HCl buffer (pH 7) containing 0.6 M sorbitol and resuspended in 10 mM Tris HCl buffer (pH 7.5) containing 1.2 M sorbitol and 10 mM calcium chloride. For PEG transformation, approximately 1 μg of DNA and $1\text{-}5{\times}10^7$ protoplasts in a total volume of 200 μl were treated with 2 ml of 25% PEG solution, diluted with 2 volumes of 1.2 M sorbitol/10 mM Tris, pH 7.5/10 mM $CaCl_2$ solution. Transformants were selected on a medium containing acetamide as a sole source of nitrogen (acetamide 0.6 g/L; cesium chloride 1.68 g/L; glucose 20 g/L; potassium dihydrogen phosphate 15 g/L; magnesium sulfate heptahydrate 0.6 g/L; calcium chloride dihydrate 0.6 g/L; iron (II) sulfate 5 mg/L; zinc sulfate 1.4 mg/L; cobalt (II) chloride 1 mg/L; manganese (II) sulfate 1.6 mg/L; agar 20 g/L; pH 4.25). Transformed colonies (about 50-100) appeared in about 1 week. After growth on acetamide plates, the spores were collected and reselected on acetamide plates. After 5 days, the spores were collected using 10% glycerol, and $1{\times}10^8$ spores were inoculated in a 250 ml shake flask with 30 ml Glucose/Sophorose defined medium for protein expression. Protein expression was confirmed by SDS-PAGE. The spore suspension was subsequently grown in a 7 L fermentor in a defined medium containing 60% glucose-sophorose feed. Glucose/Sophorose defined medium (per liter) consists of $(NH_4)2SO_4$ 5 g, PIPPS buffer 33 g, Casamino Acids 9 g, $KH_2PO_4$ 4.5 g, $CaCl_2$ (anhydrous) 1 g, $MgSO_4.7H_2O$ 1 g, pH to 5.5 adjusted with 50% NaOH with Milli-Q $H_2O$ to bring to 966.5 mL. After sterilization, the following were added: 26 mL 60% Glucose/Sophrose, and 400× *T. reesei* Trace Metals 2.5 mL.

FveXyn4 was purified from concentrated fermentation broth of a 7 L fermentor culture using two chromatography columns. Concentrated fermentation broth buffered in 20 mM sodium phosphate buffer pH 6.0 containing 1 M ammonium sulfate was loaded on a hydrophobic interaction chromatography column (Sepharose Phenyl FF, 26/10). The protein was eluted from the column using a linear gradient of equilibration/wash buffer to 20 mM sodium phosphate buffer pH 6.0. The fraction containing FveXyn4 protein was loaded onto a gel filtration column (HiLoad Superdex 75 pg 26/60), and the mobile phase used was 20 mM sodium phosphate, pH 7.0, containing 0.15 M NaCl. The purified protein was concentrated using a 3K Amicon Ultra-15 device and the concentrated protein fraction was used in further studies.

The nucleotide sequence of FveXyn4 gene is set forth as SEQ ID No. 24. The signal sequence is shown in bold (upper case), and the predicted intron is shown in bold and lower-case.

The amino acid sequence of FveXyn4 protein is set forth as SEQ ID No. 26. The signal sequence predicted by SignalP-NN software is shown underlined. This is the pre-pro-protein.

The amino acid sequence of the mature form of FveXyn4 protein is set forth as SEQ ID No. 1. This is the active form of the enzyme. SEQ ID No. 27 shows the pro-protein, i.e. before post-translational modification. Depending on the host the post-translation modification may vary and therefore the present invention also encompasses mature, active forms of SEQ ID No. 27.

Example 4

Xylanase Activity of FveXyn4 (a Parent Xylanase)

FveXyn4 belongs to the glycosyl hydrolase 10 family (GH10, CAZy number). The beta 1-4 xylanase activity of FveXyn4 was measured using 1% xylan from birch wood (Sigma 95588) or 1% arabinoxylan from wheat flour (Megazyme P-WAXYM) as substrates. The assay was performed in 50 mM sodium citrate pH 5.3, 0.005% Tween-80 buffer at 50° C. for 10 minutes.

The released reducing sugar was quantified by reaction with 3, 5-Dinitrosalicylic acid and measurement of absorbance at 540 nm. The enzyme activity is quantified relative to a xylose standard curve. In this assay, one xylanase unit (U) is defined as the amount of enzyme required to generate 1 micromole of xylose reducing sugar equivalents per minute under the conditions of the assay.

Example 5

Temperature Profile of FveXyn4 (a Parent Xylanase)

Figure 17:
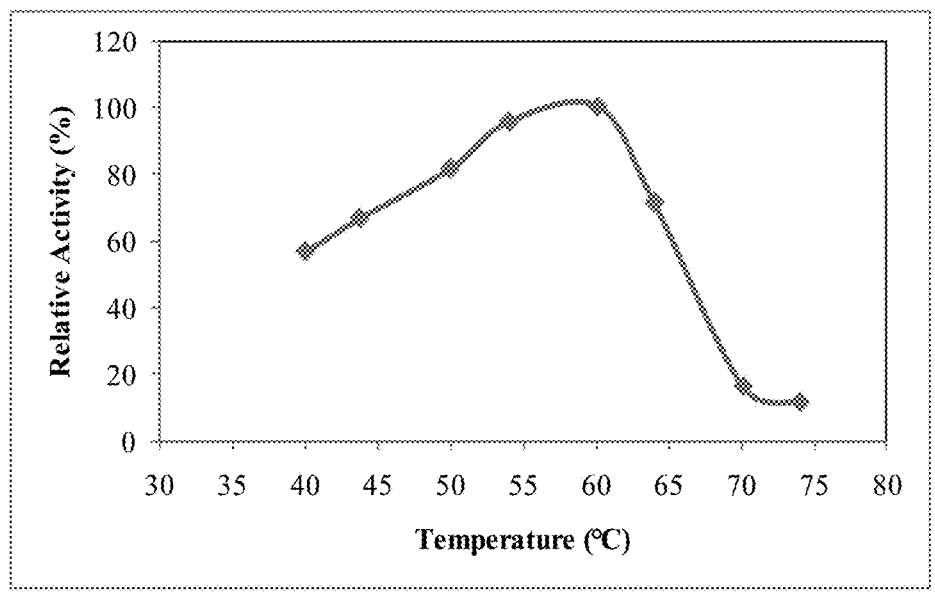
FIG. 17 shows the temperature profile of FveXyn4.

The temperature optimum of purified FveXyn4 (a parent enzyme) was determined by assaying for xylanase activity at temperatures varying between 40° C. and 75° C. for 10 minutes in 50 mM sodium citrate buffer at pH 5.3. The activity was reported as relative activity where the activity at the temperature optimum was set to 100%. The temperature profile of FveXyn4 is shown in FIG. 17. FveXyn4 was found to have an optimum temperature of 60° C., and was found to retain greater than 70% of maximum activity between 45° C. and 64° C.

Example 6

Viscosity Reduction in Grain-Based Material (e.g. for Biofuel Production)

Wheat Viscosity Reduction

In the European fuel alcohol industry, small grains like wheat, barley and rye are common raw materials, in contrast to the US where mainly corn is used. These small grains contain, next to starch, high levels of non-starch polysaccharide polymers (NSP), like cellulose, beta-glucan and hemicellulose.

The ratio in which the different NSPs are represented differ for each feedstock. Table 1 shows the different amounts of NSPs in wheat, barley and rye compared to some other feedstocks.

TABLE 1

Non-starch Polysaccharides present in different feedstocks (g kg$^{-1}$ dry matter) [1,2]

|  | Corn | Wheat | Rye | Barley | | Oats | |
|---|---|---|---|---|---|---|---|
|  |  |  |  | Hulled | Hulless | Hulled | Hulless |
| Beta-Glucan | 1 | 8 | 16 | 42 | 42 | 28 | 41 |
| Cellulose | 22 | 17-20 | 15-16 | 43 | 10 | 82 | 14 |
| Soluble and Non-soluble NCP[3] | 75 | 89-99 | 116-136 | 144 | 114 | 150 | 113 |
| Total NSP | 97 | 107-119 | 132-152 | 186 | 124 | 232 | 116 |

[1] (Bach Knudsen, 1997) Carbohydrate and lignin contents of plant materials used in animal feeding. Anim. Feed Sci. Technol., 67 (4): 319-338
[2] Englyst, H. N., Anderson, V. and Cummings, J. H., 1983. Starch and non-starch polysaccharides in some cereal foods. J. Sci. Food Agric., 34: 1434-1440.
[3] Non Cellulosic Polysaccharides: pentosans, (arabino)xylans and other hemicelluloses NSPs give high viscosity to grain mashes. High viscosity has a negative impact on ethanol production since it will limit the solid concentration that can be used in mashing and it will reduce the energy efficiency of the process. In addition, residual hemicelluloses present throughout the process may contribute to fouling in heat exchangers and distillation equipment. The largest impact of a high viscosity is seen when a mash is cooled to fermentation temperature (32° C.). This explains that the viscosity needs to be reduced in the process anywhere before the cooling step. Depending on the process used, enzymes are needed that operate at 60° C. and/or 85° C.

Viscosity reducing enzymes can be added in different stages of the ethanol production process: mixing and/or saccharification/fermentation. Preferably the enzymes are added in mixing to breakdown initial viscosity.

The benefits of using viscosity reduction enzymes in the ethanol production process are multiple:
Higher dry substance mash can be used in the process
Higher solids content of final syrup can be obtained
Better heat transfer, lower energy requirement
Reduced evaporator fouling leading to reduced cleaning costs
Increased final ethanol yields
Improved quality of DDGS Methods A Rapid Visco Analyzer (RVA 4500) from Perten Instruments was used to measure viscosity profiles of a wheat mash. This wheat mash was prepared according to following protocol:
Prepare 60 grams of 30% DS (34.65% 'as is') wheat slurry (for simultaneous runs on two RVA's) as follows:
Weigh 20.80 grams of wheat
In a 100 ml beaker glass, weigh 39.20 grams of tap water and add 137 µl 4N $H_2SO_4$
Add the wheat to the water and stir for 5 minutes at maximum speed (approx. 500 rpm) with an overhead stirrer
Transfer 25.0 grams of slurry to an RVA cup, add 50-fold diluted enzymes and start RVA run (check if starting pH is around 5.3)
Check pH at end of RVA run (5.6-5.7)

In each experiment (25 grams of slurry), xylanase was dosed at 25 µg protein (per 8.66 g wheat 'as is'), corresponding to 2.9 µg protein/g wheat 'as is'. SPEZYME® CL was dosed at 0.15 kg/MT wheat 'as is' (2.2 AAU/g 'as is' or 2.6 AAU/g DS).

A standard wheat liquefaction was mimicked in the RVA. Pretreatment was performed for 20 minutes at 60° C., followed by a liquefaction step for 30 minutes at 85° C. After pretreatment and liquefaction, slurry was cooled down to 32° C., to determine viscosity at fermentation conditions. Liquefaction pH was kept between 5.3-5.7.

In this experiment, the performance of FveXyn4 was compared to Variant A, B, C, D and E.

| | Viscosity (mPa*s) | | | | | | |
|---|---|---|---|---|---|---|---|
| | Blank (n = 2) | FveXyn4 | Variant A | Variant B | Variant C | Variant D | Variant E |
| After pretreatment (1200 sec. process time) | 533 ± 16 | 206 | 220 | 232 | 224 | 235 | 240 |
| After liquefaction (3120 sec. process time) | 347 ± 16 | 122 | 125 | 135 | 130 | 141 | 145 |
| At fermentation temperature (3660 sec. process time) | 765 ± 20 | 250 | 257 | 282 | 275 | 302 | 298 |

Figure 22:
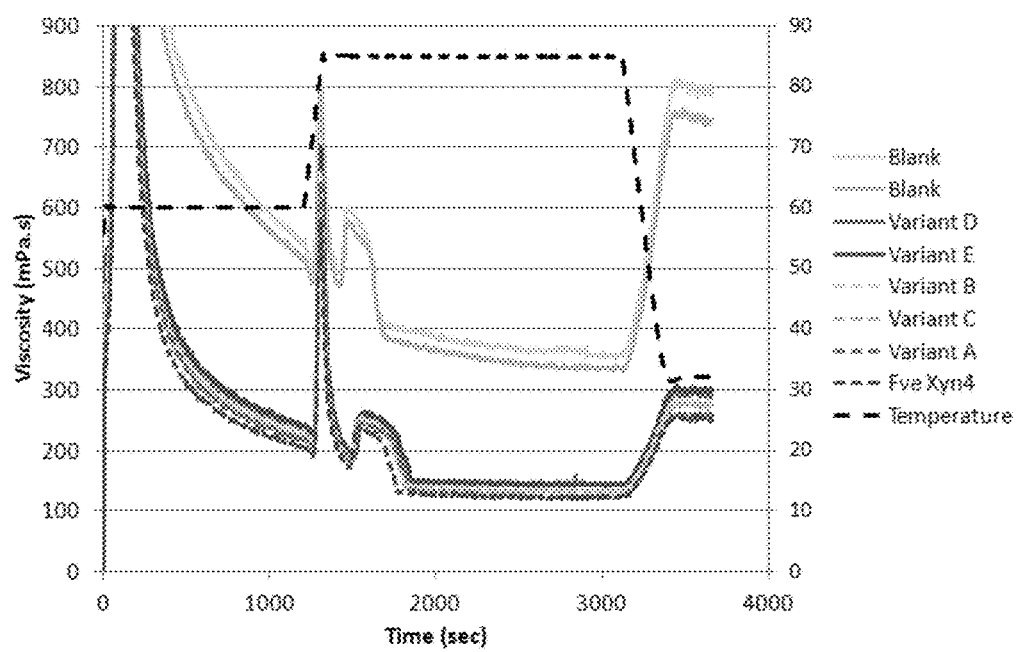
FIG. 22 shows viscosity reduction in grain based material of a backbone (parent) enzyme FveXyn4 compared with thermostable variants A, B, C, D, and E according to the present invention. Fve Xyn4 and the variants perform in a similar way, showing viscosity reduction of 55-67% compared to blank (only SPEZYME® CL).

The results are shown above and in FIG. 22.

These data show that FveXyn4 and all variants perform very similar, showing viscosity reduction of 55-67% compared to blank (only SPEZYME® CL).

Example 7

Wheat Gluten-Starch Separation

Separation of wheat flour into starch and gluten fractions is industrially applied on large scale to obtain high quality A-starch and byproducts B-starch and vital gluten. Separation is improved by addition of xylanases.

7.1 Materials and Methods

The following assay simulates the wheat starch separation of a batter process at 40° C. In this assay, industrial wheat flour (Cargill) is added to preheated tap water (50° C.) to create a 35% DS slurry by mixing 1 minute in a kitchen blender (Braun). pH of the slurry remains 'as is' at ~6.1. 100 gram of this slurry is transferred to the Haake VT550 viscometer, which is calibrated at 40° C. After 1 minute of incubation, the enzyme solution Is added to the slurry. Meanwhile, the viscosity profile is monitored before and after enzyme addition for 15 minutes in total. After incubation, triplicate samples of the incubated slurry and one sample of $t_0$ slurry is taken for a spin test. Each spin test sample has a total weight of 22.5 g, which contains 15.8-15.9 g slurry sample added to 6.6-6.7 g of disposable centrifuge tube (15 ml). All samples are centrifuged in a Hermle Z400 centrifuge for 15 minutes at 3500 rpm. Brix values are determined from the syrup of the centrifuged samples.

Example 8

Cloning of a Backbone (Parent) *Fusarium oxysporum* Xylanase FoxXyn2

The nucleotide sequence of the FoxXyn2 gene isolated from *Fusarium oxysporum* is set forth as SEQ ID No. 30 (FIG. 4A). The signal sequence is shown in bold, and the predicted intron is shown in italics and lowercase.

The amino acid sequence of FoxXyn2 protein is set forth as SEQ ID No. 29 (FIG. 3A). The signal sequence is shown in italics.

The amino acid sequence of the mature form of FoxXyn2 protein is set forth as SEQ ID No. 31 or SEQ ID No. 4 (FIGS. 3B and 3C).

The protein product of gene FoxXyn2 belongs to glycosyl hydrolase family 10. This suggests that FoxXyn2 is a secreted glycosyl hydrolase.

Example 9

Expression of Backbone (Parent) FoxXyn2 Protein

Figure 18:
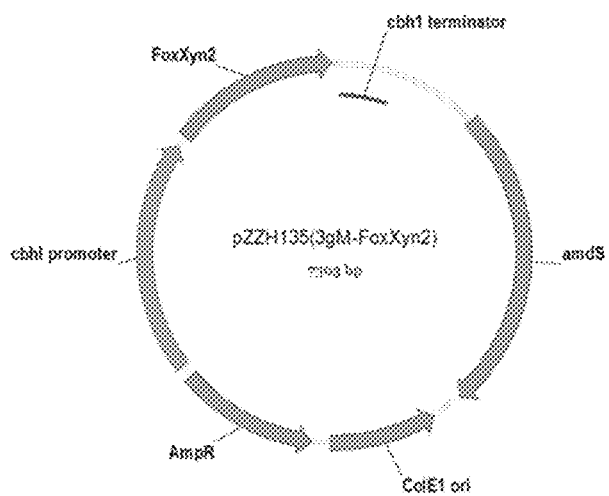
FIG. 18 shows a plasmid map of pZZH135.

The FoxXyn2 gene was amplified from genomic DNA of *Fusarium oxysporum* using the following primers: Primer 1 5'-ccgcggccgcaccATGAAGCTGTCTTCCTTCCTCTA-CACC-3' (SEQ ID NO:24), and Primer 2 5'-ccggcgcgccct-taTTAGCGGAGAGCGTTGACAACAG-3' (SEQ ID NO:25). After digested with Not I and Asc I, the PCR product was cloned into pTrex3gM expression vector (described in US 2011/0136197 A1) digested with the same restriction enzymes, and the resulting plasmid was labeled pZZH135. A plasmid map of pZZH135 is provided in FIG. 18. The sequence of the FoxXyn2 gene was confirmed by DNA sequencing.

The plasmid pZZH135 was transformed into a quad deleted *Trichoderma reesei* strain (described in WO 05/001036, incorporated herein by reference) using biolistic method (taught in Te'o V S et al., *J Microbiol Methods*, 51:393-9, 2002). The protein isolated from the culture supernatant after filtration was used to perform SDS-PAGE analysis and xylanase activity assay to confirm enzyme expression.

The nucleotide sequence of FoxXyn2 gene from expression plasmid pZZH135 is set forth as SEQ ID No. 4. The amino acid sequence of the mature form of FoxXyn2 protein is set forth as SEQ ID No. 3.

FoxXyn2 protein was purified from culture supernatant using affinity chromatography resin Blue Sepharose, 6FF, and samples were used for biochemical characterization as described in subsequent examples.

Example 10

Xylanase Activity of Backbone (Parent) FoxXyn2

FoxXyn2 belongs to the glycosyl hydrolase 10 family (GH10, CAZy number). The beta 1-4 xylanase activity of FoxXyn2 was measured using 1% xylan from birch wood (Sigma 95588) or 1% arabinoxylan from wheat flour (Megazyme P-WAXYM) as substrates. The assay was performed in 50 mM sodium citrate pH 5.3, 0.005% Tween-80 buffer at 50° C. for 10 minutes.

The released reducing sugar was quantified by reaction with 3, 5-Dinitrosalicylic acid and measurement of absorbance at 540 nm. The enzyme activity is quantified relative to a xylose standard curve. In this assay, one xylanase unit (U) is defined as the amount of enzyme required to generate 1 micromole of xylose reducing sugar equivalents per minute under the conditions of the assay.

Example 11

Temperature Profile of FoxXyn2

Figure 19:
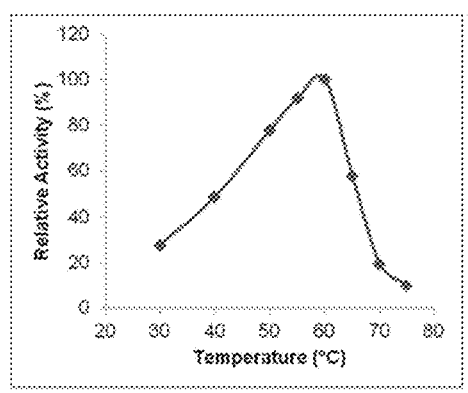
FIG. 19 shows the temperature profile of FoxXyn2.

The temperature optimum of purified FoxXyn2 was determined by assaying for xylanase activity at temperatures varying between 45° C. and 94° C. for 10 minutes in 50 mM sodium citrate buffer at pH 5.3. The activity was reported as relative activity where the activity at the temperature optimum was set to 100%. The temperature profile of FoxXyn2 is shown in FIG. 19. FoxXyn2 was found to have an optimum temperature of 60° C., and was found to retain greater than 50% of maximum activity between 40° C. and 65° C.

Example 12

Thermostability

Thermostability of the FveXyn4 wildtype (wt) and variants of FveXyn4 was measured at 63° C. (see data in Table 2). It is clearly seen that all variants representing different numbers (2-4) and combinations of mutations has higher residual activity at 63° C. compared to FveXyn4 and it can be concluded that these variants are all more thermostable than FveXyn4 wildtype (e.g. shown herein as SEQ ID No. 1, or SEQ ID No. 27).

Materials and Methods

Variants of FveXyn4 were obtained from combinatorial libraries or by introduction of specific mutations as described in Example 1. The thermostability of the FveXyn4 variants was measured by diluting and pre-incubating the enzyme samples in 25 mM MES buffer (0.00125% Tween 80-25 mM MES buffer, pH 6.0, 0.00125% (V:V) Tween 80), pH 6.0 for 10 min at 63° C. After incubation the residual activity was measured by the xylanase activity method described in Example 1. Activity measured without pre-incubation was set to 100% and the residual activity of each variant at the respective temperature was calculated as relative to this.

Table 2 shows 14 combinatorial variants of FveXyn4 with significantly increased thermostability as compared to FveXyn4 wt. Thermostability is measured as residual activity after pre-incubation at 63° C. for 10 min as described in above in the Materials and methods section of this Example 12.

TABLE 2

| Variant | Mutations | Residual activity at 63° C. |
|---|---|---|
| FveXyn4 | WT | 0.04 |
| 1 | K79F_A217Q_T298F | 0.89 |
| 2 | N7D_T33V_A217Q_T298F | 0.80 |
| 3 | N7D_K79F_T298F | 0.79 |
| 4 | T33V_K79F_A217Q | 0.77 |
| 5 | N7D_T33V_T298Y | 0.76 |
| 6 | T33V_A217Q_T298Y | 0.67 |
| 7 | N7D_A217Q_T298F | 0.65 |
| 8 | N7D_T33V_A217Q | 0.60 |
| 9 | K79F_T298F | 0.59 |
| 10 | N7D_K79F | 0.58 |
| 11 | T33V_K79F | 0.57 |
| 12 | T33V_T298Y | 0.55 |
| 13 | N7D_T33V | 0.40 |
| 14 | T33V_A217Q | 0.35 |

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

What is claimed is:

1. A GH10 xylanase variant having increased thermostability compared with a parent GH10 xylanase enzyme comprising at least 90% sequence identity with the amino acid sequence of SEQ ID No. 1 wherein the variant has been modified at two or more of the following positions 7, 33, 79, 217 and 298 corresponding to the amino acid numbering of SEQ ID No. 1.

2. The GH10 xylanase variant of claim 1 wherein the modification is selected from the following:
N7D;
T33V;
K79Y, V, F, I, L or M;
A217Q, E, P, D or M; and/or
T298Y, F or W.

3. The GH10 xylanase variant of claims 1 or 2 wherein the parent GH10 xylanase is further modified at one or more of the following positions: 25, 57, 62, 64, 89, 103, 115, 147, 181, 193 and 219.

4. The GH10 xylanase variant of claim 3 wherein the modification is selected from the following:
N25P;
S57Q, T or V;
N62T or S;
G64T or S;
S89G, N, Q, L or M;
T103M or K;
V115E or L;
N147Q;
G181Q, A, D or P;
S193Y or N, and/or
G219D or P.

5. The GH10 xylanase variant of claim 4 wherein the modification is selected from the following:
i. N7D, N25P, T33V, G64T, K79Y, S89G, A217Q and T298Y;
ii. N7D, N25P, T33V, K79Y, S89G, A217Q and T298Y;
iii. N7D, N25P, T33V, S57Q, N62T, G64T, K79Y, T103M, V115L, N147Q, G181Q, S193Y, A217Q, G219P and T298Y;
iv. N7D, N25P, T33V, S57Q, N62T, K79Y, S89G, T103M, V115L, N147Q, G181Q, S193Y, A217Q, G219P and T298Y;
v. N7D, T33V, S57Q, N62T, G64T, K79Y, S89G, A217Q and T298Y;
vi. K79F, A217Q and T298F;
vii. N7D, T33V, A217Q and T298F;
viii. N7D, K79F and T298F;
ix. T33V, K79F and A217Q;
x. N7D, T33V and T298Y;
xi. T33V, A217Q and T298Y;
xii. N7D, A217Q and T298F;
xiii. N7D, T33V and A217Q;
xiv. K79F and T298F;
xv. N7D and K79F;
xvi. T33V and K79F;
xvii. T33V and T298Y;
xviii. N7D and T33V; and
xix. T33V and A217Q.

6. A recombinant nucleic acid molecule encoding the GH10 xylanase variant of any of claims 1 or 2.

7. A recombinant nucleic acid molecule encoding the GH10 xylanase variant of claim 3.

8. A vector, recombinant construct or host cell comprising the recombinant nucleic acid of claim 6.

9. A vector, recombinant construct or host cell comprising the recombinant nucleic acid of claim 7.

10. The host cell of claim 8 wherein the cell is selected from the group consisting of a fungal cell, a yeast cell, a filamentous fungal cell and a plant cell.

11. An enzyme composition or a feed additive composition comprising the GH10 xylanase variant of claims 1 or 2.

12. An enzyme composition or a feed additive composition comprising the GH10 xylanase variant of claim 3.

13. A premix comprising a modified GH10 xylanase variant of claims 1 or 2 and at least one vitamin and/or at least one mineral.

14. A premix comprising a modified GH10 xylanase variant of claim 3 and at least one vitamin and/or at least one mineral.

15. The enzyme composition or feed additive composition of claim 11 which further comprises one or more of the enzymes selected from the group consisting of at least one protease, at least one amylase, at least one phytase and/or a beta-glucanase.

16. The enzyme composition or feed additive composition of claim 12 which further comprises one or more of the enzymes selected from the group consisting of at least one protease, at least one amylase, at least one phytase and/or a beta-glucanase.

17. A feed or feedstuff comprising the GH10 xylanase variant composition or feed additive composition of claim 11.

18. A feed or feedstuff comprising the GH10 xylanase variant composition or feed additive composition of claim 12.

19. A method for enhancing animal performance which comprises administering to the animal an effective amount of the feed or feedstuff of claim 17 or 18.

20. A method for degrading arabinoxylan in a xylan-containing material comprising contacting the xylan-containing material with the GH10 xylanase variant of claims 1 or 2.

21. A method for degrading arabinoxylan in a xylan-containing material comprising contacting the xylan-containing material with the enzyme composition or feed additive composition of claim 11.

22. A method for degrading arabinoxylan in a xylan-containing material comprising contacting the xylan-containing material with the with the GH10 xylanase variant of claim 3.

23. A method for degrading arabinoxylan in a xylan-containing material comprising contacting the xylan-containing material with the enzyme composition or feed additive composition of claim 12.

24. The method of claim 20 wherein the arabinoxylan is insoluble arabinoxylan.

25. The method of claim 21 wherein the arabinoxylan is insoluble arabinoxylan.

26. The method of claim 22 wherein the arabinoxylan is insoluble arabinoxylan.

27. The method of claim 23 wherein the arabinoxylan is insoluble arabinoxylan.

28. The method of claim 20 wherein the xylan-containing material is selected from one or more of the group consisting of a feed or feedstuff; a feed component; a grain-based material; a mash; a wort; a malt; malted barley; an adjunct, a barley mash; and a cereal flour.

29. The method of claim 21 wherein the xylan-containing material is selected from one or more of the group consisting of a feed or feedstuff; a feed component; a grain-based material; a mash; a wort; a malt; malted barley; an adjunct, a barley mash; and a cereal flour.

30. The method of claim 22 wherein the xylan-containing material is selected from one or more of the group consisting of a feed or feedstuff; a feed component; a grain-based material; a mash; a wort; a malt; malted barley; an adjunct, a barley mash; and a cereal flour.

31. The method of claim 23 wherein the xylan-containing material is selected from one or more of the group consisting of a feed or feedstuff; a feed component; a grain-based material; a mash; a wort; a malt; malted barley; an adjunct, a barley mash; and a cereal flour.

32. A method for producing a GH10 xylanase variant, said method comprising:
    a) transforming an expression host with the recombinant construct of claim 8 and
    b) culturing the expression host of step (a) under conditions to allow expression of the GH10 xylanase variant.

33. A method for producing fermentation products from starch-containing material comprising:
    (a) liquefying the starch-containing material with an enzyme cocktail comprising the GH 10 xylanase variant of claim 1 or 2;
    (b) saccharifying the product of step (a);
    (c) fermenting with a suitable organism; and
    (d) optionally, recovering the product produced in step (c).

34. The method of claim 33 wherein steps (b) and (c) are performed simultaneously.

35. A method for producing fermentation products from starch-containing material comprising:
    (a) liquefying the starch-containing material with an enzyme cocktail comprising the GH 10 xylanase variant claim 3;
    (b) saccharifying the product of step (a);
    (c) fermenting with a suitable organism; and
    (d) optionally, recovering the product produced in step (c).

36. The method of claim 35 wherein steps (b) and (c) are performed simultaneously.

37. A method for reducing viscosity of a liquefied starch-containing material which comprises contacting a slurry of starch-containing material with a GH 10 xylanase variant of claim 1 or 2.

38. A method for reducing viscosity of a liquefied starch-containing material which comprises contacting a slurry of starch-containing material with a GH 10 xylanase variant of claim 3.

39. A method for hydrolyzing arabinoxylans in grain-based material comprising
    (a) contacting the grain-based material with a liquid; and
    (b) hydrolyzing the arabinoxylans in the grain-based material by contacting the grain-based material a GH 10 xylanase variant of claim 1 or 2.

40. A method for hydrolyzing arabinoxylans in grain-based material comprising
    (a) contacting the grain-based material with a liquid; and
    (b) hydrolyzing the arabinoxylans in the grain-based material by contacting the grain-based material with a GH 10 xylanase variant of claim 3.

41. A recombinant nucleic acid molecule encoding the GH10 xylanase variant of claim 4.

42. A recombinant nucleic acid molecule encoding the GH10 xylanase variant of claim 5.

43. The host cell of claim 9 wherein the cell is selected from the group consisting of a fungal cell, a yeast cell, a filamentous fungal cell and a plant cell.

44. An enzyme composition or a feed additive composition comprising the GH10 xylanase variant of claim 4.

45. An enzyme composition or a feed additive composition comprising the GH10 xylanase variant of claim 5.

46. A premix comprising a modified GH10 xylanase variant of claim 4 and at least one vitamin and/or at least one mineral.

47. A premix comprising a modified GH10 xylanase variant of claim 5 and at least one vitamin and/or at least one mineral.

48. A method for degrading arabinoxylan in a xylan-containing material comprising contacting the xylan-containing material with the GH10 xylanase variant of claim 4.

49. A method for degrading arabinoxylan in a xylan-containing material comprising contacting the xylan-containing material with the GH10 xylanase variant of claim 5.

50. A method for degrading arabinoxylan in a xylan-containing material comprising contacting the xylan-containing material with the enzyme composition or feed additive composition of claim 15.

51. A method for degrading arabinoxylan in a xylan-containing material comprising contacting the xylan-containing material with the enzyme composition or feed additive composition of claim 16.

52. A method for producing a GH10 xylanase variant, said method comprising:
   a) transforming an expression host with the recombinant construct of claim 9 and
   b) culturing the expression host of step (a) under conditions to allow expression of the GH10 xylanase variant.

53. A method for producing fermentation products from starch-containing material comprising:
   (a) liquefying the starch-containing material with an enzyme cocktail comprising the GH 10 xylanase variant of claim 4;
   (b) saccharifying the product of step (a);
   (c) fermenting with a suitable organism; and
   (d) optionally, recovering the product produced in step (c).

54. A method for producing fermentation products from starch-containing material comprising:
   (a) liquefying the starch-containing material with an enzyme cocktail comprising the GH 10 xylanase variant of claim 5;
   (b) saccharifying the product of step (a);
   (c) fermenting with a suitable organism; and
   (d) optionally, recovering the product produced in step (c).

55. A method for reducing viscosity of a liquefied starch-containing material which comprises contacting a slurry of starch-containing material with a GH 10 xylanase variant of claim 4.

56. A method for reducing viscosity of a liquefied starch-containing material which comprises contacting a slurry of starch-containing material with a GH 10 xylanase variant of claim 5.

57. A method for hydrolyzing arabinoxylans in grain-based material comprising
   (a) contacting the grain-based material with a liquid; and
   (b) hydrolyzing the arabinoxylans in the grain-based material by contacting the grain-based material with a GH 10 xylanase variant of claim 4.

58. A method for hydrolyzing arabinoxylans in grain-based material comprising
   (a) contacting the grain-based material with a liquid; and
   (b) hydrolyzing the arabinoxylans in the grain-based material by contacting the grain-based material with a GH 10 xylanase variant of claim 5.

* * * * *